(12) United States Patent
Connor

(10) Patent No.: US 11,484,322 B2
(45) Date of Patent: Nov. 1, 2022

(54) ANEURYSM NECK BRIDGE WITH A CLOSEABLE OPENING OR LUMEN THROUGH WHICH EMBOLIC MATERIAL IS INSERTED INTO THE ANEURYSM SAC

(71) Applicant: Robert A. Connor, St. Paul, MN (US)

(72) Inventor: Robert A. Connor, St. Paul, MN (US)

(73) Assignee: Aneuclose LLC, St. Paul, MN (US)

( * ) Notice: Subject to any disclaimer, the term of this patent is extended or adjusted under 35 U.S.C. 154(b) by 0 days.

(21) Appl. No.: 17/214,827

(22) Filed: Mar. 27, 2021

(65) Prior Publication Data

US 2021/0236139 A1 Aug. 5, 2021

Related U.S. Application Data

(63) Continuation-in-part of application No. 16/693,267, filed on Nov. 23, 2019, and a continuation-in-part of application No. 16/660,929, filed on Oct. 23, 2019, said application No. 16/693,267 is a continuation-in-part of application No. 16/660,929, filed on Oct. 23, 2019, and a continuation of application No. 16/541,241, filed on Aug. 15, 2019, now abandoned, and a continuation-in-part of application No. 16/541,241, filed on Aug. 15, 2019, now abandoned, application No. 17/214,827, which is a continuation-in-part of application No. 16/541,241, filed on Aug. 15, 2019, now abandoned, said application No. 16/693,267 is a continuation-in-part of application No. 15/865,822, filed on Jan. 9, 2018, now Pat. No. 10,716,573, and a continuation-in-part of application No. 15/861,482, filed on Jan. 3, 2018, now abandoned.

(60) Provisional application No. 63/119,774, filed on Dec. 1, 2020, provisional application No. 62/794,609, filed on Jan. 19, 2019, provisional application No. 62/794,607, filed on Jan. 19, 2019.

(51) Int. Cl.
*A61B 17/12* (2006.01)
*A61B 17/00* (2006.01)

(52) U.S. Cl.
CPC .. *A61B 17/12172* (2013.01); *A61B 17/12113* (2013.01); *A61B 2017/00867* (2013.01)

(58) Field of Classification Search
CPC ........ A61B 17/12118; A61B 17/12113; A61B 17/12177; A61B 17/12168; A61B 2017/12151
See application file for complete search history.

(56) References Cited

U.S. PATENT DOCUMENTS 4,085,757 A * 4/1978 Pevsner ........... A61B 17/12136 606/195
4,341,218 A    7/1982 U
4,364,392 A   12/1982 Strother et al.
(Continued)

*Primary Examiner* — Diane D Yabut
*Assistant Examiner* — Christina C Lauer

(57) ABSTRACT

This intrasacular aneurysm occlusion device includes a neck bridge with a closeable opening through which embolic material is inserted into an aneurysm sac. After the neck bridge has been expanded within the aneurysm sac, a catheter is inserted through the opening and embolic material is delivered through the catheter into the aneurysm sac. After the aneurysm sac has been filled with embolic material, the catheter is then withdrawn and the opening is closed so that embolic material does not escape out of the aneurysm sac.

3 Claims, 21 Drawing Sheets

(56) References Cited

U.S. PATENT DOCUMENTS

| | | | |
|---|---|---|---|
| 4,638,803 | A | 1/1987 | Rand |
| 5,041,090 | A | 8/1991 | Scheglov et al. |
| 5,053,013 | A * | 10/1991 | Ensminger ......... A61M 39/0606 604/167.04 |
| 5,334,210 | A | 8/1994 | Gianturco |
| 5,690,666 | A | 11/1997 | Berenstein et al. |
| 5,935,148 | A | 8/1999 | Villar et al. |
| 6,063,104 | A | 5/2000 | Villar et al. |
| 6,346,117 | B1 | 2/2002 | Greenhalgh |
| 6,350,270 | B1 | 2/2002 | Roue |
| 6,391,037 | B1 | 5/2002 | Greenhalgh |
| 6,463,317 | B1 * | 10/2002 | Kucharczyk ......... A61B 5/02014 600/411 |
| 6,511,468 | B1 | 1/2003 | Cragg et al. |
| 6,522,926 | B1 * | 2/2003 | Kieval ............... A61N 1/36117 607/2 |
| 6,530,934 | B1 | 3/2003 | Jacobsen et al. |
| 6,585,748 | B1 | 7/2003 | Jeffree |
| 6,855,153 | B2 | 2/2005 | Saadat |
| 6,958,061 | B2 | 10/2005 | Truckai et al. |
| 7,083,643 | B2 | 8/2006 | Whalen et al. |
| 7,153,323 | B1 | 12/2006 | Teoh et al. |
| 7,695,488 | B2 | 4/2010 | Berenstein et al. |
| 8,597,320 | B2 | 12/2013 | Sepetka et al. |
| 8,974,512 | B2 | 3/2015 | Aboytes et al. |
| 8,998,947 | B2 | 4/2015 | Aboytes et al. |
| 9,078,658 | B2 | 7/2015 | Hewitt et al. |
| 9,157,174 | B2 | 10/2015 | Kusleika |
| 9,393,022 | B2 | 7/2016 | Becking et al. |
| 9,492,174 | B2 | 11/2016 | Hewitt et al. |
| 9,561,122 | B2 | 2/2017 | Kusleika |
| 9,592,363 | B2 | 3/2017 | Griffin et al. |
| 9,597,087 | B2 | 3/2017 | Marchand et al. |
| 9,629,635 | B2 | 4/2017 | Hewitt et al. |
| 9,687,245 | B2 | 6/2017 | Molaei et al. |
| 9,844,382 | B2 | 12/2017 | Aboytes et al. |
| 9,931,495 | B2 | 4/2018 | Aboytes |
| 9,955,976 | B2 | 5/2018 | Hewitt et al. |
| 9,980,733 | B2 | 5/2018 | Badruddin et al. |
| 10,130,372 | B2 | 11/2018 | Griffin |
| 10,285,711 | B2 | 5/2019 | Griffin |
| 10,314,593 | B2 | 6/2019 | Bardsley et al. |
| 10,327,781 | B2 | 6/2019 | Divino et al. |
| 10,342,548 | B2 | 7/2019 | Duncan |
| 10,383,635 | B2 | 8/2019 | Wallace et al. |
| 10,383,749 | B2 | 8/2019 | Zhou et al. |
| 10,398,441 | B2 | 9/2019 | Warner et al. |
| 10,405,966 | B2 | 9/2019 | Johnson |
| 10,406,010 | B2 | 9/2019 | Bourang |
| 10,420,862 | B2 | 9/2019 | Sharma et al. |
| 10,426,486 | B2 | 10/2019 | Guo et al. |
| 10,426,487 | B2 | 10/2019 | Bachman et al. |
| 10,433,853 | B2 | 10/2019 | Divino et al. |
| 10,595,875 | B2 | 3/2020 | Mayer et al. |
| 10,610,231 | B2 | 4/2020 | Marchand et al. |
| 10,617,426 | B2 | 4/2020 | Aboytes et al. |
| 10,617,427 | B2 | 4/2020 | Aboytes et al. |
| 10,653,425 | B1 | 5/2020 | Gorochow et al. |
| 10,675,036 | B2 | 6/2020 | Rosqueta et al. |
| 10,675,037 | B2 | 6/2020 | Aboytes et al. |
| 10,716,574 | B2 | 7/2020 | Lorenzo et al. |
| 10,729,447 | B2 | 8/2020 | Shimizu et al. |
| 10,736,758 | B2 | 8/2020 | Ruvalcaba et al. |
| 10,813,645 | B2 | 10/2020 | Hewitt et al. |
| 10,856,879 | B2 | 12/2020 | Badruddin et al. |
| 10,856,880 | B1 | 12/2020 | Badruddin et al. |
| 10,869,672 | B2 | 12/2020 | Griffin |
| 10,881,413 | B2 | 1/2021 | Merritt et al. |
| 10,898,199 | B2 | 1/2021 | Wilson et al. |
| 10,905,430 | B2 | 2/2021 | Lorenzo et al. |
| 10,905,431 | B2 | 2/2021 | Gorochow |
| 10,939,914 | B2 | 3/2021 | Hewitt et al. |
| 10,939,915 | B2 | 3/2021 | Gorochow et al. |
| 2001/0034531 | A1 | 10/2001 | Ho et al. |
| 2002/0026210 | A1 | 2/2002 | Abdel-Gawwad |
| 2002/0026217 | A1 | 2/2002 | Baker et al. |
| 2002/0165572 | A1 | 11/2002 | Saadat |
| 2002/0169473 | A1 | 11/2002 | Sepetka et al. |
| 2003/0028209 | A1 | 2/2003 | Teoh et al. |
| 2003/0212419 | A1 | 11/2003 | West |
| 2004/0010263 | A1 | 1/2004 | Boucher et al. |
| 2004/0098027 | A1 | 5/2004 | Teoh et al. |
| 2004/0254625 | A1 * | 12/2004 | Stephens ........... A61B 17/12022 623/1.1 |
| 2005/0142163 | A1 | 6/2005 | Hunter et al. |
| 2006/0052816 | A1 | 3/2006 | Bates et al. |
| 2006/0116709 | A1 | 6/2006 | Sepetka et al. |
| 2006/0149309 | A1 | 7/2006 | Paul et al. |
| 2006/0155323 | A1 | 7/2006 | Porter et al. |
| 2006/0167494 | A1 | 7/2006 | Suddaby |
| 2008/0281350 | A1 * | 11/2008 | Sepetka ........... A61B 17/12172 606/200 |
| 2009/0112249 | A1 | 4/2009 | Miles et al. |
| 2009/0287294 | A1 | 11/2009 | Rosqueta et al. |
| 2009/0318948 | A1 | 12/2009 | Linder et al. |
| 2011/0046658 | A1 * | 2/2011 | Connor ............ A61B 17/12172 606/200 |
| 2011/0184451 | A1 | 7/2011 | Sahl |
| 2011/0196413 | A1 | 8/2011 | Wallace et al. |
| 2012/0239074 | A1 | 9/2012 | Aboytes et al. |
| 2012/0265287 | A1 | 10/2012 | Sharma et al. |
| 2012/0283768 | A1 | 11/2012 | Cox et al. |
| 2013/0116722 | A1 | 5/2013 | Aboytes et al. |
| 2013/0245667 | A1 | 9/2013 | Marchand et al. |
| 2014/0052233 | A1 | 2/2014 | Cox et al. |
| 2014/0135812 | A1 | 5/2014 | Divino et al. |
| 2014/0330299 | A1 | 11/2014 | Rosenbluth et al. |
| 2015/0005807 | A1 | 1/2015 | Lagodzki et al. |
| 2015/0196744 | A1 | 7/2015 | Aboytes |
| 2015/0209050 | A1 | 7/2015 | Aboytes et al. |
| 2015/0216684 | A1 | 8/2015 | Enzmann et al. |
| 2015/0272590 | A1 | 10/2015 | Aboytes et al. |
| 2015/0313605 | A1 | 11/2015 | Griffin |
| 2015/0342613 | A1 | 12/2015 | Aboytes et al. |
| 2016/0022445 | A1 | 1/2016 | Ruvalcaba et al. |
| 2016/0045201 | A1 | 2/2016 | Rosenbluth et al. |
| 2016/0213380 | A1 | 7/2016 | O'Brien et al. |
| 2016/0249934 | A1 | 9/2016 | Hewitt et al. |
| 2016/0249935 | A1 | 9/2016 | Hewitt et al. |
| 2016/0249937 | A1 | 9/2016 | Marchand et al. |
| 2016/0262766 | A1 | 9/2016 | Aboytes et al. |
| 2016/0367260 | A9 | 12/2016 | Hewitt et al. |
| 2017/0079661 | A1 | 3/2017 | Bardsley et al. |
| 2017/0086851 | A1 | 3/2017 | Wallace et al. |
| 2017/0095254 | A1 | 4/2017 | Hewitt et al. |
| 2017/0128077 | A1 | 5/2017 | Hewitt et al. |
| 2017/0156734 | A1 | 6/2017 | Griffin |
| 2017/0224355 | A1 * | 8/2017 | Bowman ........... A61B 17/12031 |
| 2017/0245862 | A1 | 8/2017 | Cox et al. |
| 2017/0252190 | A1 | 9/2017 | Becking et al. |
| 2017/0258473 | A1 | 9/2017 | Plaza et al. |
| 2017/0273692 | A1 | 9/2017 | Choubey |
| 2017/0281194 | A1 | 10/2017 | Divino et al. |
| 2017/0354402 | A1 | 12/2017 | Lee et al. |
| 2017/0354418 | A1 | 12/2017 | Teoh et al. |
| 2018/0000489 | A1 | 1/2018 | Marchand et al. |
| 2018/0036012 | A1 | 2/2018 | Aboytes et al. |
| 2018/0070955 | A1 | 3/2018 | Greene et al. |
| 2018/0125501 | A1 | 5/2018 | Aboytes et al. |
| 2018/0132859 | A1 | 5/2018 | Aboytes et al. |
| 2018/0132862 | A1 | 5/2018 | Aboytes et al. |
| 2018/0206849 | A1 | 7/2018 | Hewitt et al. |
| 2018/0250013 | A1 | 9/2018 | Wallace et al. |
| 2018/0263629 | A1 | 9/2018 | Murphy et al. |
| 2018/0271540 | A1 | 9/2018 | Merritt et al. |
| 2018/0303486 | A1 | 10/2018 | Rosenbluth et al. |
| 2019/0046209 | A1 | 2/2019 | Plaza et al. |
| 2019/0046210 | A1 | 2/2019 | Bowman |
| 2019/0053810 | A1 | 2/2019 | Griffin |
| 2019/0059907 | A1 | 2/2019 | Rosqueta et al. |
| 2019/0059909 | A1 | 2/2019 | Griffin |
| 2019/0069900 | A1 | 3/2019 | Cam et al. |
| 2019/0083075 | A1 | 3/2019 | Onushko et al. |
| 2019/0105054 | A1 | 4/2019 | Aboytes et al. |

(56) References Cited

U.S. PATENT DOCUMENTS

| | | |
|---|---|---|
| 2019/0105056 A1 | 4/2019 | Aboytes et al. |
| 2019/0133794 A1 | 5/2019 | Kusleika |
| 2019/0133795 A1 | 5/2019 | Choubey |
| 2019/0150932 A1 | 5/2019 | Cruise et al. |
| 2019/0167270 A1 | 6/2019 | Chen |
| 2019/0167272 A1 | 6/2019 | Stephens et al. |
| 2019/0192322 A1 | 6/2019 | Choubey et al. |
| 2019/0201000 A1 | 7/2019 | Wallace et al. |
| 2019/0201592 A1 | 7/2019 | Takahashi et al. |
| 2019/0209146 A1 | 7/2019 | Hebert et al. |
| 2019/0209178 A1 | 7/2019 | Richter et al. |
| 2019/0209181 A1 | 7/2019 | Mayer et al. |
| 2019/0216467 A1 | 7/2019 | Goyal |
| 2019/0216468 A1 | 7/2019 | Larsen et al. |
| 2019/0223880 A1 | 7/2019 | Gerberding et al. |
| 2019/0223881 A1 | 7/2019 | Hewitt et al. |
| 2019/0223883 A1 | 7/2019 | Anderson et al. |
| 2019/0231328 A1 | 8/2019 | Hebert et al. |
| 2019/0239895 A1 | 8/2019 | Dawson et al. |
| 2019/0240049 A1 | 8/2019 | Dawson et al. |
| 2019/0240050 A1 | 8/2019 | Dawson et al. |
| 2019/0247053 A1 | 8/2019 | Inouye |
| 2019/0251866 A1 | 8/2019 | Babiker et al. |
| 2019/0254676 A1 | 8/2019 | Murphy et al. |
| 2019/0254691 A1 | 8/2019 | Martin et al. |
| 2019/0261967 A1 | 8/2019 | Hebert et al. |
| 2019/0262002 A1 | 8/2019 | Benjamin |
| 2019/0262119 A1 | 8/2019 | Gupta et al. |
| 2019/0262123 A1 | 8/2019 | Mangiardi |
| 2019/0269411 A1 | 9/2019 | Bardsley et al. |
| 2019/0269414 A1 | 9/2019 | Griffin |
| 2019/0269533 A1 | 9/2019 | Vong et al. |
| 2019/0269534 A1 | 9/2019 | Choubey |
| 2019/0274691 A1 | 9/2019 | Sepetka et al. |
| 2019/0282242 A1 | 9/2019 | Divino et al. |
| 2019/0290286 A1 | 9/2019 | Divino et al. |
| 2019/0298379 A1 | 10/2019 | Porter et al. |
| 2019/0298380 A1 | 10/2019 | Inouye et al. |
| 2019/0307460 A1 | 10/2019 | Ferrera et al. |
| 2019/0307546 A1 | 10/2019 | Aguilar et al. |
| 2019/0343532 A1 | 11/2019 | Divino et al. |
| 2019/0343664 A1 | 11/2019 | Ruvalcaba et al. |
| 2019/0362496 A1 | 11/2019 | Dutta et al. |
| 2020/0038032 A1 | 2/2020 | Rhee et al. |
| 2020/0038035 A1 | 2/2020 | Griffin |
| 2020/0138447 A1 | 5/2020 | Rosqueta et al. |
| 2020/0155333 A1 | 5/2020 | Franano et al. |
| 2020/0163677 A1 | 5/2020 | Mayer et al. |
| 2020/0163784 A1 | 5/2020 | Franano et al. |
| 2020/0170647 A1 | 6/2020 | Chen et al. |
| 2020/0187952 A1 | 6/2020 | Walsh et al. |
| 2020/0187953 A1 | 6/2020 | Hamel et al. |
| 2020/0187954 A1 | 6/2020 | Hamel et al. |
| 2020/0197017 A1 | 6/2020 | Hamel et al. |
| 2020/0197018 A1 | 6/2020 | Hamel et al. |
| 2020/0197020 A1 | 6/2020 | Hamel et al. |
| 2020/0205841 A1 | 7/2020 | Aboytes et al. |
| 2020/0281603 A1 | 9/2020 | Marchand et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2020/0367893 A1 | 11/2020 | Xu et al. |
| 2020/0367895 A1 | 11/2020 | Badruddin et al. |
| 2020/0367896 A1 | 11/2020 | Zaidat et al. |
| 2020/0367897 A1 | 11/2020 | Wolfe et al. |
| 2020/0367900 A1 | 11/2020 | Pedroso et al. |
| 2020/0367904 A1 | 11/2020 | Becking et al. |
| 2021/0000624 A1 | 1/2021 | Cam et al. |
| 2021/0007754 A1 | 1/2021 | Milhous et al. |
| 2021/0007755 A1 | 1/2021 | Lorenzo et al. |
| 2021/0022765 A1 | 1/2021 | Walzman |
| 2021/0045750 A1 | 2/2021 | Wolf et al. |
| 2021/0052278 A1 | 2/2021 | Mauger |
| 2021/0052279 A1 | 2/2021 | Porter et al. |

\* cited by examiner

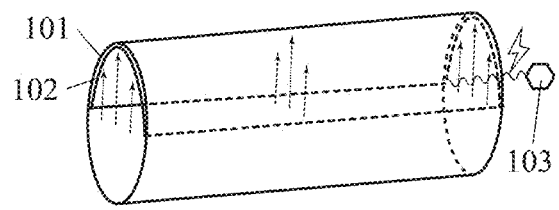
Fig. 1
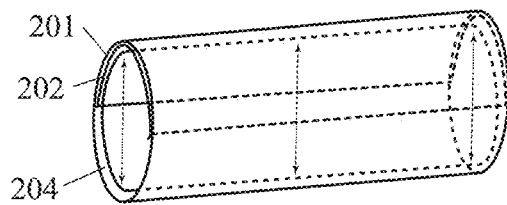
Fig. 2
Fig. 3
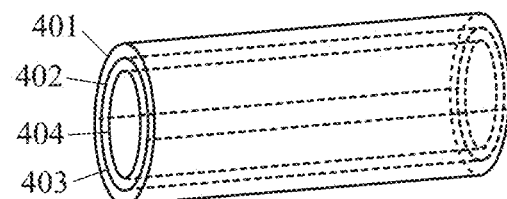
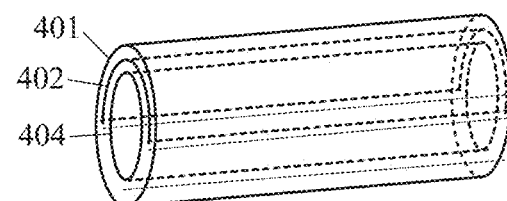
Fig. 4
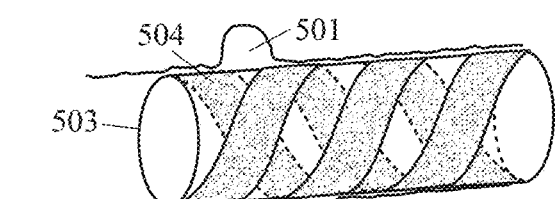
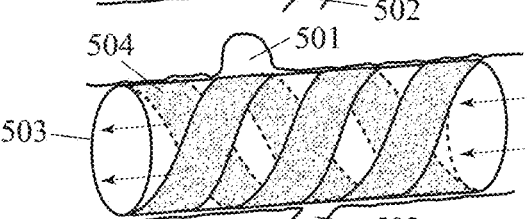
Fig. 5
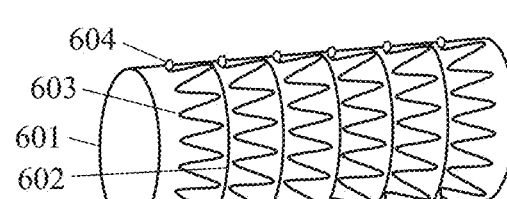
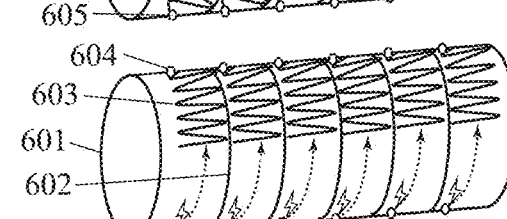
Fig. 6

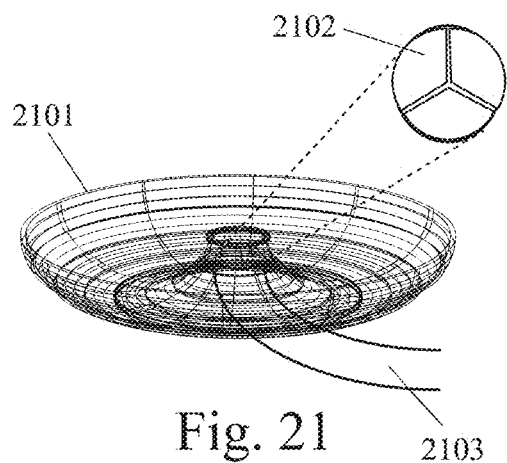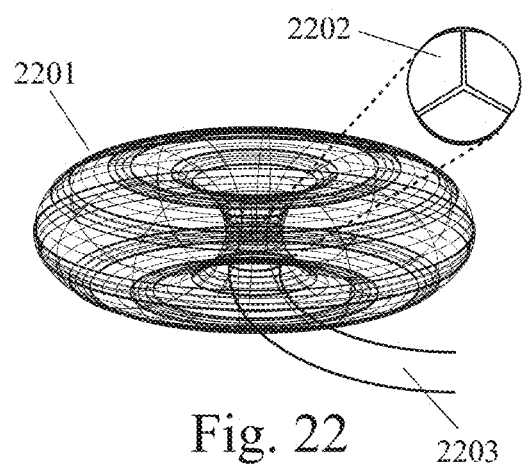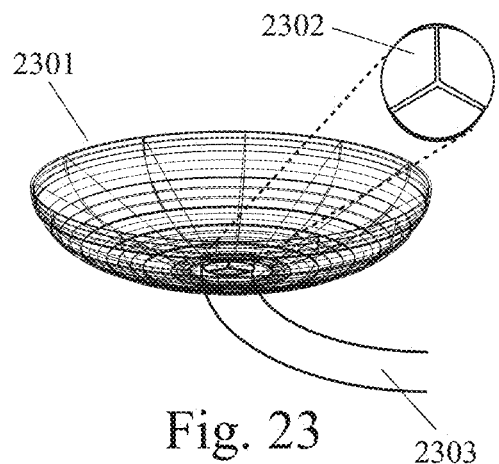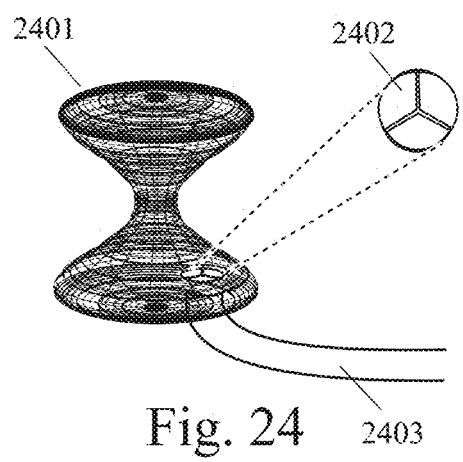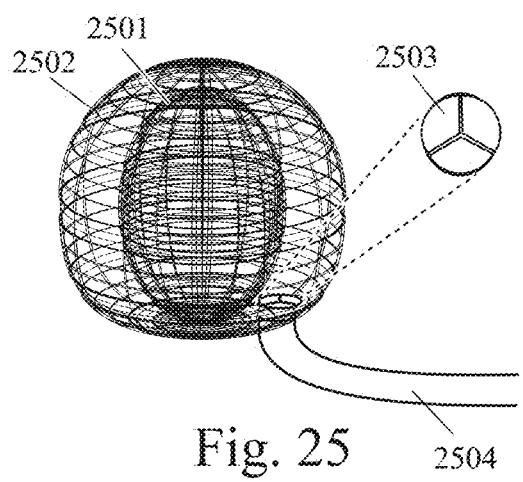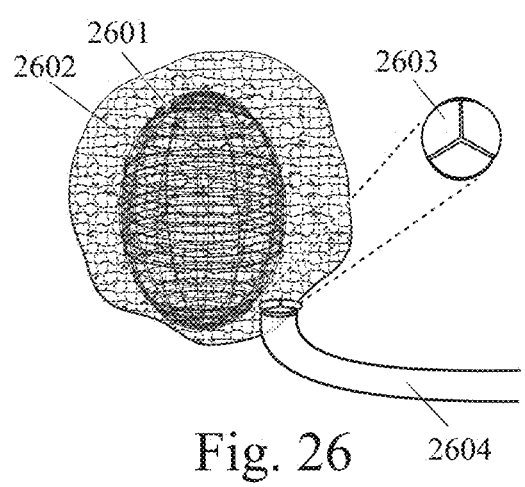

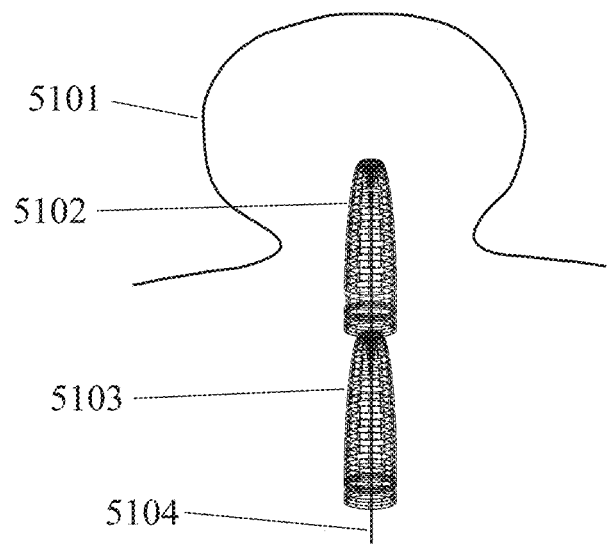
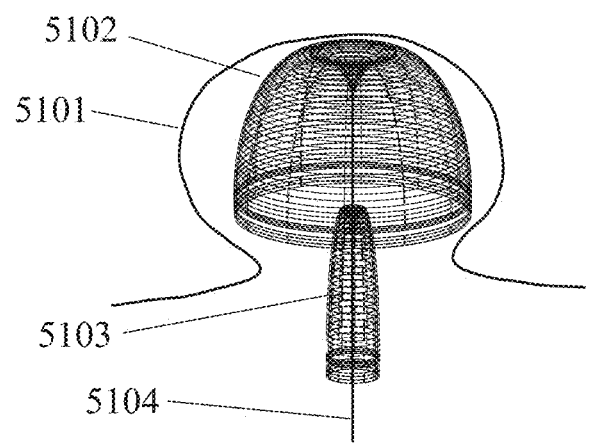
Fig. 51
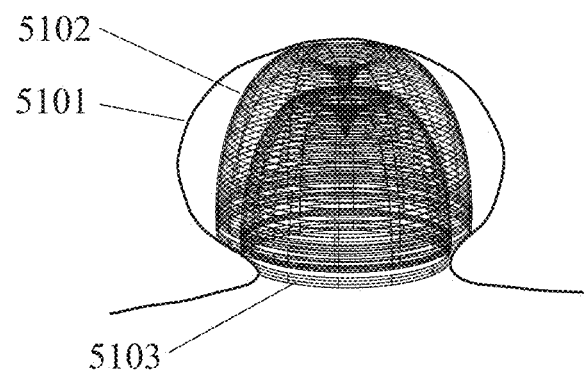

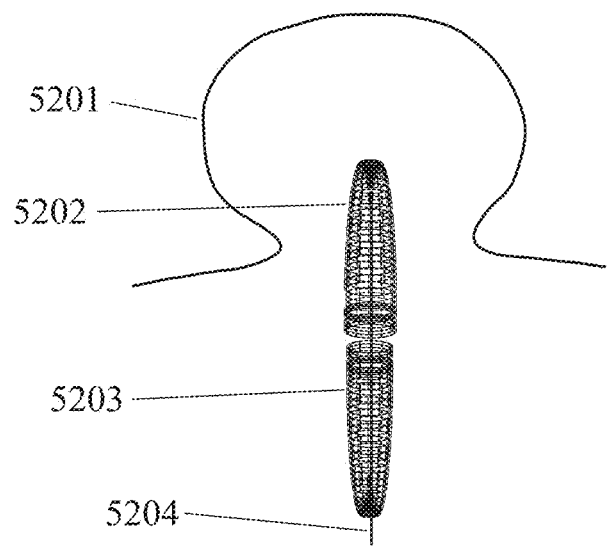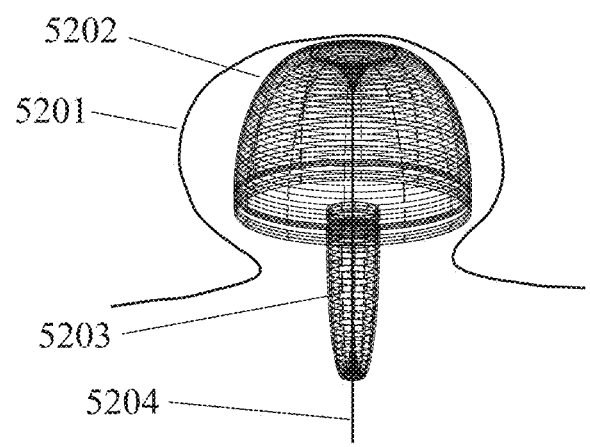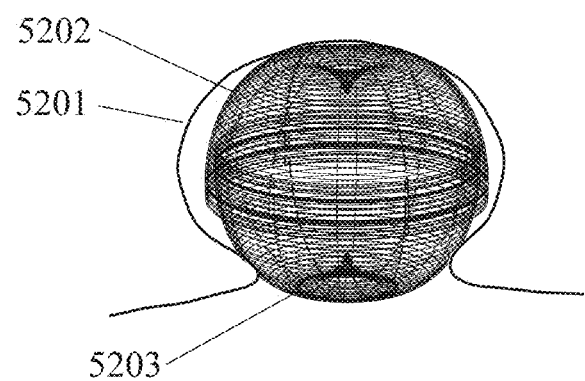
Fig. 52

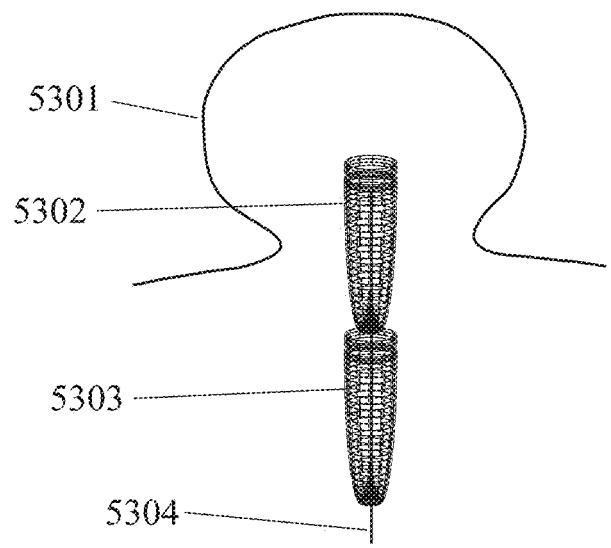
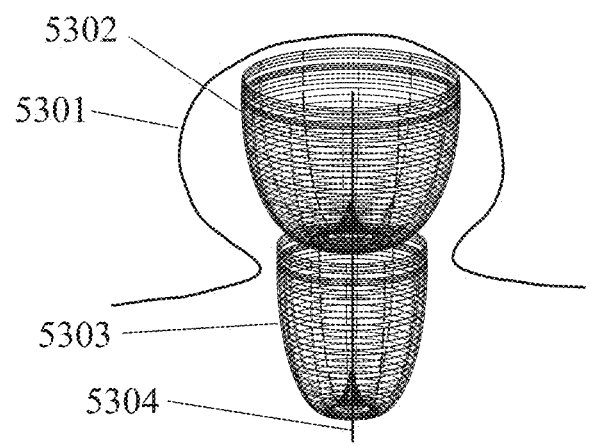
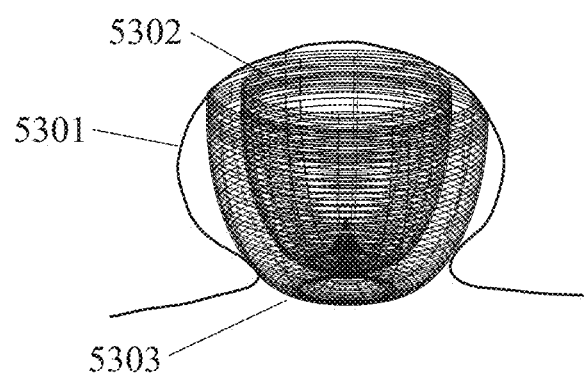
Fig. 53

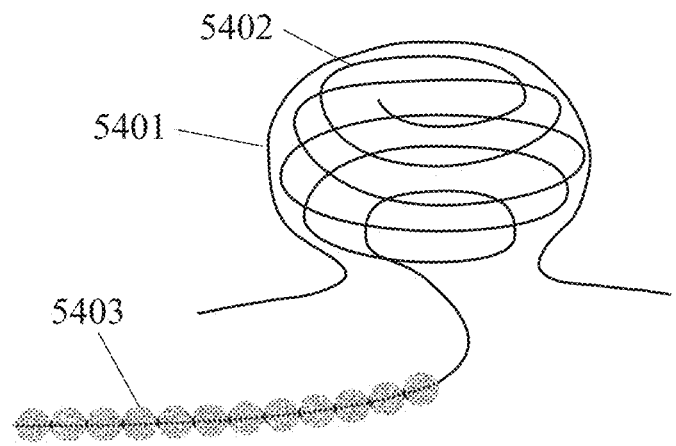
Fig. 54
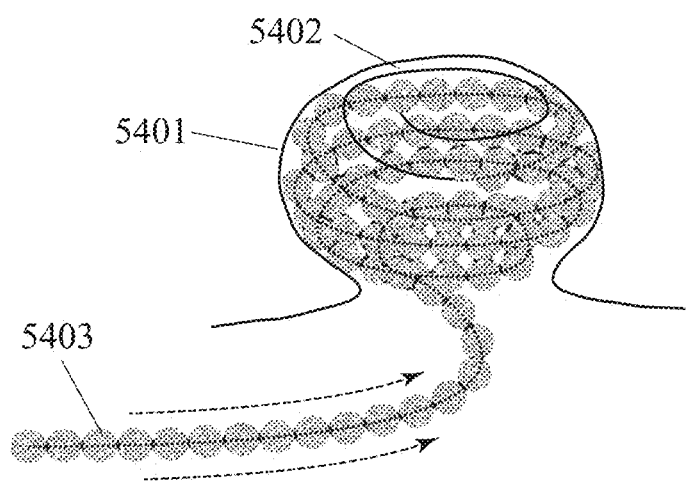
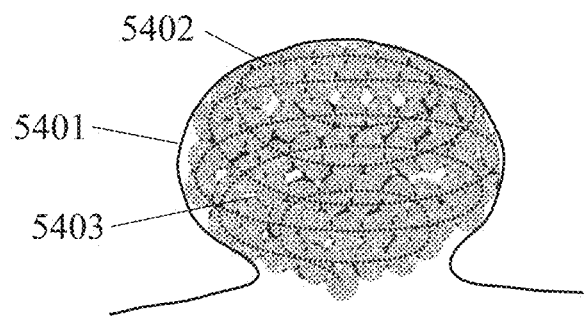

ANEURYSM NECK BRIDGE WITH A CLOSEABLE OPENING OR LUMEN THROUGH WHICH EMBOLIC MATERIAL IS INSERTED INTO THE ANEURYSM SAC

CROSS-REFERENCE TO RELATED APPLICATIONS

This present application claims the priority benefit of provisional patent application 63/119,774 filed on Dec. 1, 2020. This present application is also a continuation-in-part of patent application Ser. No. 16/693,267 filed on Nov. 23, 2019. This present application is also a continuation-in-part of patent application Ser. No. 16/660,929 filed on Oct. 23, 2019. This present application is also a continuation-in-part of patent application Ser. No. 16/541,241 filed on Aug. 15, 2019.

Application Ser. No. 16/693,267 is a continuation-in-part of patent application Ser. No. 16/660,929 filed on Oct. 23, 2019. application Ser. No. 16/693,267 claimed the priority benefit of provisional patent application 62/794,609 filed on Jan. 19, 2019. application Ser. No. 16/693,267 claimed the priority benefit of provisional patent application 62/794,607 filed on Jan. 19, 2019. application Ser. No. 16/693,267 was a continuation-in-part of patent application Ser. No. 16/541,241 filed on Aug. 15, 2019. application Ser. No. 16/693,267 was a continuation-in-part of patent application Ser. No. 15/865,822 filed on Jan. 9, 2018 and issued as patent Ser. No. 10/716,573 on Jul. 21, 2020. application Ser. No. 16/693,267 was a continuation-in-part of patent application Ser. No. 15/861,482 filed on Jan. 3, 2018.

Application Ser. No. 16/660,929 claimed the priority benefit of provisional patent application 62/794,609 filed on Jan. 19, 2019. application Ser. No. 16/660,929 claimed the priority benefit of provisional patent application 62/794,607 filed on Jan. 19, 2019. application Ser. No. 16/660,929 was a continuation-in-part of patent application Ser. No. 16/541,241 filed on Aug. 15, 2019. application Ser. No. 16/660,929 was a continuation-in-part of patent application Ser. No. 15/865,822 filed on Jan. 9, 2018 and issued as patent Ser. No. 10/716,573 on Jul. 21, 2020. application Ser. No. 16/660,929 was a continuation-in-part of patent application Ser. No. 15/861,482 filed on Jan. 3, 2018.

Application Ser. No. 16/541,241 claimed the priority benefit of provisional patent application 62/794,609 filed on Jan. 19, 2019. application Ser. No. 16/541,241 claimed the priority benefit of provisional patent application 62/794,607 filed on Jan. 19, 2019. application Ser. No. 16/541,241 claimed the priority benefit of provisional patent application 62/720,173 filed on Aug. 21, 2018. application Ser. No. 16/541,241 was a continuation-in-part of patent application Ser. No. 15/865,822 filed on 2018 Jan. 9 and issued as patent Ser. No. 10/716,573 on Jul. 21, 2020. application Ser. No. 15/865,822 claimed the priority benefit of provisional patent application 62/589,754 filed on Nov. 22, 2017. application Ser. No. 15/865,822 claimed the priority benefit of provisional patent application 62/472,519 filed on Mar. 16, 2017. application Ser. No. 15/865,822 was a continuation-in-part of patent application Ser. No. 15/081,909 filed on Mar. 27, 2016. application Ser. No. 15/865,822 was a continuation-in-part of patent application Ser. No. 14/526,600 filed on Oct. 29, 2014.

Application Ser. No. 15/861,482 claimed the priority benefit of provisional patent application 62/589,754 filed on Nov. 22, 2017. application Ser. No. 15/861,482 claimed the priority benefit of provisional patent application 62/472,519 filed on Mar. 16, 2017. application Ser. No. 15/861,482 claimed the priority benefit of provisional patent application 62/444,860 filed on Jan. 11, 2017. application Ser. No. 15/861,482 was a continuation-in-part of patent application Ser. No. 15/080,915 filed on Mar. 25, 2016 and issued as patent Ser. No. 10/028,747 on Jul. 24, 2018. application Ser. No. 15/861,482 was a continuation-in-part of patent application Ser. No. 14/526,600 filed on Oct. 29, 2014. application Ser. No. 15/081,909 was a continuation-in-part of patent application Ser. No. 14/526,600 filed on Oct. 29, 2014. application Ser. No. 15/080,915 was a continuation-in-part of patent application Ser. No. 14/526,600 filed on Oct. 29, 2014. application Ser. No. 14/526,600 claimed the priority benefit of provisional patent application 61/897,245 filed on Oct. 30, 2013. application Ser. No. 14/526,600 was a continuation-in-part of patent application Ser. No. 12/989,048 filed on Oct. 21, 2010 and issued as U.S. Pat. No. 8,974,487 on Mar. 10, 2015. application Ser. No. 12/989,048 claimed the priority benefit of provisional patent application 61/126,047 filed on May 1, 2008. application Ser. No. 12/989,048 claimed the priority benefit of provisional patent application 61/126,027 filed on May 1, 2008.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices for occluding cerebral aneurysms.

Introduction

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain. Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function. Better alternatives for cerebral aneurysm treatment are needed.

Review of the Relevant Art

U.S. patent application 20150196744 (Aboytes, Jul. 16, 2015, "Devices and Method for Vascular Recanalization") and U.S. Pat. No. 9,931,495 (Aboytes, Apr. 3, 2018, "Devices and Methods for Vascular Recanalization") disclose a device for restoring blood flow through an obstructed blood vessel. U.S. Pat. No. 8,974,512 (Aboytes et al., Mar. 10, 2015, "Devices and Methods for the Treatment of Vascular Defects"), U.S. Pat. No. 8,998,947 (Aboytes et al., Apr. 7, 2015, "Devices and Methods for the Treatment of Vascular Defects"), and U.S. Pat. No. 9,844,382 (Aboytes et al., Dec. 19, 2017, "Devices and Methods for the Treatment of Vascular Defects"), and U.S. patent applications 20120239074 (Aboytes et al., Sep. 20, 2012, "Devices and Methods for the Treatment of Vascular Defects"), 20130116722 (Aboytes et al., May 9, 2013, "Devices and Methods for the Treatment of Vascular Defects"), 20150209050 (Aboytes et al., Jul. 30, 2015, "Devices and Methods for the Treatment of Vascular Defects"), 20150272590 (Aboytes et al., Oct. 1, 2015, "Devices and Methods for the Treatment of Vascular Defects"), 20150342613 (Aboytes et al., Dec. 3, 2015, "Devices and Methods for the Treatment of Vascular Defects"), 20160262766 (Aboytes et al., Sep. 15, 2016, "Devices and Methods for the Treatment of Vascular Defects"), 20180125501 (Aboytes et al., May 10, 2018, "Devices and Methods for the Treatment of Vascular Defects"), 20180132859 (Aboytes et al., May 17, 2018, "Devices and Methods for the Treatment of Vascular Defects"), 20180132862 (Aboytes et al., May 17, 2018, "Devices and Methods for the Treatment of Vascular Defects"), 20190105054 (Aboytes et al., Apr. 11, 2019, "Devices and Methods for the Treatment of Vascular Defects"), 20190105056 (Aboytes et al., Apr. 11, 2019, "Devices and Methods for the Treatment of Vascular Defects"), and 20180036012 (Aboytes et al., Feb. 8, 2018, "Devices, Systems, and Methods for the Treatment of Vascular Defects") disclose intrasaccular ribbons for aneurysm occlusion. U.S. patent Ser. No. 10/617,426 (Aboytes et al., Apr. 14, 2020, "Devices and Methods for the Treatment of Vascular Defects"), Ser. No. 10/617,427 (Aboytes et al., Apr. 14, 2020, "Devices and Methods for the Treatment of Vascular Defects"), and Ser. No. 10/675,037 (Aboytes et al., Jun. 9, 2020, "Devices and Methods for the Treatment of Vascular Defects"), as well as U.S. patent application 20200205841 (Aboytes et al., Jul. 2, 2020, "Devices, Systems, and Methods for the Treatment of Vascular Defects"), disclose a ribbon-like intrasacular implant with first and second portions, wherein the first and second portions have a first configuration in which are linearly aligned and a second configuration in which they overlap.

U.S. patent application 20020026210 (Abdel-Gawwad, Feb. 28, 2002, "Endovascular Aneurysm Treatment Device and Method") discloses using an intrasacular frame and suction to collapse an aneurysm. U.S. patent application 20190307546 (Aguilar et al., Oct. 10, 2019, "Embolic Device with Improved Neck Coverage") discloses a helical intrasaccular device. U.S. patent application 20190223883 (Anderson et al., Jul. 25, 2019, "Occlusive Medical Device with Delivery System") discloses a neck bridge to occlude a heart appendage. U.S. patent application 20190251866 (Babiker et al., Aug. 15, 2019, "Device Specific Finite Element Models for Simulating Endovascular Treatment") discloses using finite element medical device models and computational fluid dynamics for aneurysm treatment. U.S. patent Ser. No. 10/426,487 (Bachman et al., Oct. 1, 2019, "Devices, Systems and Methods for Enclosing an Anatomical Opening") discloses a device with a distal-facing portion which occludes an aneurysm and a proximal-facing portion which arches over lumina of an artery.

U.S. Pat. No. 9,980,733 (Badruddin et al., May 29, 2018, "System for and Method of Treating Aneurysms") and Ser. No. 10/856,879 (Badruddin et al., Dec. 8, 2020, "System for and Method of Treating Aneurysms") disclose an occlusion device with a cover and an inner anchoring member, wherein the cover expands to a diameter greater than an aneurysm neck and the inner anchoring member contacts the interior of the aneurysm. U.S. patent application 20200367895 (Badruddin et al., Nov. 26, 2020, "Systems and Methods for Treating Aneurysms") and patent Ser. No. 10/856,880 (Badruddin et al., Dec. 8, 2020, "Systems and Methods for Treating Aneurysms") disclose an implantable device with a proximal end seated against an aneurysm adjacent the neck and a distal end extending in the sac away from the neck.

U.S. patent application 20020026217 (Baker et al., Feb. 28, 2002, "Apparatus and Method for Repair of Perigraft Flow") discloses a device for causing thrombus between a graft and an aneurysm wall. U.S. patent applications 20170079661 (Bardsley et al., Mar. 23, 2017, "Occlusive Devices") and 20190269411 (Bardsley et al., Sep. 5, 2019, "Occlusive Devices") disclose dual-layer inverted meshes for vascular occlusion. U.S. patent Ser. No. 10/314,593 (Bardsley et al., Jun. 11, 2019, "Occlusive Devices") discloses dual-layer inverted meshes for vascular occlusion. U.S. patent application 20060052816 (Bates et al., Mar. 9, 2006, "Device for Treating an Aneurysm") discloses a patch that covers an aneurysm neck. U.S. Pat. No. 9,393,022 (Becking et al., Jul. 19, 2016, "Two-Stage Deployment Aneurysm Embolization Devices") discloses embolic implants which are deployed in two stages. U.S. patent application 20170252190 (Becking et al., Sep. 7, 2017, "Braid Implant Delivery Systems") discloses neurovascular devices with low profile compressibility. U.S. patent application 20200367904 (Becking et al., Nov. 26, 2020, "Multiple Layer Filamentary Devices for Treatment of Vascular Defects") discloses braided balls which reduce blood flow into an aneurysm. U.S. patent application 20190262002 (Benjamin, Aug. 29, 2019, "Novel Enhanced Orb-Like Intrasacular Device") discloses an orb-shaped device with zones of flexure and open cells.

U.S. Pat. No. 5,690,666 (Berenstein et al., Nov. 25, 1997, "Ultrasoft Embolism Coils and Process for Using Them") discloses ultrasoft embolism coils. U.S. Pat. No. 7,695,488 (Berenstein et al., Apr. 13, 2010, "Expandable Body Cavity Liner Device") discloses an aneurysm liner with areas with different elasticities. U.S. patent application 20040010263 (Boucher et al., Jan. 15, 2004, "Expandable Preformed Structures for Deployment in Interior Body Regions") discloses using a stylet to straighten an expandable structure during deployment into an interior body region. U.S. patent Ser. No. 10/406,010 (Bourang, Sep. 10, 2019, "Multi-Stent and Multi-Balloon Apparatus for Treating Bifurcations and Methods of Use") discloses using two catheters and three stents to treat a bifurcated vessel. U.S. patent application 20190046210 (Bowman, Feb. 14, 2019, "Embolic Device with Shaped Wire") discloses using a helical carrier to occlude an aneurysm.

U.S. patent application 20190069900 (Cam et al., Mar. 7, 2019, "Vascular Remodeling Device") discloses a vascular remodeling device with a first section and a protruding section. U.S. patent application 20210000624 (Cam et al., Jan. 7, 2021, "Vascular Remodeling Device") discloses a vascular remodeling device with a proximal section, an intermediate section, and a distal section, wherein the distal section is positioned in a vessel bifurcation. U.S. patent application 20190167270 (Chen, Jun. 6, 2019, "Vaso-Occlusive Devices with In-Situ Stiffening") discloses a vaso-occlusive device that is constructed out of dissimilar metallic materials which cause galvanic corrosion. U.S. patent application 20200170647 (Chen et al., Jun. 4, 2020, "Vaso-Occlusive Device") discloses a gold-platinum alloy vaso-occlusive structure which is implanted in an aneurysm sac. U.S. patent application 20190133795 (Choubey, May 9, 2019, "Meshes, Devices and Methods for Treating Vascular Defects") discloses stents with a plurality of strut regions and a plurality of bridge regions. U.S. patent application 20190192322 (Choubey et al., Jun. 27, 2019, "Vascular Flow Diversion") discloses a device with a plurality of connector sections extending circumferentially about the device. U.S. patent applications 20190269534 (Choubey, Sep. 5, 2019, "Thin Film Mesh Hybrid for Treating Vascular Defects") and 20170273692 (Choubey, Sep. 28, 2017, "Thin Wall Constructions for Vascular Flow Diversion") disclose stents with strut regions extending circumferentially about the expandable device.

U.S. patent application 20120283768 (Cox et al., Nov. 8, 2012, "Method and Apparatus for the Treatment of Large and Giant Vascular Defects") discloses a plurality of self-expanding globular shells which are inserted into an aneurysm sac. U.S. patent application 20170245862 (Cox et al., Aug. 31, 2017, "Methods and Devices for Treatment of Vascular Defects") discloses a method for inserting a self-expanding globular shell into an aneurysm sac. U.S. patent application 20140052233 (Cox et al., Feb. 20, 2014, "Methods and Devices for Treatment of Vascular Defects") discloses a self-expanding globular shell which is inserted into an aneurysm sac. U.S. Pat. No. 6,511,468 (Cragg et al., Jan. 28, 2003, "Device and Method for Controlling Injection of Liquid Embolic Composition") discloses a system to deliver liquid embolic material into an aneurysm. U.S. patent application 20190150932 (Cruise et al., May 23, 2019, "Embolization Device Constructed from Expansile Polymer") discloses expandable polymer devices for aneurysm occlusion. U.S. patent application 20190240050 (Dawson et al., Aug. 8, 2019, "Vascular Expandable Devices") discloses a tubular structure made with a plurality of braided metallic elements. U.S. patent applications 20190239895 (Dawson et al., Aug. 8, 2019, "Vascular Expandable Devices") and 20190240049 (Dawson et al., Aug. 8, 2019, "Vascular Expandable Devices") disclose a device with a generally tubular sidewall formed by braided strands.

U.S. patent application 20200289125 (Dholakia et al., Sep. 17, 2020, "Filamentary Devices Having a Flexible Joint for Treatment of Vascular Defects") discloses a permeable implant with first and second permeable shells, wherein the first permeable shell has a proximal end with a concave or recessed section and the second permeable shell has a convex section that mates with the concave or recessed section. U.S. patent application 20170281194 (Divino et al., Oct. 5, 2017, "Embolic Medical Devices") discloses intrasaccular ribbons for aneurysm occlusion. U.S. patent Ser. No. 10/433,853 (Divino et al., Oct. 8, 2019, "Embolic Medical Devices") discloses an intrasaccular ribbon for aneurysm occlusion with a pre-insertion rolled configuration. U.S. patent Ser. No. 10/327,781 (Divino et al., Jun. 25, 2019, "Occlusive Devices") and U.S. patent application 20140135812 (Divino et al., May 15, 2014, "Occlusive Devices") disclose intrasaccular occlusion which are filled with liquid embolic material and expand to a pre-set shape. U.S. patent applications 20190282242 (Divino et al., Sep. 19, 2019, "Occlusive Devices") and 20190290286 (Divino et al., Sep. 26, 2019, "Occlusive Devices") disclose intrasaccular occlusion devices which are filled with liquid embolic material and expand to a pre-set shape. U.S. patent application 20190343532 (Divino et al., Nov. 14, 2019, "Occlusive Devices") discloses an intrasaccular device which changes from a compressed configuration to an expanded configuration with a unique shape or porosity profile.

U.S. patent Ser. No. 10/342,548 (Duncan, Jul. 9, 2019, "Occlusion Devices and Methods of Their Manufacture and Use") discloses a device with a lateral fringe on membranous material. U.S. patent application 20190362496 (Dutta et al., Nov. 28, 2019, "Isolation of Aneurysm and Parent Vessel in Volumetric Image Data") discloses a framework for isolating an aneurysm and a parent vessel in volumetric image data. U.S. patent application 20150216684 (Enzmann et al., Aug. 6, 2015, "Dual Rotational Stent Apparatus and Method for Endovascular Treatment of Aneurysms") discloses a coaxial stent system for aneurysm treatment. U.S. patent application 20190307460 (Ferrera et al., Oct. 10, 2019, "Intrasacular Occlusion Devices Methods Processes and Systems") discloses flexible aneurysm embolization devices made from laser cut nitinol. U.S. patent application 20200155333 (Franano et al., May 21, 2020, "Ballstent Device and Methods of Use") discloses a round, thin-walled, expandable metal structure made from gold, platinum, or silver. U.S. patent application 20200163784 (Franano et al., May 28, 2020, "Blockstent Device and Methods of Use") discloses a compressed, cylindrical or oblong, thin-walled, expandable stent for occluding a blood vessel segment.

U.S. patent application 20190223880 (Gerberding et al., Jul. 25, 2019, "Systems and Methods for Supporting or Occluding a Physiological Opening or Cavity") discloses a device with a distal-facing portion which occludes an aneurysm and a proximal-facing portion which arches over lumina of an artery. U.S. Pat. No. 5,334,210 (Gianturco, Aug. 2, 1994, "Vascular Occlusion Assembly") discloses an occlusion bag with an expanded diamond shape and an elongated flexible filler member. U.S. patent Ser. No. 10/939,915 (Gorochow et al., Mar. 9, 2021, "Aneurysm Device and Delivery System") discloses a braid for treating an aneurysm, wherein the braid has a distal end opposite a proximal end, and wherein translating the braid causes a delivery portion to expand and form a distal sack as well as invert into itself. U.S. patent Ser. No. 10/653,425 (Gorochow et al., May 19, 2020, "Layered Braided Aneurysm Treatment Device") discloses a tubular braid that is implanted in two distinct implanted shapes and a compaction-resistant column spanning the height of an aneurysm. U.S. patent Ser. No. 10/905,431 (Gorochow, Feb. 2, 2021, "Spiral Delivery System for Embolic Braid") discloses a braided implant with a spiral segment.

U.S. patent application 20190216467 (Goyal, Jul. 18, 2019, "Apparatus and Methods for Intravascular Treatment of Aneurysms") discloses an aneurysm neck bridge deployed in the parent vessel of the aneurysm. U.S. patent application 20180070955 (Greene et al., Mar. 15, 2018, "Embolic Containment") discloses systems to deliver liquid embolic material into an aneurysm. U.S. Pat. No. 6,346,117 (Greenhalgh, Feb. 12, 2002, "Bag for Use in the Intravascular Treatment of Saccular Aneurysms") and U.S. Pat. No. 6,391,037 (Greenhalgh, May 21, 2002, "Bag for Use in the Intravascular Treatment of Saccular Aneurysms") disclose a plurality of resilient filamentary members braided into a tubular sleeve with an opening to receive a clotting medium such as a platinum wire.

U.S. Pat. No. 9,592,363 (Griffin et al., Mar. 14, 2017, "Medical Device") discloses a device with a shaft having an elongated inner member and an elongated tubular reinforcing member disposed over at least a portion of the inner member. U.S. patent Ser. No. 10/130,372 (Griffin, Nov. 20, 2018, "Occlusion Device"), and U.S. patent applications 20150313605 (Griffin, Nov. 5, 2015, "Occlusion Device"), 20170156734 (Griffin, Jun. 8, 2017, "Occlusion Device"), 20190053810 (Griffin, Feb. 21, 2019, "Occlusion Device"), 20190059909 (Griffin, Feb. 28, 2019, "Occlusion Device") disclose an occlusive mesh with a circumferential fold line. U.S. patent application 20190269414 (Griffin, Sep. 5, 2019, "Occlusion Device") discloses an intrasaccular occlusion device with a plurality of coaxial expandable carriages. U.S. patent Ser. No. 10/869,672 (Griffin, Dec. 22, 2020, "Occlusion Device") discloses an occlusion device with a solid marker and a resilient mesh body attached within the marker. U.S. patent application 20200038035 (Griffin, Feb. 6, 2020, "Occlusion Device") discloses an occlusion device with a solid marker and a low profile resilient mesh body attached to the distal end of the marker. U.S. patent Ser. No. 10/285,711 (Griffin, May 14, 2019, "Occlusion Device") discloses an occlusion device with a continuous compressible mesh structure comprising axial mesh carriages configured end to end, wherein each end of each carriage is a pinch point in the continuous mesh structure.

U.S. patent Ser. No. 10/426,486 (Guo et al., Oct. 1, 2019, "Vaso-Occlusive Device Delivery System") discloses a vaso-occlusive device delivery system with a heat-activated pusher. U.S. patent application 20190262119 (Gupta et al., Aug. 29, 2019, "Delivery Device for Use with an Embolic Material") discloses an embolic material delivery assembly with an outer member having a lumen extending therein, a distal end region, and an inner member disposed within the lumen of the outer member. U.S. patent applications 20200187953 (Hamel et al., Jun. 18, 2020, "Devices, Systems, and Methods for the Treatment of Vascular Defects"), 20200187954 (Hamel et al., Jun. 18, 2020, "Devices, Systems, and Methods for the Treatment of Vascular Defects"), 20200197017 (Hamel et al., Jun. 25, 2020, "Devices, Systems, and Methods for the Treatment of Vascular Defects"), 20200197018 (Hamel et al., Jun. 25, 2020, "Devices, Systems, and Methods for the Treatment of Vascular Defects"), and 20200197020 (Hamel et al., Jun. 25, 2020, "Devices, Systems, and Methods for the Treatment of Vascular Defects") disclose a mesh which is deployed into a predetermined shape wherein: (a) the mesh is curved along its width, (b) the mesh is curved along its length, and (c) the mesh has an undulating contour across at least a portion of one or both of its length or its width. U.S. patent applications 20190209146 (Hebert et al., Jul. 11, 2019, "Micrograft for the Treatment of Intracranial Aneurysms and Method for Use"), 20190231328 (Hebert et al., Aug. 1, 2019, "Micrograft for the Treatment of Intracranial Aneurysms and Method for Use"), and 20190261967 (Hebert et al., Aug. 29, 2019, "Micrograft for the Treatment of Intracranial Aneurysms and Method for Use") disclose a micrograft with a series of peaks and valleys formed by crimping.

U.S. patent applications 20180206849 (Hewitt et al., Jul. 26, 2018, "Filamentary Devices for the Treatment of Vascular Defects") and 20170095254 (Hewitt et al., Apr. 6, 2017, "Filamentary Devices for Treatment of Vascular Defects") disclose a self-expanding globular shell which is inserted into an aneurysm sac. U.S. patent application 20190223881 (Hewitt et al., Jul. 25, 2019, "Devices for Therapeutic Vascular Procedures") discloses a self-expanding globular shell which is inserted into an aneurysm sac, wherein some shell filaments extend beyond the distal end of the shell. U.S. Pat. No. 9,955,976 (Hewitt et al., May 1, 2018, "Filamentary Devices for Treatment of Vascular Defects") discloses a self-expanding intrasaccular globular shell with areas with different size pores. U.S. patent application 20160249934 (Hewitt et al., Sep. 1, 2016, "Filamentary Devices for Treatment of Vascular Defects") discloses occlusive meshes with variable mesh density. U.S. patent application 20160249935 (Hewitt et al., Sep. 1, 2016, "Devices for Therapeutic Vascular Procedures") discloses an expandable cylindrical structure made of wires with a self-expanding permeable shell at the distal end of the cylindrical structure. U.S. patent application 20160367260 (Hewitt et al., Dec. 22, 2016, "Devices for Therapeutic Vascular Procedures") discloses an expandable cylindrical structure made of wires and a self-expanding permeable shell at the distal end of the cylindrical structure. U.S. patent application 20170128077 (Hewitt et al., May 11, 2017, "Devices for Therapeutic Vascular Procedures") discloses methods and devices for removing a thrombus. U.S. Pat. No. 9,492,174 (Hewitt et al., Nov. 15, 2016, "Filamentary Devices for Treatment of Vascular Defects") and Ser. No. 10/813,645 (Hewitt et al., Oct. 27, 2020, "Filamentary Devices for Treatment of Vascular Defects") disclose a resilient self-expanding permeable implant having a plurality of elongate filaments which are woven together. U.S. patent Ser. No. 10/939,914 (Hewitt et al., Mar. 9, 2021, "Filamentary Devices for the Treatment of Vascular Defects") discloses permeable shells made of woven braided mesh with variable mesh density. U.S. Pat. No. 9,629,635 (Hewitt et al., Apr. 25, 2017, "Devices for Therapeutic Vascular Procedures") discloses an expandable cylindrical structure made of wires and a self-expanding permeable shell located at the distal end of the cylindrical structure. U.S. Pat. No. 9,078,658 (Hewitt et al., Jul. 14, 2015, "Filamentary Devices for Treatment of Vascular Defects") discloses a self-expanding resilient permeable shell having an expanded state with a globular and longitudinally shortened configuration relative to a radially constrained state, and a plurality of elongate filaments which are woven together, which define a cavity of the permeable shell. U.S. patent application 20200289126 (Hewitt et al., Sep. 17, 2020, "Filamentary Devices for Treatment of Vascular Defects") discloses a permeable implant with a stiff proximal portion that is configured to sit at the neck of an aneurysm.

U.S. patent application 20010034531 (Ho et al., Oct. 25, 2001, "Bioactive Three Loop Coil") discloses an occlusion subassembly comprising a base section and a lateral protrusion fixedly attached to the base section. U.S. patent application 20050142163 (Hunter et al., Jun. 30, 2005, "Medical Implants and Fibrosis-Inducing Agents") discloses implants with fibrosis-inducing agents. U.S. patent application 20190247053 (Inouye, Aug. 15, 2019, "Occlusive Medical Device") discloses a neck bridge to occlude a heart appendage. U.S. patent application 20190298380 (Inouye et al., Oct. 3, 2019, "Occlusive Medical Device with Fixation Members") discloses a neck bridge to occlude a heart appendage. U.S. Pat. No. 6,530,934 (Jacobsen et al., Mar. 11, 2003, "Embolic Device Composed of a Linear Sequence of Miniature Beads") discloses an embolic device comprising a sequence of flexibly interconnected miniature beads. U.S. Pat. No. 6,585,748 (Jeffree, Jul. 1, 2003, "Device for Treating Aneurysms") discloses a permeable intrasaccular bag into which embolic coils are inserted.

U.S. patent Ser. No. 10/405,966 (Johnson, Sep. 10, 2019, "Implantable Intraluminal Device") discloses intraluminal stent graft devices whose walls include compliant channels which allow for fluid communication. U.S. Pat. No. 9,157,174 (Kusleika, Oct. 13, 2015, "Vascular Device for Aneurysm Treatment and Providing Blood Flow into a Perforator Vessel") and U.S. Pat. No. 9,561,122 (Kusleika, Feb. 7, 2017, "Vascular Device for Aneurysm Treatment and Providing Blood Flow into a Perforator Vessel") disclose occlusion devices with heat-set strands. U.S. patent application 20190133794 (Kusleika, May 9, 2019, "Methods and Systems for Increasing a Density of a Region of a Vascular Device") discloses a stent with elastic members and differential porosity. U.S. patent application 20150005807 (Lagodzki et al., Jan. 1, 2015, "Occlusion Device Including Bundle of Occlusion Wires Having Preformed Shapes") discloses an occlusion device with shape memory wires which expand to a preformed shape. U.S. patent application 20190216468 (Larsen et al., Jul. 18, 2019, "Occlusive Medical Device") discloses a neck bridge to occlude a heart appendage. U.S. patent application 20170354402 (Lee et al., Dec. 14, 2017, "Braided Medical Devices") discloses a vaso-occlusive member with helically-wound filaments.

U.S. patent application 20090318948 (Linder et al., Dec. 24, 2009, "Device, System and Method for Aneurysm Embolization") discloses dispensing embolic elements freely and randomly within an aneurysm cavity. U.S. patent Ser. No. 10/716,574 (Lorenzo et al., Jul. 21, 2020, "Aneurysm Device and Delivery Method") discloses a self-expanding braid with an outer occlusive sack and a segment which inverts into the outer occlusive sack like a tube sock. U.S. patent Ser. No. 10/905,430 (Lorenzo et al., Feb. 2, 2021, "Aneurysm Device and Delivery System") discloses a braid for treating an aneurysm with a radially-expandable segment which forms an outer occlusive sack and a second radially-expandable segment which forms an inner occlusive sack. U.S. patent application 20210007755 (Lorenzo et al., Jan. 14, 2021, "Intrasaccular Aneurysm Treatment Device With Varying Coatings") discloses an intrasaccular implant with an anti-thrombogenic coating. U.S. patent application 20190262123 (Mangiardi, Aug. 29, 2019, "Device and Method for Management of Aneurism, Perforation and Other Vascular Abnormalities") discloses a method for treating perforations, fistulas, ruptures, dehiscence and aneurysms.

U.S. patent application 20130245667 (Marchand et al., Sep. 19, 2013, "Filamentary Devices and Treatment of Vascular Defects") discloses a self-expanding globular shell which is inserted into an aneurysm sac. U.S. patent application 20160249937 (Marchand et al., Sep. 1, 2016, "Multiple Layer Filamentary Devices for Treatment of Vascular Defects") discloses a self-expanding multi-layer shell which is inserted into an aneurysm sac. U.S. patent application 20180000489 (Marchand et al., Jan. 4, 2018, "Filamentary Devices for Treatment of Vascular Defects") discloses a self-expanding globular shell which is inserted into an aneurysm sac. U.S. Pat. No. 9,597,087 (Marchand et al., Mar. 21, 2017, "Filamentary Devices for Treatment of Vascular Defects") discloses a permeable shell configured to occlude blood flow. U.S. patent Ser. No. 10/610,231 (Marchand et al., Apr. 7, 2020, "Filamentary Devices for Treatment of Vascular Defects") discloses a self-expanding resilient permeable shell having a plurality of elongate resilient filaments with a woven structure. U.S. patent application 20200281603 (Marchand et al., Sep. 10, 2020, "Filamentary Devices for Treatment of Vascular Defects") discloses a permeable shell with proximal ends of filaments are gathered by a proximal hub and the distal ends of each of the filaments are gathered by a distal hub.

U.S. patent application 20190254691 (Martin et al., Aug. 22, 2019, "Flexible Intravascular Treatment Devices and Associated Systems and Methods of Use") discloses stents with a plurality of cells and a plurality of joints between adjacent cells. U.S. patent application 20210052278 (Mauger, Feb. 25, 2021, "Vascular Occlusion Devices Utilizing Thin Film Nitinol Foils") discloses a deployable occlusion device for filling an aneurysm with a first end portion and a second end portion, wherein the first end portion is attached to a support structure and the second end portion of the mesh component is a free end. U.S. patent application 20190209181 (Mayer et al., Jul. 11, 2019, "Medical Device for Treating Vascular Malformations") discloses a helical device with a coilable section and a docking section. U.S. patent Ser. No. 10/595,875 (Mayer et al., Mar. 24, 2020, "Device for Restricting Blood Flow to Aneurysms") and U.S. patent application 20200163677 (Mayer et al., May 28, 2020, "Device for Restricting Blood Flow to Aneurysms") disclose a non-occlusive blood-restricting device with a sequence of loops having a gradually decreasing diameter.

U.S. patent application 20180271540 (Merritt et al., Sep. 27, 2018, "Systems and Methods for Embolization of Body Structures") discloses a self-expanding shell with lobes which is inserted into an aneurysm sac. U.S. patent Ser. No. 10/881,413 (Merritt et al., Jan. 5, 2021, "Systems and Methods for Embolization of Body Structures") discloses a self-expanding permeable shell with a plurality of circumferentially-arrayed lobes. U.S. patent application 20090112249 (Miles et al., Apr. 30, 2009, "Medical Device for Modification of Left Atrial Appendage and Related Systems and Methods") discloses collapsible and self-expanding devices to modify a left atrial appendage. U.S. patent application 20210007754 (Milhous et al., Jan. 14, 2021, "Filamentary Devices for Treatment of Vascular Defects") discloses a permeable implant having a radially constrained state configured for delivery within a catheter lumen, an expanded state, and a plurality of elongate filaments that are woven together. U.S. Pat. No. 9,687,245 (Molaei et al., Jun. 27, 2017, "Occlusive Devices and Methods of Use") discloses an occlusive device with a proximal end, a distal end, and a lumen extending between the proximal and distal ends, wherein proximal end has a self-expanding distal section and the distal section has a coil portion.

U.S. patent applications 20180263629 (Murphy et al., Sep. 20, 2018, "Vaso-Occlusive Device and Delivery Assembly") and 20190254676 (Murphy et al., Aug. 22, 2019, "Vaso-Occlusive Device and Delivery Assembly") disclose a vaso-occlusive treatment system with multi-layer wires. U.S. patent application 20160213380 (O'Brien, et al., Jul. 28, 2016, "Occlusion Device Having Spherical Secondary Shape and Mandrel for Forming Same") discloses a sphere made from helical memory wire. U.S. patent application 20190083075 (Onushko et al., Mar. 21, 2019, "Occlusive Medical Device with Sealing Member") disclose a neck bridge to occlude a heart appendage. U.S. patent application 20060149309 (Paul et al., Jul. 6, 2006, "Inverting Occlusion Devices, Methods, and Systems") discloses inverted vascular occlusion devices. U.S. patent application 20200367900 (Pedroso et al., Nov. 26, 2020, "Layered Braided Aneurysm Treatment Device With Corrugations") discloses an implant with an open end, a pinched end, and a predetermined shape.

U.S. patent application 20170258473 (Plaza et al., Sep. 14, 2017, "Systems and Methods for Delivery of Stents and Stent-Like Devices") discloses a self-expanding tubular structure which is inserted into the parent vessel of an aneurysm. U.S. patent application 20190046209 (Plaza et al., Feb. 14, 2019, "Delivery and Detachment Systems and Methods for Vascular Implants") discloses a system for delivering an implant device to a vascular site. U.S. patent applications 20060155323 (Porter et al., Jul. 13, 2006, "Intra-Aneurysm Devices") and 20190298379 (Porter et al., Oct. 3, 2019, "Intra-Aneurysm Devices") disclose an aneurysm occlusion device with an upper member in the dome and a lower member in the aneurysm neck. U.S. patent application 20210052279 (Porter et al., Feb. 25, 2021, "Intra-Aneurysm Devices") discloses an aneurysm occlusion device with an upper member that sits against the dome of the aneurysm, a lower member that sits in the neck of the aneurysm, and a means of adjusting the overall dimensions of the device. U.S. Pat. No. 4,638,803 (Rand, Jan. 27, 1987, "Medical Apparatus for Inducing Scar Tissue Formation in a Body") discloses a balloon coated with thrombosis-inducing material.

U.S. patent application 20200289124 (Rangwala et al., Sep. 17, 2020, "Filamentary Devices for Treatment of Vascular Defects") discloses a permeable implant with a stiffer proximal portion that is configured to sit at the neck of an aneurysm, wherein the stiffer proximal portion may include coils, stiffening elements, or reinforcement elements. U.S. patent application 20200038032 (Rhee et al., Feb. 6, 2020, "Occlusive Devices") discloses a frame and a mesh component coupled to the frame, wherein mesh component has a first porosity, and the frame has a second porosity. U.S. patent application 20190209178 (Richter et al., Jul. 11, 2019, "Aneurysm Closure Device") discloses occlusion of an aneurysm neck using a device with a plurality of self-expanding arms. U.S. patent applications 20140330299 (Rosenbluth et al., Nov. 6, 2014, "Embolic Occlusion Device and Method") discloses a self-expanding globular shell which is inserted into an aneurysm sac. U.S. patent application 20180303486 (Rosenbluth et al., Oct. 25, 2018, "Embolic Occlusion Device and Method") discloses a self-expanding globular shell which is inserted into an aneurysm sac plus a coil which extends out from the distal end of the shell. U.S. patent application 20160045201 (Rosenbluth et al., Feb. 18, 2016, "Blood Flow Disruption Devices and Methods for the Treatment of Vascular Defects") discloses a blood flow disruption device with a porous inner flow disruption element and a porous outer flow disruption element which coaxially surrounds the inner flow disruption element.

U.S. patent application 20090287294 (Rosqueta et al., Nov. 19, 2009, "Braid-Ball Embolic Devices") discloses "Goodness, Gracious, Great balls of wire!". U.S. patent application 20190059907 (Rosqueta et al., Feb. 28, 2019, "Devices, Systems, and Methods for the Treatment of Vascular Defects") discloses intrasaccular ribbons for aneurysm occlusion. U.S. patent Ser. No. 10/675,036 (Rosqueta et al., Jun. 9, 2020, "Devices, Systems, and Methods for the Treatment of Vascular Defects") and U.S. patent application 20200138447 (Rosqueta et al., May 7, 2020, "Devices, Systems, and Methods for the Treatment of Vascular Defects") disclose an occlusive device that includes a first mesh having an expanded state in which it curves about a first axis to form a first band, and a second mesh having an expanded state in which it curves about a second axis different than the first axis to form a second band. U.S. Pat. No. 6,350,270 (Roue, Feb. 26, 2002, "Aneurysm Liner") discloses an aneurysm liner with an extender inside the liner. U.S. patent application 20160022445 (Ruvalcaba et al., Jan. 28, 2016, "Occlusive Device"), patent application 20190343664 (Ruvalcaba et al., Nov. 14, 2019, "Occlusive Device"), and patent Ser. No. 10/736,758 (Ruvalcaba et al., Aug. 11, 2020, "Occlusive Device") disclose an aneurysm embolization device with a body having a single, continuous piece of material that is shape set into a plurality of distinct structural components.

U.S. Pat. No. 6,855,153 (Saadat, Feb. 15, 2005, "Embolic Balloon") and U.S. patent application 20020165572 (Saadat, Nov. 7, 2002, "Embolic Balloon") disclose an embolic balloon which aspirates blood while expanding. U.S. patent application 20110184451 (Sahl, Jul. 28, 2011, "Membrane Implant for Treatment of Cerebral Artery Aneurysms") discloses a cylindrical biocompatible plastic membrane used in combination with a stent. U.S. Pat. No. 5,041,090 (Scheglov et al., Aug. 20, 1991, "Occluding Device") discloses using nested balloons for occlusion. U.S. patent application 20020169473 (Sepetka et al., Nov. 14, 2002, "Devices and Methods for Treating Vascular Malformations") discloses occlusive devices with a primary coil and secondary windings. U.S. patent application 20080281350 (Sepetka et al., Nov. 13, 2008, "Aneurysm Occlusion Devices") discloses an (hourglass-shaped) occlusive device with a biocompatible matrix. U.S. patent application 20060116709 (Sepetka et al., Jun. 1, 2006, "Aneurysm Treatment Devices and Methods") discloses a device which expands within an aneurysm sac. U.S. Pat. No. 8,597,320 (Sepetka et al., Dec. 3, 2013, "Devices and Methods for Treating Vascular Malformations") discloses an occlusive device with a proximal collar and a distal collar. U.S. patent application 20190274691 (Sepetka et al., Sep. 12, 2019, "Occlusive Device") discloses a tubular braid that folds inward on itself for aneurysm occlusion.

U.S. patent Ser. No. 10/420,862 (Sharma et al., Sep. 24, 2019, "In-Situ Forming Foams for Treatment of Aneurysms") and U.S. patent application 20120265287 (Sharma et al., Oct. 18, 2012, "In-Situ Forming Foams for Treatment of Aneurysms") disclose the use of in-situ forming polymer foams to treat aneurysms. U.S. patent Ser. No. 10/729,447 (Shimizu et al., Aug. 4, 2020, "Devices for Vascular Occlusion") discloses an occlusive device, occlusive device delivery system, method of using, and method of delivering an occlusive device. U.S. patent application 20040254625 (Stephens et al., Dec. 16, 2004, "Inflatable Implant") discloses an implant that is inflated with filler materials. U.S. patent application 20190167272 (Stephens et al., Jun. 6, 2019, "Inflatable Implant") discloses an implant with a low profile when introduced into the body and a larger profile when it is inflated with one or more filler materials. U.S. Pat. No. 4,364,392 (Strother et al., Dec. 21, 1982, "Detachable Balloon Catheter") discloses a balloon into which a carrier liquid is pumped. U.S. patent application 20060167494 (Suddaby, Jul. 27, 2006, "Aneurysm Repair Method and Apparatus") discloses disks pressing against inner and outer sides of an aneurysm neck. U.S. patent application 20190201592 (Takahashi et al., Jul. 4, 2019, "Devices and Methods for Aneurysm Treatment") discloses ways to reduce susceptibility artifacts in MRA images.

U.S. patent application 20030028209 (Teoh et al., Feb. 6, 2003, "Expandable Body Cavity Liner Device") discloses an aneurysm liner for treating aneurysms of various shapes and sizes. U.S. patent application 20040098027 (Teoh et al., May 20, 2004, "Expandable Body Cavity Liner Device") discloses various aneurysm treatment devices ranging from ball stents to permeable liners. U.S. Pat. No. 7,153,323 (Teoh et al., Dec. 26, 2006, "Aneurysm Liner with Multi-Segment Extender") discloses an aneurysm liner with extender segments inside the liner. U.S. patent application 20170354418 (Teoh et al., Dec. 14, 2017, "Vaso-Occlusive Device Delivery System") discloses a vaso-occlusive device delivery system with a heat-activated pusher. U.S. Pat. No. 6,958,061 (Truckai et al., Oct. 25, 2005, "Microspheres with Sacrificial Coatings for Vaso-Occlusive Systems") discloses using a fluid to deliver microspheres for vascular occlusion. U.S. Pat. No. 4,341,218 (U, Jul. 27, 1982, "Detachable Balloon Catheter") discloses a balloon with a hollow cylinder fastened at the neck of the balloon. U.S. Pat. No. 5,935,148 (Villar et al., Aug. 10, 1999, "Detachable, Varying Flexibility, Aneurysm Neck Bridge") and U.S. Pat. No. 6,063,104 (Villar et al., May 16, 2000, "Detachable, Varying Flexibility, Aneurysm Neck Bridge") disclose an aneurysm neck bridge with varying flexibility. U.S. patent application 20190269533 (Vong et al., Sep. 5, 2019, "Stent and Stent Delivery Device") discloses a stent made from a single woven nitinol wire.

U.S. patent application 20110196413 (Wallace et al., Aug. 11, 2011, "System and Method for Retaining Vaso-Occlusive Devices within an Aneurysm") discloses an occlusive mesh made from a shape-memory alloy. U.S. patent applications 20170086851 (Wallace et al., Mar. 30, 2017, "Vaso-Occlusive Devices and Methods of Use") and 20190201000 (Wallace et al., Jul. 4, 2019, "Vaso-Occlusive Devices") disclose a vaso-occlusive delivery system with a pusher. U.S. patent Ser. No. 10/383,635 (Wallace et al., Aug. 20, 2019, "Vaso-Occlusive Devices and Methods of Use") and U.S. patent application 20180250013 (Wallace et al., Sep. 6, 2018, "Vaso-Occlusive Devices Including a Friction Element") disclose a vaso-occlusive system with a pusher to deliver soft embolic members. U.S. patent application 20200187952 (Walsh et al., Jun. 18, 2020, "Intrasaccular Flow Diverter for Treating Cerebral Aneurysms") discloses flow diverters with a stabilizing frame for anchoring the implant and an occluding element for diverting blood flow from the aneurysm neck. U.S. patent application 20210022765 (Walzman, Jan. 28, 2021, "Coated Endovascular Intrasaccular Occlusion Device") discloses an endovascular treatment mesh device with an amorphous hydrogel layer. U.S. patent Ser. No. 10/398,441 (Warner et al., Sep. 3, 2019, "Vascular Occlusion") discloses an aneurysm occlusion system which includes a containment bag, a pusher, and a stopper ring. U.S. patent application 20030212419 (West, Nov. 13, 2003, "Aneurysm Embolization Device and Deployment System") discloses an aneurysm embolization device with a headpiece and a plurality of spherical members.

U.S. Pat. No. 7,083,643 (Whalen et al., Aug. 1, 2006, "Methods for Treating Aneurysms") discloses filling an aneurysm sac with a fluid composition which solidifies in situ. U.S. patent Ser. No. 10/898,199 (Wilson et al., Jan. 26, 2021, "Expandable Implant and Implant System") discloses an expandable implant comprising a chain or linked sequence of expandable polymer foam elements. U.S. patent application 20200367897 (Wolfe et al., Nov. 26, 2020, "Systems and Methods for Treating Aneurysms") discloses an inverted mesh tube having an outer layer and an inner layer, wherein the outer layer transitions to the inner layer at an inversion fold. U.S. patent application 20210045750 (Wolf et al., Feb. 18, 2021, "Systems and Methods for Treating Aneurysms") discloses an implantable vaso-occlusive device including a proximal end configured to seat against the aneurysm adjacent the neck of the aneurysm and a distal end configured to extend in the sac and away from the neck of the aneurysm. U.S. patent application 20200367893 (Xu et al., Nov. 26, 2020, "Layered Braided Aneurysm Treatment Device") discloses an implant with two layers of tubular braid set into a predetermined shape. U.S. patent application 20200367896 (Zaidat et al., Nov. 26, 2020, "Systems and Methods for Treating Aneurysms") discloses an occlusion element with a first tubular mesh having a first end and a second end coupled together at a proximal end of the occlusion element, wherein an intermediate portion of the first tubular mesh includes a substantially 180 degree turn. U.S. patent Ser. No. 10/383,749 (Zhou et al., Aug. 20, 2019, "Stent and Method of Inserting a Stent into a Delivery Catheter") discloses a stent which is radially contractable from a fully radially expanded state to a radially contracted state via elongation of the frame.

SUMMARY OF THE INVENTION

Disclosed herein is an intrasacular aneurysm occlusion device with a neck bridge with a closeable opening through which embolic material is inserted through the neck bridge into an aneurysm sac. After the neck bridge has been inserted and expanded within the aneurysm sac, a catheter is inserted through the opening and embolic material is delivered through the catheter into the aneurysm sac. After the aneurysm sac has been filled with embolic material, the catheter is then withdrawn and the opening is closed so that embolic material does not escape out of the aneurysm sac. In example, the shape of the neck bridge can be ellipsoidal, spherical, bowl-shaped, or toroidal. In an example, the opening can be remotely closed by the operator of the device. This device can occlude irregularly-shaped and different-size aneurysms better than intrasacular devices which expand to a pre-defined overall shape and can be more stable than a neck bridge alone.

BRIEF INTRODUCTION TO THE FIGURES

FIG. 1 shows a parent-vessel aneurysm occlusion device wherein electromagnetic energy moves a planar mesh to one side of a tubular mesh.

FIG. 2 shows a parent-vessel aneurysm occlusion device wherein inflation of a balloon pushes a planar mesh to one side of a tubular mesh.

FIG. 3 shows a parent-vessel aneurysm occlusion device wherein a partial-cylindrical mesh is rotated to one side of a tubular mesh.

FIG. 4 shows a parent-vessel aneurysm occlusion device wherein a partial-cylindrical mesh is removed from a tubular mesh.

FIG. 5 shows a parent-vessel aneurysm occlusion device with a low-porosity helical strip.

FIG. 6 shows a parent-vessel aneurysm occlusion device wherein application of electromagnetic energy causes wires, struts, or bands to partially detach from a tubular mesh.

FIG. 21 shows an intrasacular aneurysm occlusion device with a valve in a half-torus mesh through which embolic members are inserted.

FIG. 22 shows an intrasacular aneurysm occlusion device with a valve in toriodal mesh through which embolic members are inserted.

FIG. 23 shows an intrasacular aneurysm occlusion device with a valve in bowl-shaped mesh through which embolic members are inserted.

FIG. 24 shows an intrasacular aneurysm occlusion device with a valve in hyperbolic-shaped (e.g. hourglass shaped) mesh through which embolic members are inserted.

FIG. 25 shows an intrasacular aneurysm occlusion device with an inner convex mesh, an outer convex mesh, and a valve in the outer convex mesh through which embolic members are inserted.

FIG. 26 shows an intrasacular aneurysm occlusion device with a metal mesh, a polymer net around the metal mesh, and a valve in the polymer net through which embolic members are inserted.

FIG. 51 shows an intrasacular aneurysm occlusion device with nested proximal and distal umbrella-shaped meshes.

FIG. 52 shows an intrasacular aneurysm occlusion device with a proximal bowl-shaped mesh and a distal umbrella-shaped mesh which overlap.

FIG. 53 shows an intrasacular aneurysm occlusion device with nested proximal and distal bowl-shaped meshes.

FIG. 54 shows an intrasacular aneurysm occlusion device with a plurality of embolic masses which slide along a wire.

Figure 55:
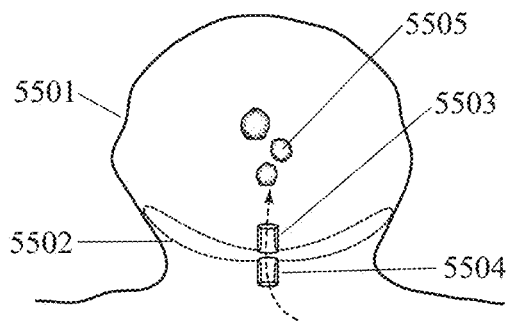

FIG. 55 shows an intrasacular aneurysm occlusion device comprising: a bowl-shaped mesh through which coils are inserted into an aneurysm sac, wherein the bowl is formed by pinching the ends of a tubular mesh and then moving these ends together; a distal-facing lumen within which the distal end of the tubular mesh is pinched; and a proximal-facing lumen within which the proximal end of the tubular mesh is pinched.

Figure 56:
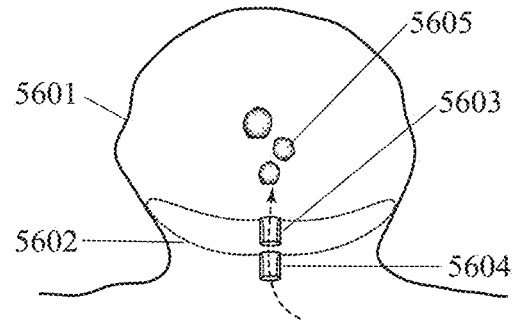

FIG. 56 shows an intrasacular aneurysm occlusion device comprising: a bowl-shaped mesh through which coils are inserted into an aneurysm sac, wherein the bowl is formed by pinching the ends of a tubular mesh and then moving these ends together; a proximal-facing lumen within which the distal end of the tubular mesh is pinched; and a proximal-facing lumen within which the proximal end of the tubular mesh is pinched.

Figure 57:
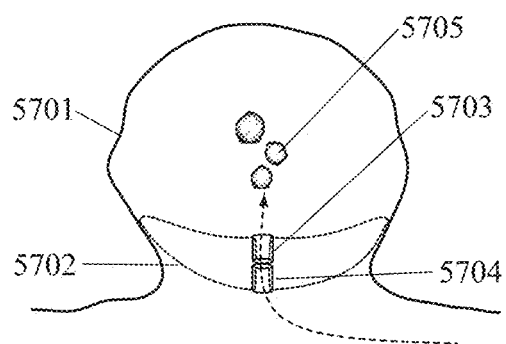

FIG. 57 shows an intrasacular aneurysm occlusion device comprising: a bowl-shaped mesh through which coils are inserted into an aneurysm sac, wherein the bowl is formed by pinching the ends of a tubular mesh and then moving these ends together; a proximal-facing lumen within which the distal end of the tubular mesh is pinched; and a distal-facing lumen within which the proximal end of the tubular mesh is pinched.

Figure 58:
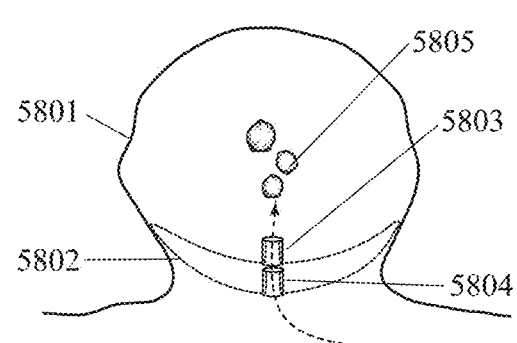

FIG. 58 shows an intrasacular aneurysm occlusion device comprising: a bowl-shaped mesh through which coils are inserted into an aneurysm sac, wherein the bowl is formed by pinching the ends of a tubular mesh and then moving these ends together; a distal-facing lumen within which the distal end of the tubular mesh is pinched; and a distal-facing lumen within which the proximal end of the tubular mesh is pinched.

Figure 59:
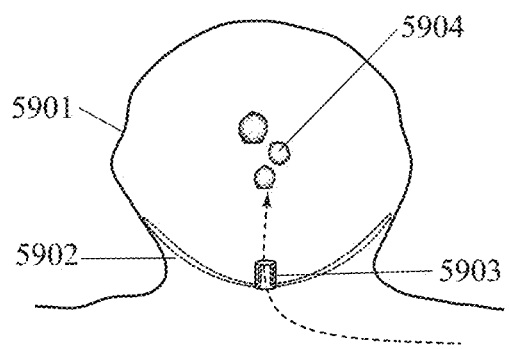

FIG. 59 shows an intrasacular aneurysm occlusion device comprising: a bowl-shaped mesh through which coils are inserted into an aneurysm sac, wherein the bowl is formed by pinching the ends of a tubular mesh and then moving these ends together; a distal-facing lumen within which the proximal and distal ends of the tubular mesh are pinched.

Figure 60:
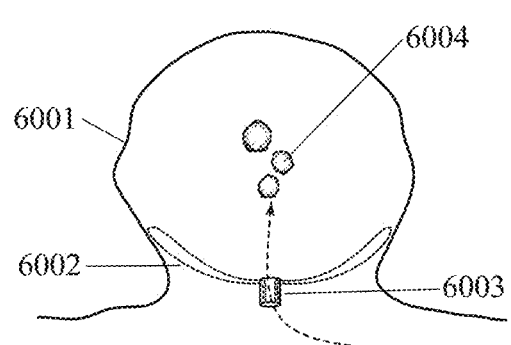

FIG. 60 shows an intrasacular aneurysm occlusion device comprising: a bowl-shaped mesh through which coils are inserted into an aneurysm sac, wherein the bowl is formed by pinching the ends of a tubular mesh and then moving these ends together; a proximal-facing lumen within which the proximal and distal ends of the tubular mesh are pinched.

Figure 61:
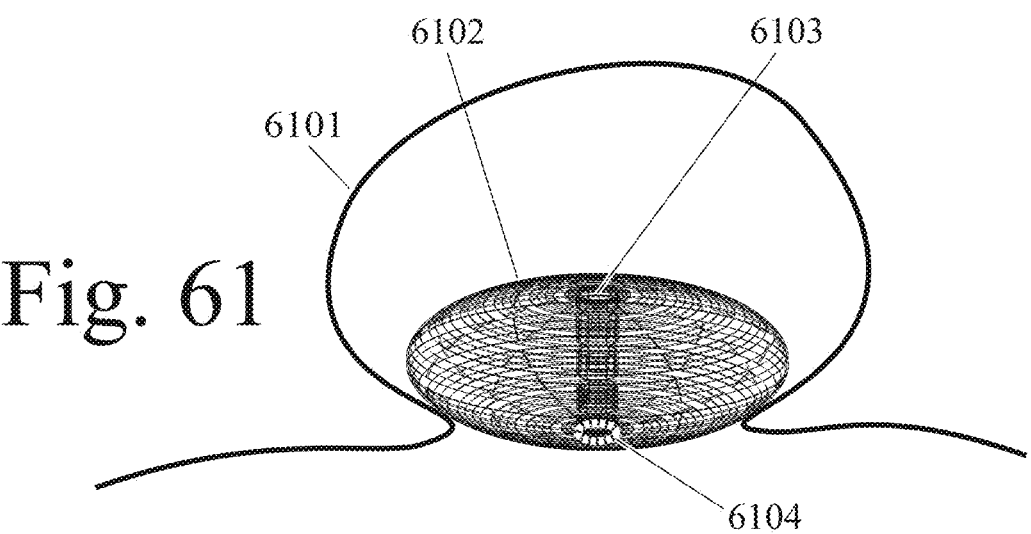

FIG. 61 shows an ellipsoidal neck bridge with a central closeable opening or lumen through which embolic material is inserted into an aneurysm sac.

Figure 62:
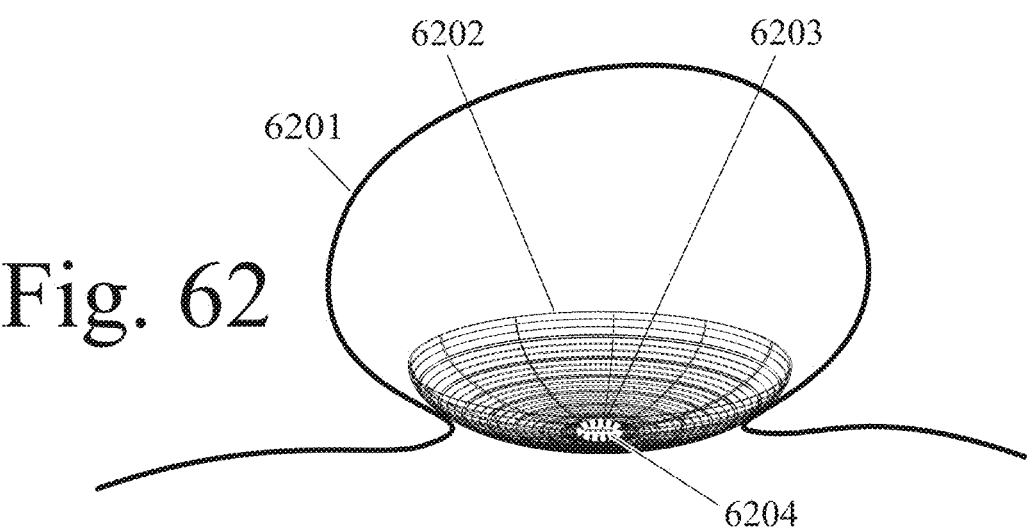

FIG. 62 shows a bowl-shaped neck bridge with a central closeable opening or lumen through which embolic material is inserted into an aneurysm sac.

Figure 63:
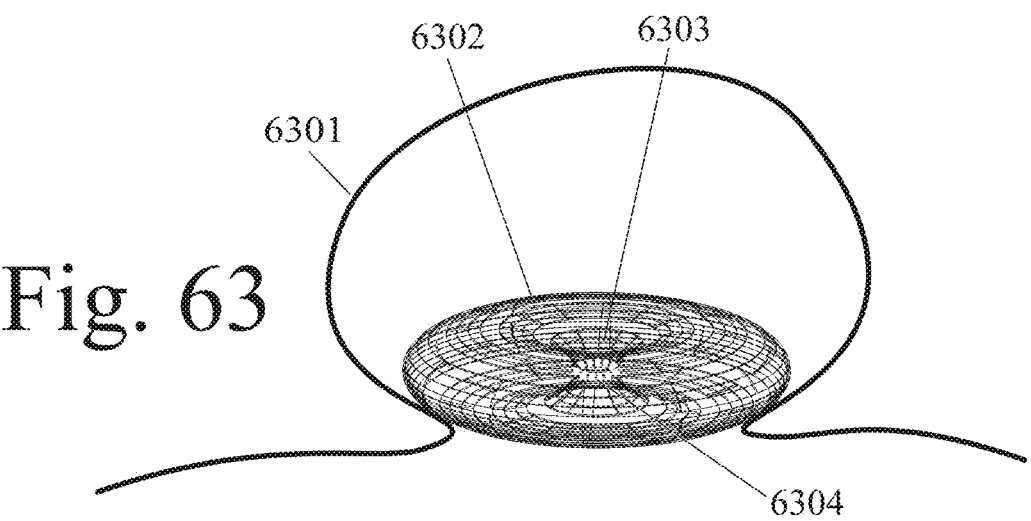

FIG. 63 shows a toroidal neck bridge with a central closeable opening or lumen through which embolic material is inserted into an aneurysm sac.

Figure 64:
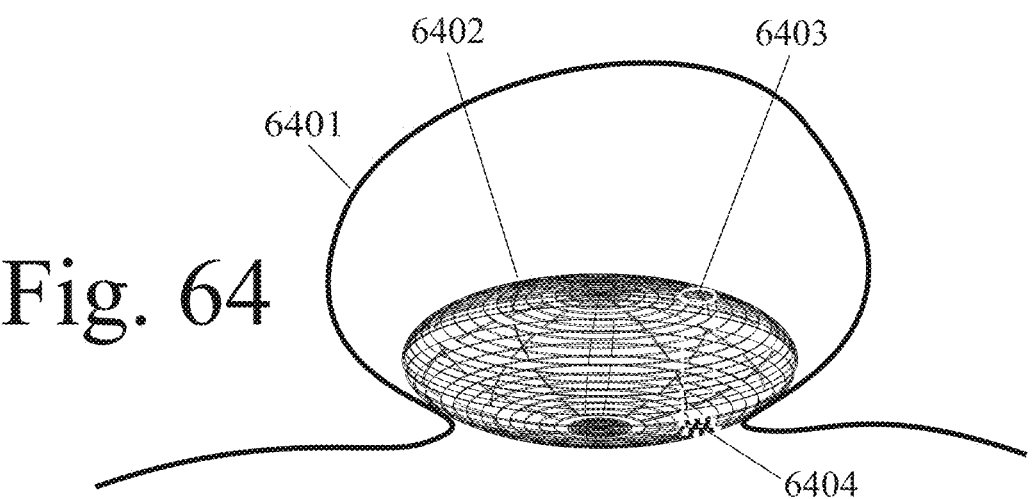

FIG. 64 shows an ellipsoidal neck bridge with an off-center closeable opening or lumen through which embolic material is inserted into an aneurysm sac.

Figure 65:
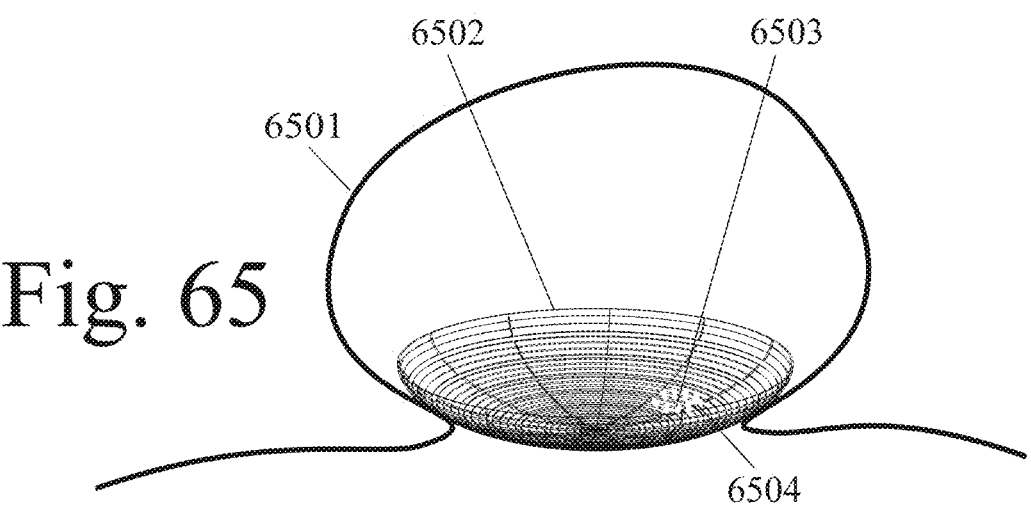

FIG. 65 shows a bowl-shaped neck bridge with an off-center closeable opening or lumen through which embolic material is inserted into an aneurysm sac.

Figure 66:
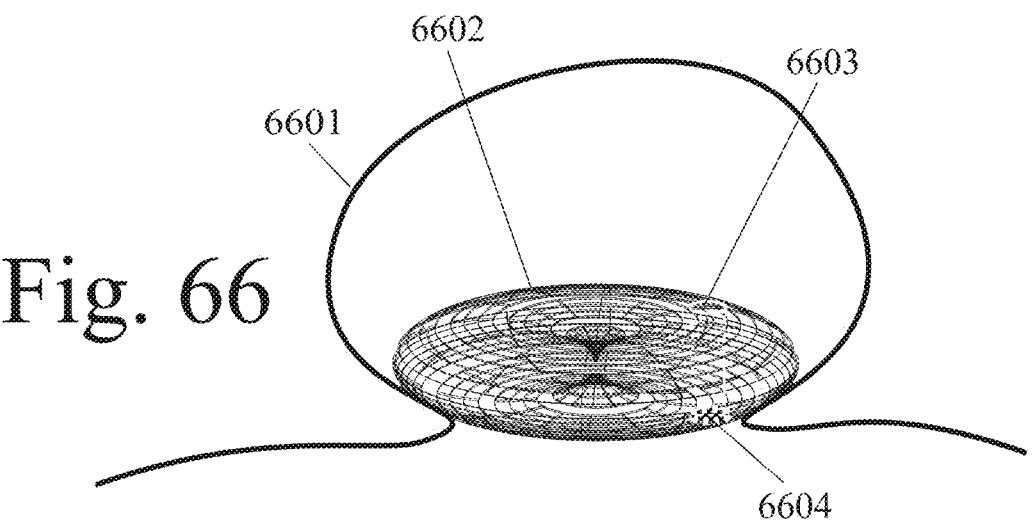

FIG. 66 shows a toroidal neck bridge with an off-center closeable opening or lumen through which embolic material is inserted into an aneurysm sac.

DETAILED DESCRIPTION OF THE FIGURES

FIG. 1 shows two sequential views of an example of a device for occluding a cerebral aneurysm comprising: a tubular mesh 101 which is configured to be inserted into the parent blood vessel of an aneurysm and span the aneurysm neck; a planar mesh 102 in the interior cavity of the tubular mesh; and an electromagnetic energy emitter 103, wherein transmission of electromagnetic energy from the emitter to the planar mesh causes the planar mesh to move (e.g. bend, curve, shift, and/or expand) toward a selected portion of the circumferential perimeter (e.g. toward a selected side) of the tubular mesh which is closest to the aneurysm neck. This selectively decreases the porosity of the portion of the device which is closest to the aneurysm neck. The upper half of FIG. 1 shows this device at a first point in time before electromagnetic energy has been applied to the planar mesh. The lower half of FIG. 1 shows this device at a second point in time after electromagnetic energy has been applied to the planar mesh and caused the planar mesh to curve toward a selected portion (e.g. a selected side) of the tubular mesh.

In an example, a tubular mesh can be cylindrical. In an example, a tubular mesh can be a metal stent. In an example, a tubular mesh can be a polymer stent. In an example, a tubular mesh can be cut, braided, or 3D printed. In an example, a tubular mesh can be an expandable wire frame. In an example, a tubular mesh can self-expand when released from a catheter. In an example, a tubular mesh can further comprise radio-opaque sections or markers. In an example, a planar mesh can be centrally located within the interior cavity of a tubular mesh. In an example, a planar mesh can span a central diameter of the interior cavity of a tubular mesh. In an example, the sides of a planar mesh can be attached to the interior surface of a tubular mesh. In an example, the porosity of a planar mesh can be lower than the porosity of a tubular mesh. In an example, a planar mesh can be radio-opaque. In an example, a planar mesh can comprise a polymer mesh on a wire frame.

In an example, a planar mesh can be made from shape memory material whose configuration is changed by the application of electromagnetic energy. In an example, a central portion of a planar mesh can move (e.g. bend, curve, and/or expand) toward a selected side of the tubular mesh when electromagnetic energy is applied. In an example, the direction in which a planar mesh moves can be selected (remotely) by a device operator after the device has been positioned within the parent blood vessel of an aneurysm. In an example, an electromagnetic energy emitter can be located and/or controlled by the operator from a location external to a person's body. In an example, an electromagnetic energy emitter can be in electromagnetic communication with the planar mesh via a wire. In an example, the planar mesh can be curved in a convex manner by application of a first pattern of electromagnetic energy or curved in a concave manner by application of a second pattern of electromagnetic energy, wherein the pattern of electromagnetic energy is selected by a device operator.

In an example, a planar mesh can have a first (generally flat) configuration in which it is centrally located within a tubular mesh and a second (arcuate) configuration in which it has been moved (e.g. bent, curved, and/or expanded) toward the side of the tubular mesh which is closest to the aneurysm neck. In an example, a planar mesh can be moved from its first configuration to its second configuration by the application of electromagnetic energy. In an example, a planar mesh can substantially overlap, span, and/or conform to a selected side of a tubular mesh when the planar mesh is in its second configuration. In an example, a planar mesh can have a quarter-cylinder shape in its second configuration. In an example, a planar mesh can overlap, span, and/or conform to between 20% and 40% of the circumferential perimeter of a tubular mesh when the planar mesh is in its second configuration. In an example, a planar mesh can have a half-cylinder shape in its second configuration. In an example, a planar mesh can overlap, span, and/or conform to between 33% and 66% of the circumferential perimeter of a tubular mesh when the planar mesh is in its second configuration.

In the example shown in FIG. 1, a device includes a tubular mesh and a single interior mesh in the interior cavity of the tubular mesh. In a variation on this example, a device can include a tubular mesh and a plurality of interior meshes in the interior cavity of the tubular mesh. In an example, one or more of a plurality of interior meshes can be selected to be moved by a device operator. In an example, one or more selected interior meshes can be moved by a device operator toward the side of the device which is closest to the aneurysm after the device has been inserted into in the parent blood vessel. In an example, the concavity and/or convexity of one or more interior meshes can be selectively and remotely adjusted by a device operator after the device has been inserted into a parent blood vessel so as to decrease the porosity of the side of the device which is closest to an aneurysm neck.

FIG. 2 shows two sequential views of an example of a device for occluding a cerebral aneurysm comprising: a tubular mesh 201 which is configured to be inserted into the parent blood vessel of an aneurysm and to span the aneurysm neck; a planar mesh 202 in the interior cavity of the tubular mesh; a first longitudinal balloon 203 between a first side of the planar mesh and the tubular mesh; and a second longitudinal balloon 204 between a second side of the planar mesh and the tubular mesh, wherein inflation of the second longitudinal balloon pushes the planar mesh toward a selected portion of the circumferential perimeter (e.g. toward a selected side) of the tubular mesh which is closest to the aneurysm neck. This selectively decreases the porosity of the portion of the device which is closest to the aneurysm neck. The upper half of FIG. 2 shows this device at a first point in time before the second balloon has been inflated. The lower half of FIG. 2 shows this device at a second point in time after the first balloon has been removed and the second balloon has been inflated. After this, the second balloon is deflated and also removed.

In an example, a tubular mesh can be cylindrical. In an example, a tubular mesh can be a metal stent. In an example, a tubular mesh can be a polymer stent. In an example, a tubular mesh can be cut, braided, or 3D printed. In an example, a tubular mesh can be an expandable wire frame. In an example, a tubular mesh can self-expand when released from a catheter. In an example, a tubular mesh can further comprise radio-opaque sections or markers. In an example, a planar mesh can be centrally located within the interior cavity of a tubular mesh. In an example, a planar mesh can span a central diameter of the interior cavity of a tubular mesh. In an example, the side of a planar mesh can be attached to the interior of the tubular mesh. In an example, the porosity of the planar mesh can be lower than the porosity of the tubular mesh. In an example, a planar mesh can be radio-opaque. In an example, a planar mesh can comprise a polymer mesh on a wire frame.

In an example, a central portion of a planar mesh can be pushed (e.g. bent, curved, and/or expanded) toward a selected side of the tubular mesh when the balloon closer to the aneurysm neck is removed and the balloon farther from the aneurysm neck is inflated. In an example, a planar mesh can have a first configuration in which it is centrally located within the tubular mesh and a second configuration in which it curves toward the side of the tubular mesh which is closest to the aneurysm neck. In an example, a planar mesh can be moved from its first configuration to its second configuration by removal of one balloon and inflation of the other balloon.

In an example, a planar mesh can substantially overlap, span, and/or conform to a selected side of a tubular mesh when the planar mesh is in its second configuration. In an example, a planar mesh can overlap, span, and/or conform to between 20% and 40% of the circumferential perimeter of a tubular mesh when the planar mesh is in its second configuration. In an example, a planar mesh can overlap, span, and/or conform to between 33% and 66% of the circumferential perimeter of a tubular mesh when the planar mesh is in its second configuration. In an example, a planar mesh can be substantially flat in its first configuration and can be a section of a cylinder (e.g. a half cylinder) in its second configuration.

FIG. 3 shows two sequential views of an example of a device for occluding a cerebral aneurysm comprising: a cylindrical mesh 301 which is configured to be inserted into the parent blood vessel of an aneurysm and to span the aneurysm neck; a partial-cylindrical mesh 302 inside the cylindrical mesh, wherein the partial-cylindrical mesh can be rotated relative to the cylindrical mesh, wherein a first portion of the circumferential perimeter of the device where the partial cylindrical mesh and the cylindrical mesh overlap has a first porosity level, wherein a second portion of the circumferential perimeter of the device where the partial cylindrical mesh and the cylindrical mesh do not overlap has a second porosity level, wherein the second porosity level is less than the first porosity level, and wherein the partial-cylindrical mesh is rotated after insertion of the device into the parent blood vessel so that the first portion is closer to the aneurysm neck than the second portion. The upper half of FIG. 3 shows this device at a first point in time before the partial-cylindrical mesh has been rotated. The lower half of FIG. 3 shows this device at a second point in time after the partial-cylindrical mesh has been rotated.

In an example, a cylindrical mesh can be a metal stent. In an example, a cylindrical mesh can be a polymer stent. In an example, a cylindrical mesh can be cut, braided, or 3D printed. In an example, a cylindrical mesh can be an expandable wire frame. In an example, a cylindrical mesh can self-expand when released from a catheter. In an example, a cylindrical mesh can further comprise radio-opaque sections or marker. In an example, the porosity of the partial-cylindrical planar mesh can be lower than the porosity of the cylindrical mesh. In an example, the partial-cylindrical planar mesh can comprise a polymer mesh on a wire frame. In an example, a partial-cylindrical mesh can be radio-opaque. In an example, a partial-cylindrical mesh can be a quarter cylinder. In an example, a partial-cylindrical mesh can overlap between 20% and 40% of the circumferential perimeter of the cylindrical mesh. In an example, a partial-cylindrical mesh can be a half cylinder. In an example, the partial-cylindrical mesh can overlap between 33% and 66% of the circumferential perimeter of the cylindrical mesh.

In an example, rotation of a partial-cylindrical mesh can be remotely controlled by a device operator from a location external to a person's body. In an example, a partial-cylindrical mesh can be rotated by a device operator by rotating a catheter and/or guide wire. In an example, this device can further comprise an electromagnetic actuator which rotates the partial-cylindrical mesh relative to the cylindrical mesh, wherein this actuator is remotely controlled by the device operator.

FIG. 4 shows two sequential views of an example of a device for occluding a cerebral aneurysm comprising: an outer cylindrical mesh 401 which is configured to be inserted into the parent blood vessel of an aneurysm and span the aneurysm neck; an inner cylindrical mesh 403 which is inside the outer cylindrical mesh; a first partial-cylindrical mesh 402 (e.g. a half-cylinder mesh or quarter-cylinder mesh) which is between the outer cylindrical mesh and the inner cylindrical mesh; and a second partial-cylindrical mesh 403 (e.g. a half-cylinder mesh or quarter-cylinder mesh) which is between the outer cylindrical mesh and the inner cylindrical mesh, wherein the first partial-cylindrical is closer to the aneurysm neck than the second partial-cylindrical mesh, and wherein the second partial-cylindrical mesh is removed from the device after the device has been inserted into the parent blood vessel. This causes the side of the device which is closer to the aneurysm neck to have a lower porosity than the side of the device which is farther from the aneurysm neck. The upper half of FIG. 4 shows this device at a first point in time before the second partial-cylindrical mesh has been removed from the device. The lower half of FIG. 4 shows this device at a second point in time after the second partial-cylindrical mesh has been removed from the device.

In an example, an outer and/or inner cylindrical mesh can be made from metal. In an example, an outer and/or inner cylindrical mesh can be made from a polymer. In an example, an outer and/or inner cylindrical mesh can be cut, braided, or 3D printed. In an example, an outer and/or inner cylindrical mesh can be an expandable wire frame. In an example, an outer and/or inner cylindrical mesh can self-expand when released from a catheter. In an example, an outer and/or inner cylindrical mesh can further comprise radio-opaque sections or markers. In an example, the porosity of a partial-cylindrical mesh can be lower than the porosity of an outer and/or inner cylindrical mesh. In an example, a partial-cylindrical mesh can be radio-opaque. In an example, a partial-cylindrical mesh can comprise a polymer mesh on a wire frame. In an example, a partial-cylindrical mesh can be a half cylinder. In an example, a partial-cylindrical mesh can overlap between 33% and 66% of the circumferential perimeter of the outer cylindrical mesh. In an example, a partial-cylindrical mesh can be a quarter cylinder. In an example, a partial-cylindrical mesh can overlap between 20% and 40% of the circumferential perimeter of the outer cylindrical mesh.

In an example, one or more of a plurality of partial-cylindrical meshes can be selected, detached, and removed from the device by a device operator after the device has been inserted into a parent blood vessel. In an example, a device operator can select which partial-cylindrical meshes to remove by observing, via medical imaging, which are farthest from the aneurysm neck after insertion of the device into the parent blood vessel. In an example, a device operator can detach selected partial-cylindrical meshes by applying electromagnetic energy to them, thereby melting connections between the partial-cylindrical meshes and the outer and/or inner cylindrical meshes. In an example, selected partial-cylindrical meshes can then be removed by sliding them out from between the outer and inner cylindrical meshes.

In an example, a device for occluding a cerebral aneurysm can comprise: an outer cylindrical mesh which is configured to be inserted into the parent blood vessel of an aneurysm and span the aneurysm neck; an inner cylindrical mesh which is inside the outer cylindrical mesh; and a plurality of longitudinal strips between the outer cylindrical mesh and the inner cylindrical mesh. In an example, a first set of longitudinal strips is closer to the aneurysm neck than a second set of longitudinal strips. In an example, the second set of longitudinal strips can be removed from the device after the device has been inserted into the parent blood vessel. In an example, a second set of longitudinal strips can be selected by the device operator based on medical imaging. In an example, a second set of longitudinal strips can be removed from the device and from the person's body by a device operator. This leaves the device with lower porosity along the side which is closest to the aneurysm neck.

FIG. 5 shows two sequential views of an example of a device for occluding a cerebral aneurysm comprising: a tubular mesh 503 which is configured to be inserted into a parent blood vessel, wherein the parent blood vessel has an aneurysm 501 and one or more branching vessels 502, wherein the tubular mesh further comprises at least one low-porosity helical strip 504 whose porosity is lower than the average porosity of the tubular mesh, wherein the tubular mesh is configured to be moved so that the helical strip spans at least a portion of the aneurysm neck but does not span the entrance to the one or more branching vessels. The upper half of FIG. 5 shows this device at a first point in time before it has been moved so that the helical strip spans the aneurysm neck. The lower half of FIG. 5 shows this device at a second point in time after it has been moved so that the helical strip does span the aneurysm neck.

In this example, a device includes a double helix (with two low-porosity helical strips). In an example, a device can have just one low-porosity helical strip. In an example, a device can be moved longitudinally in order to align a low-porosity helical strip with an aneurysm neck (and misalign the strip with the entrances to one or more branching vessels). In a variation on this example, a device can have a longitudinal series of low-porosity rings or bands, wherein the device can be moved longitudinally in order to align a low-porosity ring or band with an aneurysm neck (and misalign low-porosity rings or bands with the entrances to one or more branching vessels).

In an example, a device can be rotated in order to align a low-porosity helical strip with an aneurysm neck (and misalign the strip with the entrances to one or more branching vessels). In an example, rotation of the device can be remotely controlled by a device operator from a location external to a person's body. In an example, the device can be rotated by a device operator by rotating a catheter and/or guide wire. In an example, this device can further comprise an electromagnetic actuator which rotates the low-porosity helical strip, wherein this actuator is remotely controlled by the device operator.

FIG. 6 shows two sequential views of an example of a device for occluding a cerebral aneurysm comprising: a tubular mesh (601) which is configured to be inserted into the parent blood vessel of an aneurysm, a first longitudinal series of wires, struts, and/or bands (including 602), and a second longitudinal series of wires, struts, and/or bands (including 603), wherein the second longitudinal series of wires, struts, and/or bands is connected to the tubular mesh by a plurality of connections (including 604 and 605), and wherein application of electromagnetic energy to selected connections causes a selected sub-set of the second longitudinal series of wires, struts, or bands to at least partially detach from the tubular mesh and to contract over the portion of the tubular mesh which is configured to be closest to the aneurysm neck, thereby decreasing the porosity of portion of the tubular mesh which spans the aneurysm neck.

The upper half of FIG. 6 shows this device at a first point in time, before electromagnetic energy has been applied to selected connections and a selected sub-set of the second longitudinal series of wires, struts, or bands has partially detached from the tubular mesh and contracted over a side of the tubular mesh. The lower half of FIG. 6 shows this device at a second point in time, after electromagnetic energy has been applied to selected connections and a selected sub-set of the second longitudinal series of wires, struts, or bands has partially detached from the tubular mesh and contracted over a side of the tubular mesh.

In an example, a tubular mesh can be cylindrical. In an example, a tubular mesh can be a metal stent. In an example, a tubular mesh can be a polymer stent. In an example, a tubular mesh can be a cut, braided, or 3D printed. In an example, a tubular mesh can be an expandable wire frame. In an example, a tubular mesh can self-expand when released from a catheter. In an example, a tubular mesh can further comprise radio-opaque sections or markers. In an example, wires, struts, and/or bands in a second longitudinal series of wires, struts, and/or bands can be undulating, sinusoidal, and/or serpentine. In an example, undulations of a wire, strut, and/or band can be closer together after the wire, strut, and/or band has been (partially) detached and contracted. In an example, a wire, strut, and/or band can be made from a shape memory material so that the wire, strut, and/or band self-contracts when it is (partially) detached from a tubular mesh. In an example, a tubular mesh can have inner and outer layers. In an example, wires, struts, and/or bands in a second longitudinal series can move (e.g. slide and contract) between these inner and outer layers.

In an example, wires, struts, and/or bands in a second longitudinal series of wires, struts, and/or bands can have a first configuration in which they span the entire circumference of a tubular mesh. In an example, selected wires, struts, and/or bands in a second longitudinal series of wires, struts, and/or bands can have a second (contracted) configuration in which they span only a portion of the circumference of a tubular mesh. In an example, selected wires, struts, and/or bands in a second longitudinal series of wires, struts, and/or bands can span between 20% and 40% of the circumference of a tubular mesh in their second (contracted) configuration. In an example, selected wires, struts, and/or bands in a second longitudinal series of wires, struts, and/or bands can span between 33% and 66% of the circumference of a tubular mesh in their second (contracted) configuration.

In an example, selected wires, struts, and/or bands in a second longitudinal series of circumferential wires, struts, and/or bands can be changed from their first configurations to their second configurations by selectively (partially) detaching them from the tubular mesh. In an example, they can be selectively detached from the tubular mesh by selectively melting the connections between them and the tubular mesh by the selective application of electromagnetic energy. In an example, a device operator can selectively decrease the porosity of the side of the device closest to the aneurysm neck by selectively melting connections of circumferential wires, struts, and/or bands on the side farthest from the aneurysm neck. In an example, selected wires, struts, and/or bands in a second longitudinal series of circumferential wires, struts, and/or bands can be made from shape memory material, wherein they are changed from their first configurations by first (partially) detaching them from the tubular mesh and then applying electromagnetic energy which contracts them.

Figure 7:
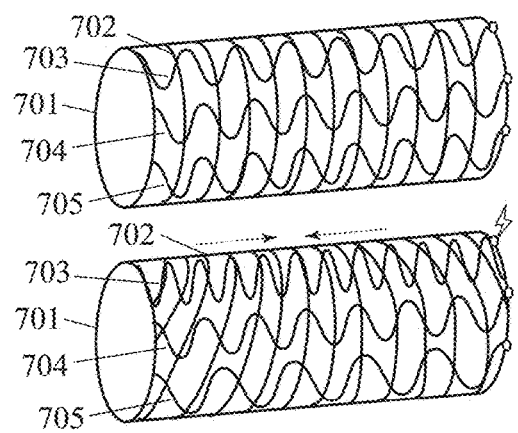
FIG. 7 shows a parent-vessel aneurysm occlusion device with undulating, contracting longitudinal wires (or bands).

FIG. 7 shows two sequential views of an example of a device for occluding a cerebral aneurysm comprising: a tubular mesh 701 which is configured to be inserted into the parent blood vessel of an aneurysm; a longitudinal series of circumferential wires (or bands) including 702; and a plurality of undulating longitudinal wires (or bands) including 703, 704, and 705, wherein the plurality of undulating longitudinal wires have a first configuration in which undulations of different wires have the same inter-undulation distance, wherein the plurality of undulating longitudinal wires have a second configuration in which undulations of different wires have different inter-undulation distances, and wherein the plurality of undulating longitudinal wires are changed from their first configuration to their second configuration by the application of electromagnetic energy to a selected subset of the plurality of undulating longitudinal wires. The upper half of FIG. 7 shows this device at a first point in time before electromagnetic energy has been applied to a selected subset of the plurality of undulating longitudinal wires. The lower half of FIG. 7 shows this device at a second point in time after electromagnetic energy has been applied to a selected subset of the plurality of undulating longitudinal wires, thereby reducing the porosity of the side of the device which is closest to the aneurysm neck.

In an example, a device operator can selectively reduce the distances between undulations in one or more undulating longitudinal wires on a side of the device which is closest to the aneurysm neck in order to decrease the porosity of the side of the device which is closest to the aneurysm neck. In an example, a tubular mesh can be cylindrical. In an example, a tubular mesh can be a metal stent. In an example, a tubular mesh can be a polymer stent. In an example, a tubular mesh can be a cut, braided, or 3D printed. In an example, a tubular mesh can be an expandable wire frame. In an example, a tubular mesh can self-expand when released from a catheter. In an example, a tubular mesh can further comprise radio-opaque sections or markers. In an example, undulating longitudinal wires can be sinusoidal and/or serpentine. In an example, undulating longitudinal wires can be made from a shape memory material whose undulations contract when exposed to electromagnetic energy.

Figure 8:
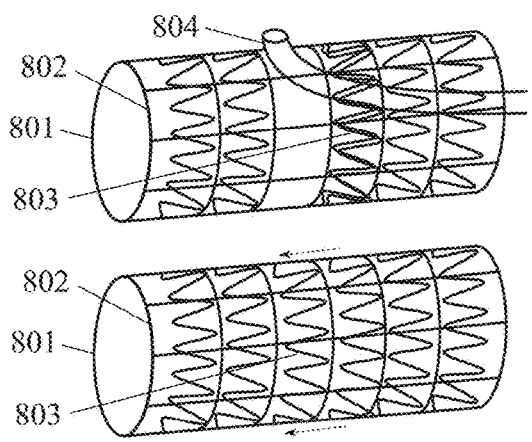
FIG. 8 shows a parent-vessel aneurysm occlusion device wherein a gap between circumferential wires (or bands) can be closed.

FIG. 8 shows two sequential views of an example of a device for occluding a cerebral aneurysm comprising: a tubular mesh 801 which is configured to be inserted into the parent blood vessel of an aneurysm; a longitudinal series of circumferential wires (or bands) including 802 and 803; and a catheter 804 for delivery of embolic coils (or other embolic material) into the aneurysm, wherein the device has a first configuration in which there is a gap between wires (or bands) in the longitudinal series of circumferential wires (or bands) through which catheter 804 extends into the aneurysm, wherein the device has a second configuration in which the catheter has been removed from the gap and the gap between circumferential wires (or bands) has been closed, and wherein the device is changed from the first configuration to the second configuration by moving wires in the longitudinal series of circumferential wires (or bands) closer together.

The upper half of FIG. 8 shows this device at a first point in time wherein there is a gap between wires (or bands) in the longitudinal series of circumferential wires (or bands) through which a catheter (or other lumen) extends into the aneurysm. The lower half of FIG. 8 shows this device at a second point in time wherein the catheter (or other lumen) has been removed from the gap and the gap between circumferential wires (or bands) has been closed. In an example, the device can be deployed in the following steps: (a) the device in its first configuration is inserted into and expanded within the parent blood vessel of an aneurysm; (b) embolic coils or other embolic material is inserted into the aneurysm sac through the catheter which extends through the gap in the wall of the device; (c) the catheter is withdrawn from the gap and from the person's body; and (d) the gap is then closed by moving wires (or bands) in the longitudinal series of circumferential wires (or bands) closer together.

In an example, the device can be changed from its first configuration to its second configuration by longitudinally pushing and/or sliding one or more wires (or bands) along the tubular mesh. In an example, a tubular mesh can have outer and inner layers. In an example, a device can be changed from its first configuration to its second configuration by longitudinally pushing and/or sliding one or more wires (or bands) along a space between those outer and inner layers. In an example, a device can have: a longitudinal series of circular circumferential wires (or bands) which do not move as the device changes from its first configuration to its second configuration; and a longitudinal series of undulating circumferential wires (or bands) which move as the device changes from its first configuration to its second configuration. Lack of movement of the former components (circular wires or bands) can help to avoid twisting or pinching the vessel wall. Movement of the latter components (undulating wires or bands) can help to close the gap through which a catheter was extended.

In an example, wires (or bands) in a longitudinal series of circumferential wires (or bands) can be circular. In an example, wires (or bands) in a longitudinal series of circumferential wires (or bands) can be undulating, sinusoidal, and/or serpentine. In an example, some wires (or bands) in a longitudinal series of circumferential wires (or bands) can be circular and other wires (or bands) in the longitudinal series of circumferential wires (or bands) can be undulating, sinusoidal, and/or serpentine. In an example, wires (or bands) in a longitudinal series of circumferential wires (or bands) can alternate between circular wires (or bands) and undulating (e.g. sinusoidal and/or serpentine) wires (or bands).

In an example, a tubular mesh can be cylindrical. In an example, a tubular mesh can be a metal stent. In an example, a tubular mesh can be a polymer stent. In an example, a tubular mesh can be a cut, braided, or 3D printed. In an example, a tubular mesh can be an expandable wire frame. In an example, a tubular mesh can self-expand when released from a catheter. In an example, a tubular mesh can further comprise radio-opaque sections or markers.

Figure 9:
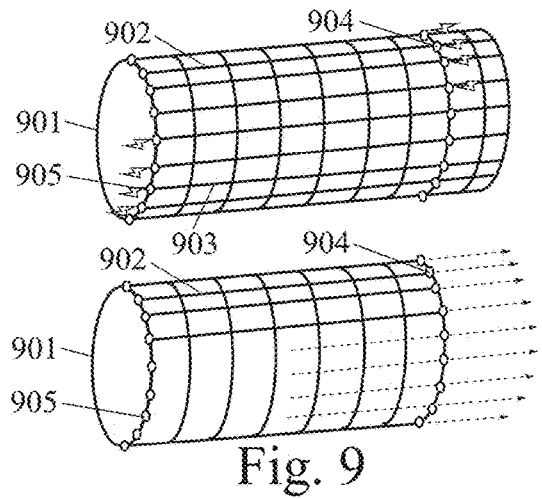
FIG. 9 shows a parent-vessel aneurysm occlusion device with a plurality of proximal and distal detachment locations on longitudinal wires or bands.

FIG. 9 shows two sequential views of an example of a device for occluding a cerebral aneurysm comprising: a tubular mesh 901 which is configured to be inserted into a parent blood vessel of an aneurysm; a plurality of longitudinal wires or bands (including wires or bands 902 and 903) which longitudinally span the tubular mesh; a plurality of proximal detachment locations (including 904) on the longitudinal wires or bands; and a plurality of distal detachment locations (including 905) on the longitudinal wires or bands, wherein "distal" means closer to the end of the device which is first inserted into the person's body and "proximal" means farther from this end, wherein proximal detachment locations are severed on a selected second set of longitudinal wires or bands (including 903) along a side of the tubular mesh which are a first distance from the aneurysm neck, wherein distal detachment locations are severed on a selected first set of longitudinal wires or bands (including 903) along a side of the tubular mesh which are a second distance from the aneurysm neck, wherein the second distance is greater than the first distance, and wherein the second set of longitudinal wires or bands is removed from the device.

The upper half of FIG. 9 shows this device at a first point in time before the second set of longitudinal wires or bands has been removed. The lower half of FIG. 9 shows this device at a second point in time after the second set of longitudinal wires or bands has been removed. In an example, this selective detachment and removal of longitudinal wires or bands results in a lower-porosity portion (e.g. on the side) of the device closer to the aneurysm neck and a higher-porosity portion (e.g. on the side) of the device farther from the aneurysm neck.

In a variation on this example, a device for occluding a cerebral aneurysm can comprise: a tubular mesh which is configured to be inserted into a parent blood vessel of an aneurysm; a plurality of longitudinal wires or bands which longitudinally span the tubular mesh; and a plurality of attachment locations on the longitudinal wires or bands, wherein attachment locations are not severed on a first set of longitudinal wires or bands along a side of the tubular mesh which are a first distance from the aneurysm neck, wherein attachment locations are severed on a second set of longitudinal wires or bands along a side of the tubular mesh which are a second distance from the aneurysm neck, wherein the second distance is greater than the first distance, and wherein the second set of longitudinal wires or bands is removed from the device. This selective detachment and removal of longitudinal wires or bands results in a lower-porosity portion (e.g. on the side) of the device closer to the aneurysm neck and a higher-porosity portion (e.g. on the side) of the device farther from the aneurysm neck.

In an example, longitudinal wires or bands can be straight. In an example, longitudinal wires or bands can be undulating, sinusoidal, and/or serpentine. In an example, longitudinal wires or bands can collectively span the entire circumference of a tubular mesh before the second set of wires or bands is detached and removed. In an example, connection locations along longitudinal wires or bands can be severed by the application of electromagnetic energy. In an example, the first set of longitudinal wires or bands can collectively span between 20% and 40% of the circumference or the tubular mesh. In an example, the first set of longitudinal wires or bands can collectively span a quarter of the circumference or the tubular mesh. In an example, the first set of longitudinal wires or bands can collectively span between 33% and 66% of the circumference or the tubular mesh. In an example, the first set of longitudinal wires or bands can collectively span half of the circumference or the tubular mesh.

Figure 10:
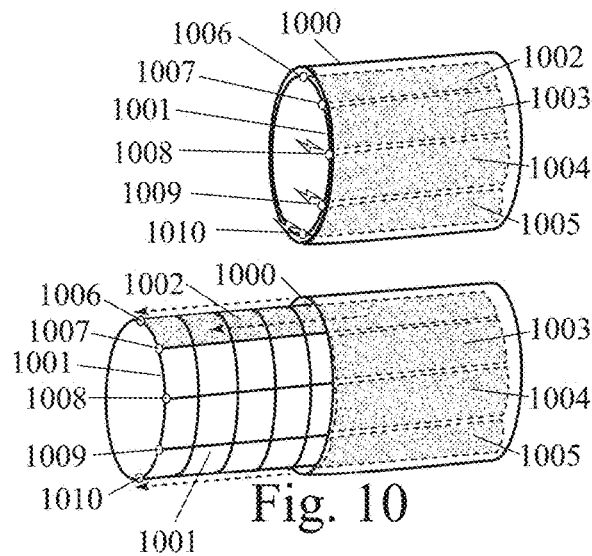
FIG. 10 shows a parent-vessel aneurysm occlusion device with a plurality of removable longitudinal strips along a tubular mesh.

FIG. 10 shows two sequential views of an example of a device for occluding a cerebral aneurysm comprising: a catheter 1000 which is configured to be inserted into a parent blood vessel of an aneurysm; a tubular mesh 1001 which is delivered to the parent vessel inside the catheter; a plurality of longitudinal strips (including strips 1002, 1003, 1004, and 1005) which are attached to the tubular mesh by a plurality of connections (including 1006, 1007, 1008, 1009, and 1010); wherein a subset of the connections (1008, 1009, and 1010) is severed by the application of electromagnetic energy before the tubular mesh extends out from the catheter; wherein a first set of the longitudinal strips (1002) remains attached to the tubular mesh and extends out from the catheter as the tubular mesh extends out from the catheter; and wherein a second set of the longitudinal strips (1003, 1004, and 1005) is detached from the tubular mesh (by severing the subset of the connections) and is not extended out from the catheter as the tubular mesh extends out from the catheter. The upper half of FIG. 10 shows this device at a first point in time before the second set of longitudinal strips has been detached and before the tubular mesh has been extended out from the catheter. The lower half of FIG. 10 shows this device at a second point in time after the second set of longitudinal strips has been detached and after the tubular mesh has been extended out from the catheter.

In an variation on this example, a device for occluding a cerebral aneurysm can comprise: a catheter which is configured to be inserted into a parent blood vessel of an aneurysm; a tubular mesh which is delivered to the parent vessel inside the catheter; a plurality of longitudinal strips or bands within catheter; wherein a first subset of the longitudinal strips or bands which are a first distance from the aneurysm neck are attached (e.g. fused) to the tubular mesh by the application of electromagnetic after the catheter has been inserted into the parent vessel but before the tubular mesh has been extended out of the catheter, and wherein a second subset of the longitudinal strips or bands which are a second distance from the aneurysm neck are not attached to the tubular mesh. This selective attachment of longitudinal strips or bands results in a lower-porosity portion (e.g. on the side) of the device closer to the aneurysm neck and a higher-porosity portion (e.g. on the side) of the device farther from the aneurysm neck.

In an example, the longitudinal strips have a lower porosity than the tubular mesh. In an example, the longitudinal strips can be made from a polymer and the tubular mesh can be made from metal. In an example, longitudinal strips can be straight. In an example, longitudinal strips can be undulating, sinusoidal, and/or serpentine. In an example, longitudinal strips can collectively span the entire circumference of a tubular mesh before the second set of strips is detached and removed. In an example, connection locations along longitudinal strips can be severed by the application of electromagnetic energy. In an example, the first set of longitudinal strips can collectively span between 20% and 40% of the circumference or the tubular mesh. In an example, the first set of longitudinal strips can collectively span a quarter of the circumference or the tubular mesh. In an example, the first set of longitudinal strips can collectively span between 33% and 66% of the circumference or the tubular mesh. In an example, the first set of longitudinal strips can collectively span half of the circumference or the tubular mesh.

Figure 11:
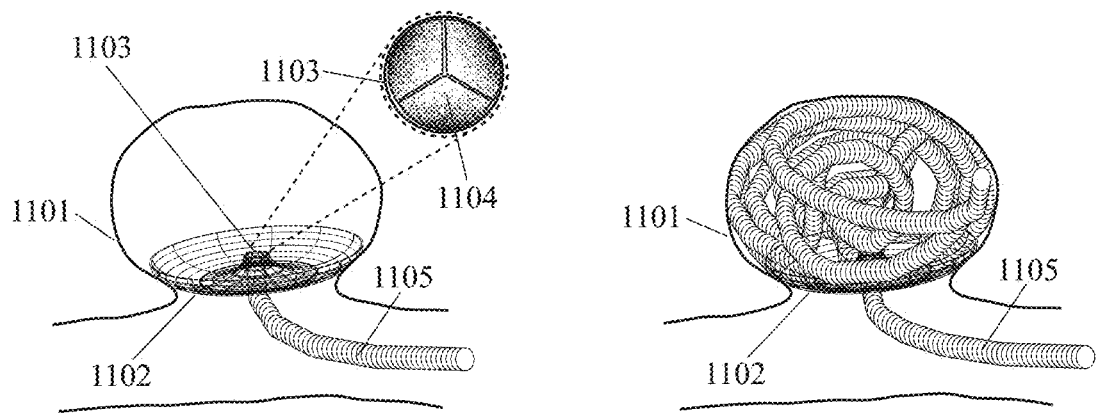
FIG. 11 shows an intrasacular aneurysm occlusion device with a half-torus mesh and coils.

The left and right sides of FIG. 11 show two sequential views of an example of an intrasacular device for occluding a cerebral aneurysm comprising: a half-torus mesh 1102 which is configured to be radially expanded within an aneurysm 1101 to bridge the neck of the aneurysm; a central opening 1103 in the half-torus mesh; a valve 1104 in the central opening; and embolic coils (or other embolic members) 1105 which are inserted through the valve into the aneurysm. The left side of FIG. 11 shows this device at a first point in time before embolic coils have been inserted through the valve into the aneurysm. The right side of FIG. 11 shows this device at a second point in time after embolic coils have been inserted through the valve into the aneurysm. After the aneurysm sac has been occluded with embolic coils, any portion of the coils which remains outside the aneurysm is detached and removed and the valve is closed to reduce blood flow into the aneurysm.

In an example, a half-torus mesh can be the lower surface of the lower half of a torus. This is analogous to the lower surface of a half of a bagel lying flat on a surface. Following this analogy, the central opening in the half-torus is analogous to the hole in a half bagel, although probably not as relatively large as the hole in a half bagel. In an example, the cross-sectional area of the central opening in the half-torus mesh can be between 5% to 15% of the maximum cross-sectional area of the half-torus mesh. In an example, the cross-sectional area of the central opening in the half-torus mesh can be between 10% to 30% of the maximum cross-sectional area of the half-torus mesh. In an example, a half-torus mesh can be created geometrically by rotating an upward-opening arc (e.g. a section of a circle or a parabola) around a vertical axis (in space) which is to the right or left of the arc. In an example, the central portion of a half-torus mesh can comprise an upward-rising cone, analogous to the cone of a volcano, with the opening being where the crater of a volcano would be. In an example, the half-torus mesh can radially expand within the aneurysm sac to a width which is greater than the width of the aneurysm neck.

In an example, a half-torus mesh can have uniform porosity. In an example, a half-torus mesh can have a uniform durometer level. In an example, a half-torus mesh can have uniform elasticity. In an example, the outer perimeter of the half-torus mesh can have greater porosity than the central portion of the half-torus mesh. In an example, the outer perimeter of the half-torus mesh can have a greater durometer level than the central portion of the half-torus mesh. In an example, the outer perimeter of the half-torus mesh can be more elastic than the central portion of the half-torus mesh. In an example, the outer perimeter of the half-torus mesh can have lower porosity than the central portion of the half-torus mesh. In an example, the outer perimeter of the half-torus mesh can have a lower durometer level than the central portion of the half-torus mesh. In an example, the outer perimeter of the half-torus mesh can be less elastic than the central portion of the half-torus mesh.

In an example, a valve in a central opening can be a leaflet valve. In an example, a valve in a central opening can be a bi-leaflet valve or tri-leaflet valve, analogous to a heart valve. In an example, a valve can passively open when an embolic coil is pushed through it and passively close when the end of the coil passes or when a portion of the coil is detached and removed. In an example, such a valve allows embolic coils to be inserted into the aneurysm after the half-torus mesh has been expanded in the aneurysm, but closes to reduce blood flow into the aneurysm after the end of the coil has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 12:
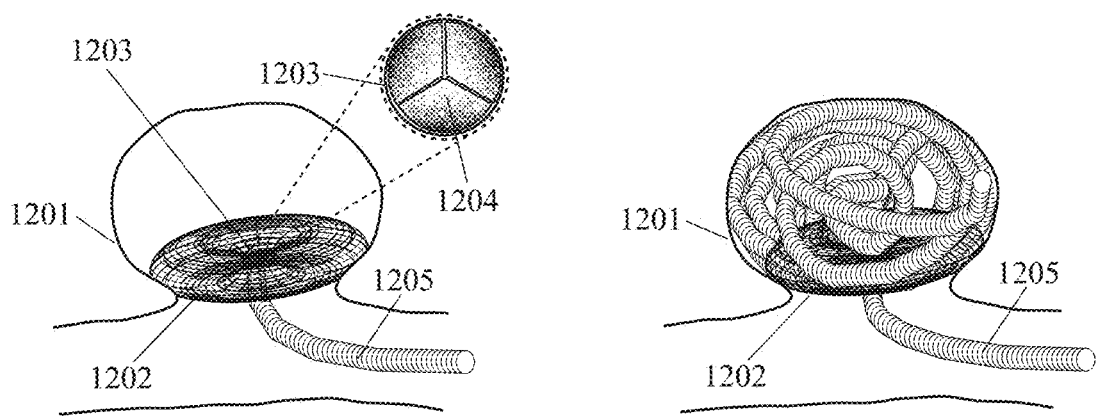
FIG. 12 shows an intrasacular aneurysm occlusion device with a toroidal mesh and coils.

The left and right sides of FIG. 12 show two sequential views of an example of an intrasacular device for occluding a cerebral aneurysm comprising: a toroidal mesh 1202 which is configured to be radially expanded within an aneurysm 1201 to bridge the neck of the aneurysm; a central opening 1203 in the toroidal mesh; a valve 1204 in the central opening; and embolic coils (or other embolic members) 1205 which are inserted through the valve into the aneurysm. The left side of FIG. 12 shows this device at a first point in time before embolic coils have been inserted through the valve into the aneurysm. The right side of FIG. 12 shows this device at a second point in time after embolic coils have been inserted through the valve into the aneurysm. After the aneurysm sac has been occluded with embolic coils, any portion of the coils which remains outside the aneurysm is detached and removed and the valve is closed to reduce blood flow into the aneurysm.

In an example, a toroidal mesh can be the outer surface of a torus. This is analogous to the outer surface of a bagel. Following this analogy, the central opening in the toroidal mesh is analogous to the hole in a bagel, although probably not as relatively large as the hole in a bagel. In an example, the cross-sectional area of the central opening in the toroidal mesh can be between 5% to 15% of the maximum cross-sectional area of the toroidal mesh. In an example, the cross-sectional area of the central opening in the toroidal mesh can be between 10% to 30% of the maximum cross-sectional area of the toroidal mesh. In an example, a toroidal mesh can be created geometrically by rotating a circle or ellipse around a vertical axis (in space) which is to the right or left of the circle or ellipse. In an example, the opening can have a hyperbolic cross-section. In an example, a toroidal mesh can radially expand within the aneurysm sac to a width which is greater than the width of the aneurysm neck.

In an example, a toroidal mesh can have uniform porosity. In an example, a toroidal mesh can have a uniform durometer level. In an example, a toroidal mesh can have uniform elasticity. In an example, the outer perimeter of the toroidal mesh can have greater porosity than the central portion of the toroidal mesh. In an example, the outer perimeter of the toroidal mesh can have a greater durometer level than the central portion of the toroidal mesh. In an example, the outer perimeter of the toroidal mesh can be more elastic than the central portion of the toroidal mesh. In an example, the outer perimeter of the toroidal mesh can have lower porosity than the central portion of the toroidal mesh. In an example, the outer perimeter of the toroidal mesh can have a lower durometer level than the central portion of the toroidal mesh. In an example, the outer perimeter of the toroidal mesh can be less elastic than the central portion of the toroidal mesh.

In an example, a valve in a central opening can be a leaflet valve. In an example, a valve in a central opening can be a bi-leaflet valve or tri-leaflet valve, analogous to a heart valve. In an example, a valve can passively open when an embolic coil is pushed through it and passively close when the end of the coil passes or when a portion of the coil is detached and removed. In an example, such a valve allows embolic coils to be inserted into the aneurysm after the toroidal mesh has been expanded in the aneurysm, but closes to reduce blood flow into the aneurysm after the end of the coil has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 13:
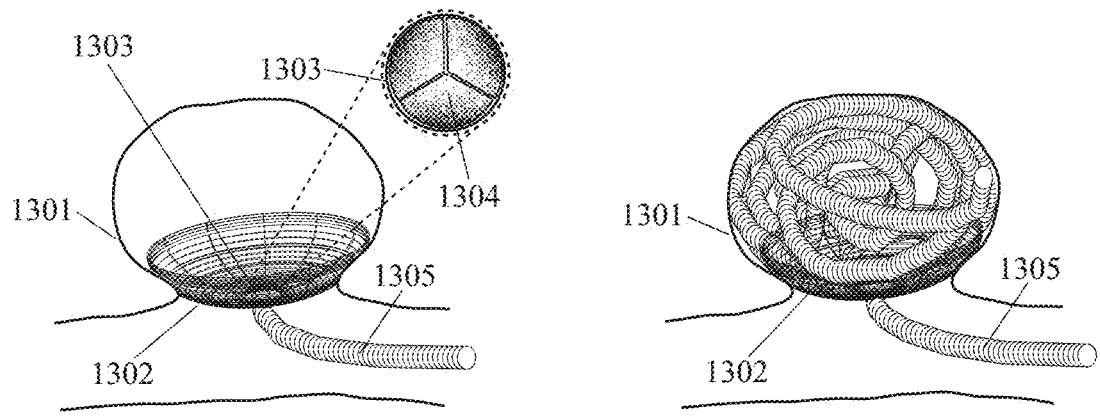
FIG. 13 shows an intrasacular aneurysm occlusion device with a bowl-shaped mesh and coils.

The left and right sides of FIG. 13 show two sequential views of an example of an intrasacular device for occluding a cerebral aneurysm comprising: a bowl-shaped mesh 1302 which is configured to be radially expanded within an aneurysm 1301 to bridge the neck of the aneurysm; a central opening 1303 in the bowl-shaped mesh; a valve 1304 in the central opening; and embolic coils (or other embolic members) 1305 which are inserted through the valve into the aneurysm. The left side of FIG. 13 shows this device at a first point in time before embolic coils have been inserted through the valve into the aneurysm. The right side of FIG. 13 shows this device at a second point in time after embolic coils have been inserted through the valve into the aneurysm. After the aneurysm sac has been occluded with embolic coils, any portion of the coils which remains outside the aneurysm is detached and removed and the valve is closed to reduce blood flow into the aneurysm.

In an example, a bowl-shaped mesh can be a section of a sphere or ellipsoid. In an example, a bowl-shaped mesh can be hemispherical. In an example, the cross-sectional area of the central opening in the bowl-shaped mesh can be between 5% to 15% of the maximum cross-sectional area of the bowl-shaped mesh. In an example, the cross-sectional area of the central opening in the bowl-shaped mesh can be between 10% to 30% of the maximum cross-sectional area of the bowl-shaped mesh. In an example, a bowl-shaped mesh can be created geometrically by rotating an arc of a circle or ellipse around a vertical axis (in space) which is to the right or left of the circle or ellipse. In an example, a bowl-shaped mesh can radially expand within the aneurysm sac to a width which is greater than the width of the aneurysm neck.

In an example, a bowl-shaped mesh can have uniform porosity. In an example, a bowl-shaped mesh can have a uniform durometer level. In an example, a bowl-shaped mesh can have uniform elasticity. In an example, the outer perimeter of the bowl-shaped mesh can have greater porosity than the central portion of the bowl-shaped mesh. In an example, the outer perimeter of the bowl-shaped mesh can have a greater durometer level than the central portion of the bowl-shaped mesh. In an example, the outer perimeter of the bowl-shaped mesh can be more elastic than the central portion of the bowl-shaped mesh. In an example, the outer perimeter of the bowl-shaped mesh can have lower porosity than the central portion of the bowl-shaped mesh. In an example, the outer perimeter of the bowl-shaped mesh can have a lower durometer level than the central portion of the bowl-shaped mesh. In an example, the outer perimeter of the bowl-shaped mesh can be less elastic than the central portion of the bowl-shaped mesh.

In an example, a valve in a central opening can be a leaflet valve. In an example, a valve in a central opening can be a bi-leaflet valve or tri-leaflet valve, analogous to a heart valve. In an example, a valve can passively open when an embolic coil is pushed through it and passively close when the end of the coil passes or when a portion of the coil is detached and removed. In an example, such a valve allows embolic coils to be inserted into the aneurysm after the bowl-shaped mesh has been expanded in the aneurysm, but closes to reduce blood flow into the aneurysm after the end of the coil has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 14:
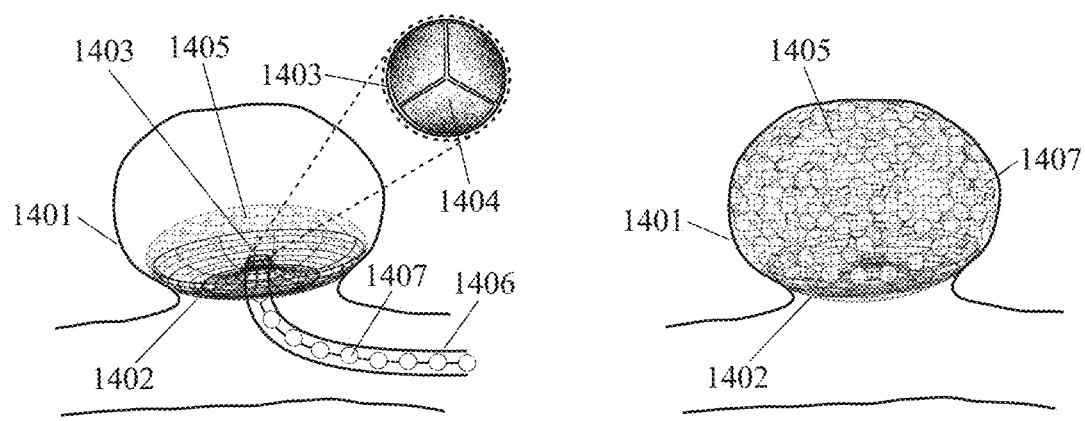
FIG. 14 shows an intrasacular aneurysm occlusion device with a proximal half-torus mesh and a distal flexible net.

The left and right sides of FIG. 14 show two sequential views of an example of an intrasacular device for occluding a cerebral aneurysm comprising: a distal flexible net 1405 which is inserted into an aneurysm 1401; a proximal half-torus mesh 1402 which is configured to be radially expanded within the aneurysm to bridge the neck of the aneurysm; a central opening 1403 in the half-torus mesh; a valve 1404 in the central opening; and a string-of-pearls embolic member (e.g. a longitudinal series of embolic components which are connected by a flexible filament or wire) 1407 which is delivered through a catheter 1406 and inserted through the valve into the distal flexible net, thereby expanding the distal flexible net to fill the sac of even an irregularly-shaped aneurysm.

The left side of FIG. 14 shows this device at a first point in time before the string-of-pearls embolic member has been inserted through the valve into the distal flexible net. The right side of FIG. 14 shows this device at a second point in time after the string-of-pearls embolic member has been inserted through the valve into the distal flexible net. In an example, the distal flexible net can be attached to the half-torus mesh. In an example, the distal flexible net can be attached to the distal surface of the half-torus mesh. In an example, the distal flexible net can be attached to the outer perimeter of the half-torus mesh. In an example, the distal flexible net can be separate from the half-torus mesh. In an example, the distal flexible mesh can be made from a polymer and the half-torus mesh can be made from metal.

In an example, a string-of-pearls embolic member can comprise a longitudinal series of embolic components (e.g. the "pearls") which are connected by a flexible filament or wire (e.g. the "string"). In an example, the pearl components in a string-of-pearls embolic member can have an average size which is greater than the average size of openings in the distal flexible net. In an example, the pearl components in a string-of-pearls embolic member can have an average size which is between 1 and 5 times the average size of openings in the distal flexible net. In an example, the average length of filament or wire segments connecting pearl components in a string-of-pearls embolic member can be between 1 and 10 times the average size of the pearl components in the string-of-pearls embolic member. In an example, the average length of filament or wire segments connecting pearl components in a string-of-pearls embolic member can be between 1 and 10 times the average size of openings in the distal flexible net. In an example, series of separate embolic members (e.g. microsponges or hydrogels) can be inserted instead of a string-of-pearls embolic member.

In an example, a half-torus mesh can be the lower surface of the lower half of a torus. This is analogous to the lower surface of a half of a bagel lying flat on a surface. Following this analogy, the central opening in the half-torus is analogous to the hole in a half bagel, although probably not as relatively large as the hole in a half bagel. In an example, the cross-sectional area of the central opening in the half-torus mesh can be between 5% to 15% of the maximum cross-sectional area of the half-torus mesh. In an example, the cross-sectional area of the central opening in the half-torus mesh can be between 10% to 30% of the maximum cross-sectional area of the half-torus mesh. In an example, a half-torus mesh can be created geometrically by rotating an upward-opening arc (e.g. a section of a circle or a parabola) around a vertical axis (in space) which is to the right or left of the arc. In an example, the central portion of a half-torus mesh can comprise an upward-rising cone, analogous to the cone of a volcano, with the opening being where the crater of a volcano would be. In an example, the half-torus mesh can radially expand within the aneurysm sac to a width which is greater than the width of the aneurysm neck.

In an example, a half-torus mesh can have uniform porosity. In an example, a half-torus mesh can have a uniform durometer level. In an example, a half-torus mesh can have uniform elasticity. In an example, the outer perimeter of the half-torus mesh can have greater porosity than the central portion of the half-torus mesh. In an example, the outer perimeter of the half-torus mesh can have a greater durometer level than the central portion of the half-torus mesh. In an example, the outer perimeter of the half-torus mesh can be more elastic than the central portion of the half-torus mesh. In an example, the outer perimeter of the half-torus mesh can have lower porosity than the central portion of the half-torus mesh. In an example, the outer perimeter of the half-torus mesh can have a lower durometer level than the central portion of the half-torus mesh. In an example, the outer perimeter of the half-torus mesh can be less elastic than the central portion of the half-torus mesh.

In an example, a valve in a central opening can be a leaflet valve. In an example, a valve in a central opening can be a bi-leaflet valve or tri-leaflet valve, analogous to a heart valve. In an example, a valve can passively open when a string-of-pearls embolic member is pushed through it and passively close when the end of the embolic member passes or when a portion of the embolic member is detached and removed. In an example, such a valve allows a string-of-pearls embolic member to be inserted into the distal flexible net after the half-torus mesh has been expanded in the aneurysm, but closes to reduce blood flow into the aneurysm after the end of the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 15:
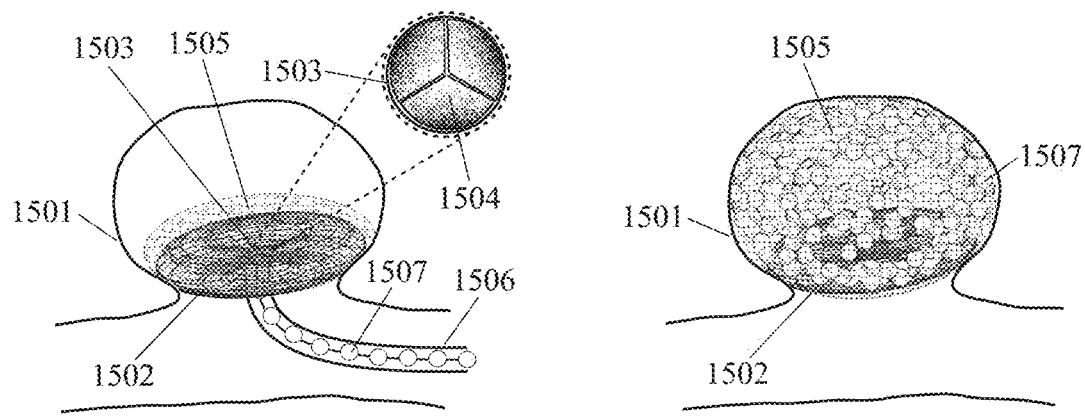
FIG. 15 shows an intrasacular aneurysm occlusion device with a proximal toroidal mesh and a distal flexible net.

The left and right sides of FIG. 15 show two sequential views of an example of an intrasacular device for occluding a cerebral aneurysm comprising: a distal flexible net 1505 which is inserted into an aneurysm 1501; a proximal toroidal mesh 1502 which is configured to be radially expanded within the aneurysm to bridge the neck of the aneurysm; a central opening 1503 in the toroidal mesh; a valve 1504 in the central opening; and a string-of-pearls embolic member (e.g. a longitudinal series of embolic components which are connected by a flexible filament or wire) 1507 which is delivered through a catheter 1506 and inserted through the valve into the distal flexible net, thereby expanding the distal flexible net to fill the sac of even an irregularly-shaped aneurysm.

The left side of FIG. 15 shows this device at a first point in time before the string-of-pearls embolic member has been inserted through the valve into the distal flexible net. The right side of FIG. 15 shows this device at a second point in time after the string-of-pearls embolic member has been inserted through the valve into the distal flexible net. In an example, the distal flexible net can be attached to the toroidal mesh. In an example, the distal flexible net can be attached to the distal surface of the toroidal mesh. In an example, the distal flexible net can be attached to the outer perimeter of the toroidal mesh. In an example, the distal flexible net can be separate from the toroidal mesh. In an example, the distal flexible mesh can be made from a polymer and the toroidal mesh can be made from metal.

In an example, a string-of-pearls embolic member can comprise a longitudinal series of embolic components (e.g. the "pearls") which are connected by a flexible filament or wire (e.g. the "string"). In an example, the pearl components in a string-of-pearls embolic member can have an average size which is greater than the average size of openings in the distal flexible net. In an example, the pearl components in a string-of-pearls embolic member can have an average size which is between 1 and 5 times the average size of openings in the distal flexible net. In an example, the average length of filament or wire segments connecting pearl components in a string-of-pearls embolic member can be between 1 and 10 times the average size of the pearl components in the string-of-pearls embolic member. In an example, the average length of filament or wire segments connecting pearl components in a string-of-pearls embolic member can be between 1 and 10 times the average size of openings in the distal flexible net. In an example, series of separate embolic members (e.g. microsponges or hydrogels) can be inserted instead of a string-of-pearls embolic member.

In an example, a toroidal mesh can be the outer surface of a torus. This is analogous to the outer surface of a bagel. Following this analogy, the central opening in the toroidal mesh is analogous to the hole in a bagel, although probably not as relatively large as the hole in a bagel. In an example, the cross-sectional area of the central opening in the toroidal mesh can be between 5% to 15% of the maximum cross-sectional area of the toroidal mesh. In an example, the cross-sectional area of the central opening in the toroidal mesh can be between 10% to 30% of the maximum cross-sectional area of the toroidal mesh. In an example, a toroidal mesh can be created geometrically by rotating a circle or ellipse around a vertical axis (in space) which is to the right or left of the circle or ellipse. In an example, the opening can have a hyperbolic cross-section. In an example, a toroidal mesh can radially expand within the aneurysm sac to a width which is greater than the width of the aneurysm neck.

In an example, a toroidal mesh can have uniform porosity. In an example, a toroidal mesh can have a uniform durometer level. In an example, a toroidal mesh can have uniform elasticity. In an example, the outer perimeter of the toroidal mesh can have greater porosity than the central portion of the toroidal mesh. In an example, the outer perimeter of the toroidal mesh can have a greater durometer level than the central portion of the toroidal mesh. In an example, the outer perimeter of the toroidal mesh can be more elastic than the central portion of the toroidal mesh. In an example, the outer perimeter of the toroidal mesh can have lower porosity than the central portion of the toroidal mesh. In an example, the outer perimeter of the toroidal mesh can have a lower durometer level than the central portion of the toroidal mesh. In an example, the outer perimeter of the toroidal mesh can be less elastic than the central portion of the toroidal mesh.

In an example, a valve in a central opening can be a leaflet valve. In an example, a valve in a central opening can be a bi-leaflet valve or tri-leaflet valve, analogous to a heart valve. In an example, a valve can passively open when a string-of-pearls embolic member is pushed through it and passively close when the end of the embolic member passes or when a portion of the embolic member is detached and removed. In an example, such a valve allows a string-of-pearls embolic member to be inserted into the distal flexible net after the toroidal mesh has been expanded in the aneurysm, but closes to reduce blood flow into the aneurysm after the end of the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 16:
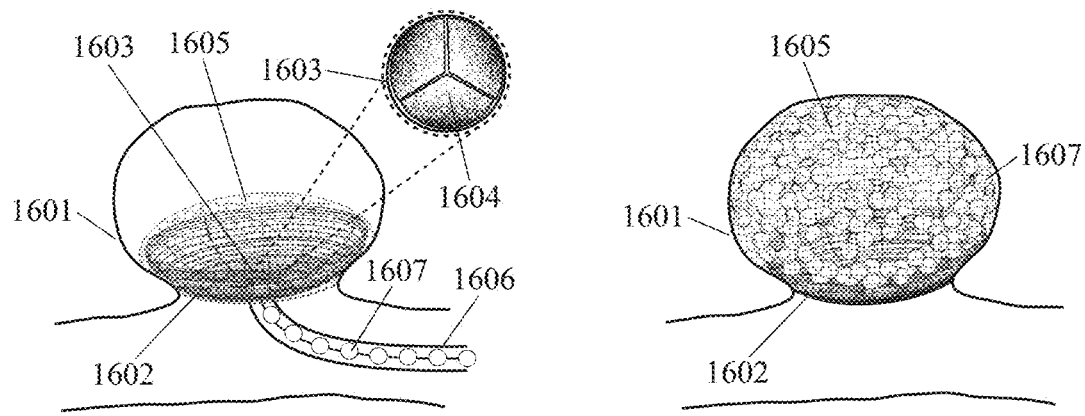
FIG. 16 shows an intrasacular aneurysm occlusion device with a proximal bowl-shaped mesh and a distal flexible net.

The left and right sides of FIG. 16 show two sequential views of an example of an intrasacular device for occluding a cerebral aneurysm comprising: a distal flexible net 1605 which is inserted into an aneurysm 1601; a proximal bowl-shaped mesh 1602 which is configured to be radially expanded within the aneurysm to bridge the neck of the aneurysm; a central opening 1603 in the bowl-shaped mesh; a valve 1604 in the central opening; and a string-of-pearls embolic member (e.g. a longitudinal series of embolic components which are connected by a flexible filament or wire) 1607 which is delivered through a catheter 1606 and inserted through the valve into the distal flexible net, thereby expanding the distal flexible net to fill the sac of even an irregularly-shaped aneurysm.

The left side of FIG. 16 shows this device at a first point in time before the string-of-pearls embolic member has been inserted through the valve into the distal flexible net. The right side of FIG. 16 shows this device at a second point in time after the string-of-pearls embolic member has been inserted through the valve into the distal flexible net. In an example, the distal flexible net can be attached to the bowl-shaped mesh. In an example, the distal flexible net can be attached to the distal surface of the bowl-shaped mesh. In an example, the distal flexible net can be attached to the outer perimeter of the bowl-shaped mesh. In an example, the distal flexible net can be separate from the bowl-shaped mesh. In an example, the distal flexible mesh can be made from a polymer and the bowl-shaped mesh can be made from metal.

In an example, a string-of-pearls embolic member can comprise a longitudinal series of embolic components (e.g. the "pearls") which are connected by a flexible filament or wire (e.g. the "string"). In an example, the pearl components in a string-of-pearls embolic member can have an average size which is greater than the average size of openings in the distal flexible net. In an example, the pearl components in a string-of-pearls embolic member can have an average size which is between 1 and 5 times the average size of openings in the distal flexible net. In an example, the average length of filament or wire segments connecting pearl components in a string-of-pearls embolic member can be between 1 and 10 times the average size of the pearl components in the string-of-pearls embolic member. In an example, the average length of filament or wire segments connecting pearl components in a string-of-pearls embolic member can be between 1 and 10 times the average size of openings in the distal flexible net. In an example, series of separate embolic members (e.g. microsponges or hydrogels) can be inserted instead of a string-of-pearls embolic member.

In an example, a bowl-shaped mesh can be a section of a sphere or ellipsoid. In an example, a bowl-shaped mesh can be hemispherical. In an example, the cross-sectional area of the central opening in the bowl-shaped mesh can be between 5% to 15% of the maximum cross-sectional area of the bowl-shaped mesh. In an example, the cross-sectional area of the central opening in the bowl-shaped mesh can be between 10% to 30% of the maximum cross-sectional area of the bowl-shaped mesh. In an example, a bowl-shaped mesh can be created geometrically by rotating a circle or ellipse around a vertical axis (in space) which is to the right or left of the circle or ellipse. In an example, a bowl-shaped mesh can radially expand within the aneurysm sac to a width which is greater than the width of the aneurysm neck.

In an example, a bowl-shaped mesh can have uniform porosity. In an example, a bowl-shaped mesh can have a uniform durometer level. In an example, a bowl-shaped mesh can have uniform elasticity. In an example, the outer perimeter of the bowl-shaped mesh can have greater porosity than the central portion of the bowl-shaped mesh. In an example, the outer perimeter of the bowl-shaped mesh can have a greater durometer level than the central portion of the bowl-shaped mesh. In an example, the outer perimeter of the bowl-shaped mesh can be more elastic than the central portion of the bowl-shaped mesh. In an example, the outer perimeter of the bowl-shaped mesh can have lower porosity than the central portion of the bowl-shaped mesh. In an example, the outer perimeter of the bowl-shaped mesh can have a lower durometer level than the central portion of the bowl-shaped mesh. In an example, the outer perimeter of the bowl-shaped mesh can be less elastic than the central portion of the bowl-shaped mesh.

In an example, a valve in a central opening can be a leaflet valve. In an example, a valve in a central opening can be a bi-leaflet valve or tri-leaflet valve, analogous to a heart valve. In an example, a valve can passively open when a string-of-pearls embolic member is pushed through it and passively close when the end of the embolic member passes or when a portion of the embolic member is detached and removed. In an example, such a valve allows a string-of-pearls embolic member to be inserted into the distal flexible net after the bowl-shaped mesh has been expanded in the aneurysm, but closes to reduce blood flow into the aneurysm after the end of the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 17:
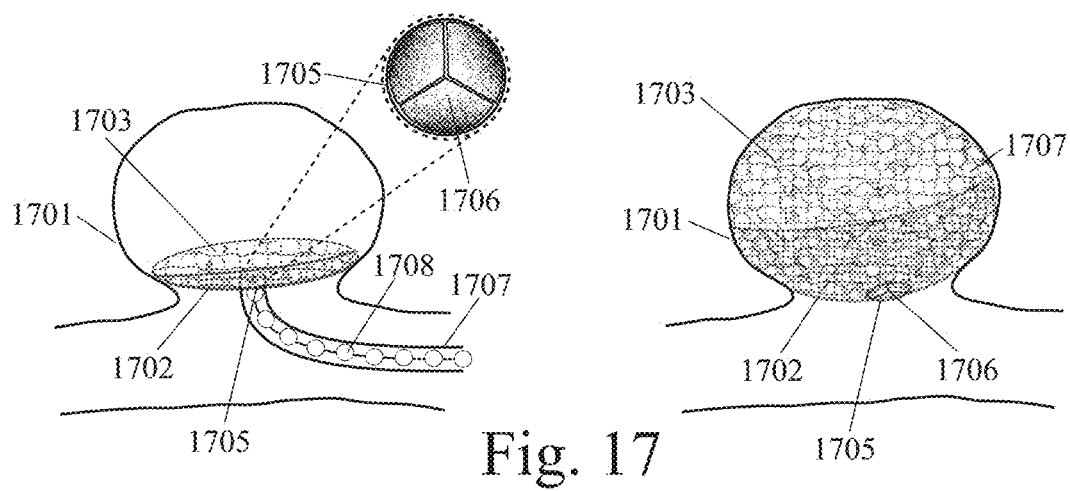
FIG. 17 shows an intrasacular aneurysm occlusion device comprising a net or mesh with a flexible distal portion.

The left and right sides of FIG. 17 show two sequential views of an example of an intrasacular device for occluding a cerebral aneurysm comprising: a flexible net or mesh which is inserted into an aneurysm 1701; wherein the flexible net further comprises a proximal portion 1702, wherein the proximal portion is configured to be a first distance from the aneurysm neck and has a first level of flexibility (or elasticity); wherein the flexible net further comprises a distal portion 1703, wherein the distal portion is configured to be a second distance from the aneurysm neck and has a second level of flexibility (or elasticity), wherein the second distance is greater than the first distance, and wherein the second level is greater than the first level; a central opening 1705 in the proximal portion; a valve 1706 in the central opening; and a string-of-pearls embolic member (e.g. a longitudinal series of embolic components which are connected by a flexible filament or wire) 1708 which is delivered through a catheter 1707 and inserted through the valve into the flexible net or mesh, thereby expanding the flexible net or mesh to fill the sac of even an irregularly-shaped aneurysm. The left side of FIG. 17 shows this device at a first point in time before the string-of-pearls embolic member has been inserted through the valve into the flexible net. The right side of FIG. 17 shows this device at a second point in time after the string-of-pearls embolic member has been inserted through the valve into the flexible net.

In an example, a proximal portion of a flexible net (or mesh) can be made from one or more metals and a distal portion of the flexible net (or mesh) can be made from one or more polymers. In an example, the composition of a proximal portion can have a greater percentage of metal than that of a distal portion. In an example, filaments, tubes, fibers, or wires in a proximal portion can be closer together than those in a distal portion. In an example, the proximal portion can have a first porosity level and the distal portion can have a second porosity level, wherein the second level is greater than the first level. In an example, the outer perimeter of the proximal portion can have a lower porosity than the central area of the proximal portion (apart from the central opening). In an example, the outer perimeter of the proximal portion can have a lower durometer level than the central area of the proximal portion. In an example, the outer perimeter of the proximal portion can be less elastic than the central area of the proximal portion.

In an example, a proximal portion of a flexible net (or mesh) can have a first resilience (or strength) level and the distal portion of the flexible net (or mesh) can have a second resilience (or strength) level, wherein the second level is less than the first level. In an example, the proximal portion can have a first elastic modulus and the distal portion can have a second elastic modulus, wherein the second elastic modulus is greater than the first elastic modulus. In an example, the proximal portion can have a first Shore durometer and the distal portion can have a second Shore durometer, wherein the second Shore durometer is less than the first Shore durometer. In an example, a proximal portion of a flexible net can have more layers than a distal portion of the flexible net. In an example, a proximal portion of a flexible net can comprise a single layer and a distal portion of the flexible net can comprise two or more layers.

In an example, a proximal portion of a flexible net (or mesh) can comprise between 20% and 40% area of the flexible net (or mesh) and a distal portion can comprise the remainder of the area of the flexible net (or mesh). In an example, the proximal portion can comprise one third of the area of the flexible net (or mesh) and the distal portion can comprise two thirds of the area of the flexible net (or mesh). In an example, the proximal portion can comprise between 33% and 66% of the area of the flexible net (or mesh) and the distal portion can comprise the remainder of the area of the flexible net (or mesh). In an example, the proximal portion can comprise one half of the area of the flexible net (or mesh) and the distal portion can comprise the other half of the area of the flexible net (or mesh).

In an example, a string-of-pearls embolic member can comprise a longitudinal series of embolic components (e.g. the "pearls") which are connected by a flexible filament or wire (e.g. the "string"). In an example, the pearl components in a string-of-pearls embolic member can have an average size which is greater than the average size of openings in the distal portion of the flexible net (or mesh). In an example, the pearl components in a string-of-pearls embolic member can have an average size which is between 1 and 5 times the average size of openings in the distal portion. In an example, the average length of filament or wire segments connecting pearl components in a string-of-pearls embolic member can be between 1 and 10 times the average size of the pearl components in the string-of-pearls embolic member. In an example, the average length of filament or wire segments connecting pearl components in a string-of-pearls embolic member can be between 1 and 10 times the average size of openings in the distal portion. In an example, series of separate embolic members (e.g. microsponges or hydrogels) can be inserted instead of a string-of-pearls embolic member.

In an example, a valve in a central opening can be a leaflet valve. In an example, a valve in a central opening can be a bi-leaflet valve or tri-leaflet valve, analogous to a heart valve. In an example, a valve can passively open when a string-of-pearls embolic member is pushed through it and passively close when the end of the embolic member passes or when a portion of the embolic member is detached and removed. In an example, such a valve allows a string-of-pearls embolic member to be inserted into the distal portion after the distal portion has been expanded in the aneurysm, but closes to reduce blood flow into the aneurysm after the end of the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 18:
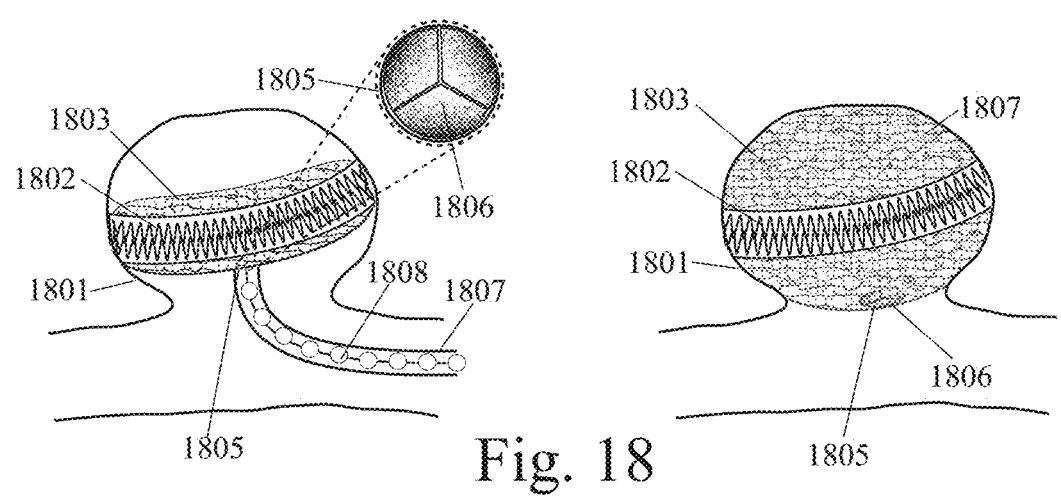
FIG. 18 shows an intrasacular aneurysm occlusion device with a resilient mesh (e.g. ring stent) around a central circumference of a net.

The left and right sides of FIG. 18 show two sequential views of an example of an intrasacular device for occluding a cerebral aneurysm comprising: a flexible net 1803 which is inserted into an aneurysm 1801; a resilient mesh (e.g. a stent) 1802 which encircles a central circumference of the flexible net; a proximal opening 1805 in the flexible net; a valve 1806 in the proximal opening; and a string-of-pearls embolic member (e.g. a longitudinal series of embolic components which are connected by a flexible filament or wire) 1808 which is delivered through a catheter 1807 and inserted through the valve into the flexible net, thereby expanding the flexible net or mesh to fill the sac of even an irregularly-shaped aneurysm. The left side of FIG. 18 shows this device at a first point in time before the string-of-pearls embolic member has been inserted through the valve into the flexible net. The right side of FIG. 18 shows this device at a second point in time after the string-of-pearls embolic member has been inserted through the valve into the flexible net.

In an example, a resilient mesh can be a metal stent or a polymer stent. In an example, a resilient mesh can be made from one or more metals and a flexible mesh can be made from one or more polymers. In an example, a resilient mesh can be an expandable wire frame. In an example, a resilient mesh can self-expand in a radial manner within the aneurysm sac. In an example, a resilient mesh can be a circular stent. In an example, a resilient mesh can be an ellipsoidal stent. In an example, a resilient mesh can be a cylindrical stent. In an example, a resilient mesh can be a tubular stent. In an example, a resilient mesh can be a toroidal stent. In an example, a resilient mesh can be cut, braided, or 3D printed. In an example, a resilient mesh can further comprise radio-opaque sections or markers.

In an example, a resilient mesh can span a central and/or maximal diameter of an aneurysm sac. In an example, a resilient mesh can span a central and/or maximal circumference of an aneurysm sac. In an example, a resilient mesh can be attached to the interior surface of a flexible net. In an example, a resilient mesh can be attached to the exterior surface of a flexible net. In an example, a resilient mesh can overlap between 5% and 15% of the area of a flexible net when both are expanded within an aneurysm sac. In an example, a resilient mesh can overlap between 10% and 30% of the area of a flexible net when both are expanded within an aneurysm sac.

In an example, a string-of-pearls embolic member can comprise a longitudinal series of embolic components (e.g. the "pearls") which are connected by a flexible filament or wire (e.g. the "string"). In an example, a flexible net can have quadrilateral-shaped openings. In an example, a flexible net can have hexagonal openings. In an example, a flexible net can have triangular openings. In an example, a flexible net can have circular openings. In an example, embolic components (e.g. the "pearls") in a string-of-pearls embolic member can be generally spherical and openings in a flexible net can be generally circular. In an example, embolic components (e.g. the "pearls") in a string-of-pearls embolic member can be generally polygonal and openings in a flexible net can be generally circular. In an example, embolic components (e.g. the "pearls") in a string-of-pearls embolic member can be generally spherical and openings in a flexible net can be generally polygonal.

In an example, pearl components in a string-of-pearls embolic member can have an average size which is greater than the average size of openings in a flexible net. In an example, pearl components in a string-of-pearls embolic member can have an average size which is between 1 and 5 times the average size of openings in the flexible net. In an example, the average length of filament or wire segments connecting pearl components in a string-of-pearls embolic member can be between 1 and 10 times the average size of the pearl components in the string-of-pearls embolic member. In an example, the average length of filament or wire segments connecting pearl components in a string-of-pearls embolic member can be between 1 and 10 times the average size of openings in the flexible net. In an example, series of separate embolic members (e.g. microsponges or hydrogels) can be inserted instead of a string-of-pearls embolic member.

In an example, a valve in a central opening can be a leaflet valve. In an example, a valve in a central opening can be a bi-leaflet valve or tri-leaflet valve, analogous to a heart valve. In an example, a valve can passively open when a string-of-pearls embolic member is pushed through it and passively close when the end of the embolic member passes or when a portion of the embolic member is detached and removed. In an example, such a valve allows a string-of-pearls embolic member to be inserted into the flexible net, but closes to reduce blood flow into the aneurysm after the end of the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 19:
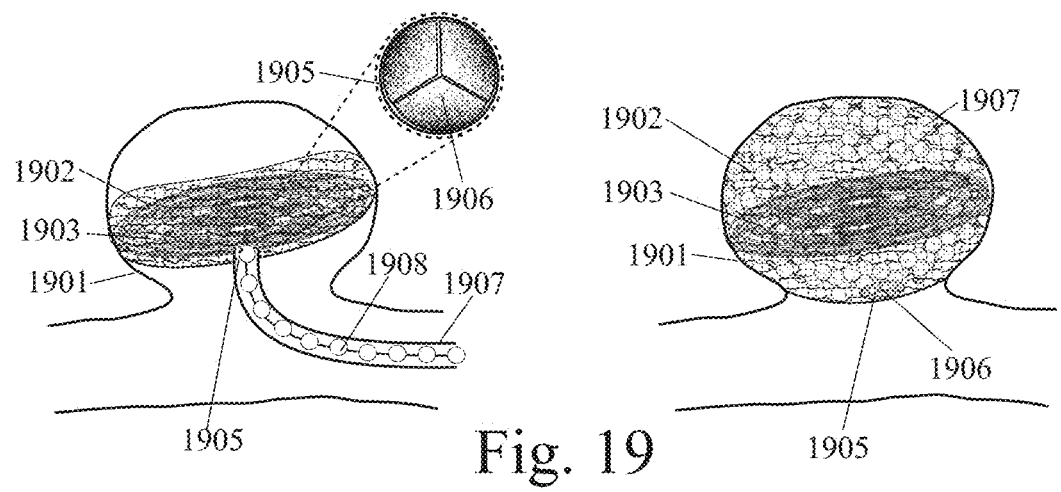
FIG. 19 shows an intrasacular aneurysm occlusion device with a disk or ball-shaped mesh inside a net.

The left and right sides of FIG. 19 show two sequential views of an example of an intrasacular device for occluding a cerebral aneurysm comprising: a flexible net 1902 which is inserted into an aneurysm 1901; a disk or ball-shaped mesh 1903 inside the flexible net; a proximal opening 1905 in the flexible net; a valve 1906 in the proximal opening; and a string-of-pearls embolic member (e.g. a longitudinal series of embolic components which are connected by a flexible filament or wire) 1908 which is delivered through a catheter 1907 and inserted through the valve into the flexible net, thereby expanding the flexible net or mesh to fill the sac of even an irregularly-shaped aneurysm. The left side of FIG. 19 shows this device at a first point in time before the string-of-pearls embolic member has been inserted through the valve into the flexible net. The right side of FIG. 19 shows this device at a second point in time after the string-of-pearls embolic member has been inserted through the valve into the flexible net.

In an example, a disk or ball-shaped mesh can spherical. In an example, a disk or ball-shaped mesh can ellipsoidal. In an example, a disk or ball-shaped mesh can apple or barrel shaped. In an example, a disk or ball-shaped mesh can be made from one or more metals and a flexible mesh can be made from one or more polymers. In an example, a disk or ball-shaped mesh can be an expandable wire frame. In an example, a disk or ball-shaped mesh can self-expand in a radial manner within the aneurysm sac. In an example, a disk or ball-shaped mesh can be cut, braided, or 3D printed. In an example, a disk or ball-shaped mesh can further comprise radio-opaque sections or markers. In an example, there can be an opening in the disk or ball-shaped mesh in addition to the opening in the flexible net.

In an example, a string-of-pearls embolic member can comprise a longitudinal series of embolic components (e.g. the "pearls") which are connected by a flexible filament or wire (e.g. the "string"). In an example, a flexible net can have quadrilateral-shaped openings. In an example, a flexible net can have hexagonal openings. In an example, a flexible net can have triangular openings. In an example, a flexible net can have circular openings. In an example, embolic components (e.g. the "pearls") in a string-of-pearls embolic member can be generally spherical and openings in a flexible net can be generally circular. In an example, embolic components (e.g. the "pearls") in a string-of-pearls embolic member can be generally polygonal and openings in a flexible net can be generally circular. In an example, embolic components (e.g. the "pearls") in a string-of-pearls embolic member can be generally spherical and openings in a flexible net can be generally polygonal.

In an example, pearl components in a string-of-pearls embolic member can have an average size which is greater than the average size of openings in a flexible net. In an example, pearl components in a string-of-pearls embolic member can have an average size which is between 1 and 5 times the average size of openings in the flexible net. In an example, the average length of filament or wire segments connecting pearl components in a string-of-pearls embolic member can be between 1 and 10 times the average size of the pearl components in the string-of-pearls embolic member. In an example, the average length of filament or wire segments connecting pearl components in a string-of-pearls embolic member can be between 1 and 10 times the average size of openings in the flexible net. In an example, series of separate embolic members (e.g. microsponges or hydrogels) can be inserted instead of a string-of-pearls embolic member.

In an example, a valve in a central opening can be a leaflet valve. In an example, a valve in a central opening can be a bi-leaflet valve or tri-leaflet valve, analogous to a heart valve. In an example, a valve can passively open when a string-of-pearls embolic member is pushed through it and passively close when the end of the embolic member passes or when a portion of the embolic member is detached and removed. In an example, such a valve allows a string-of-pearls embolic member to be inserted into the flexible net, but closes to reduce blood flow into the aneurysm after the end of the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 20:
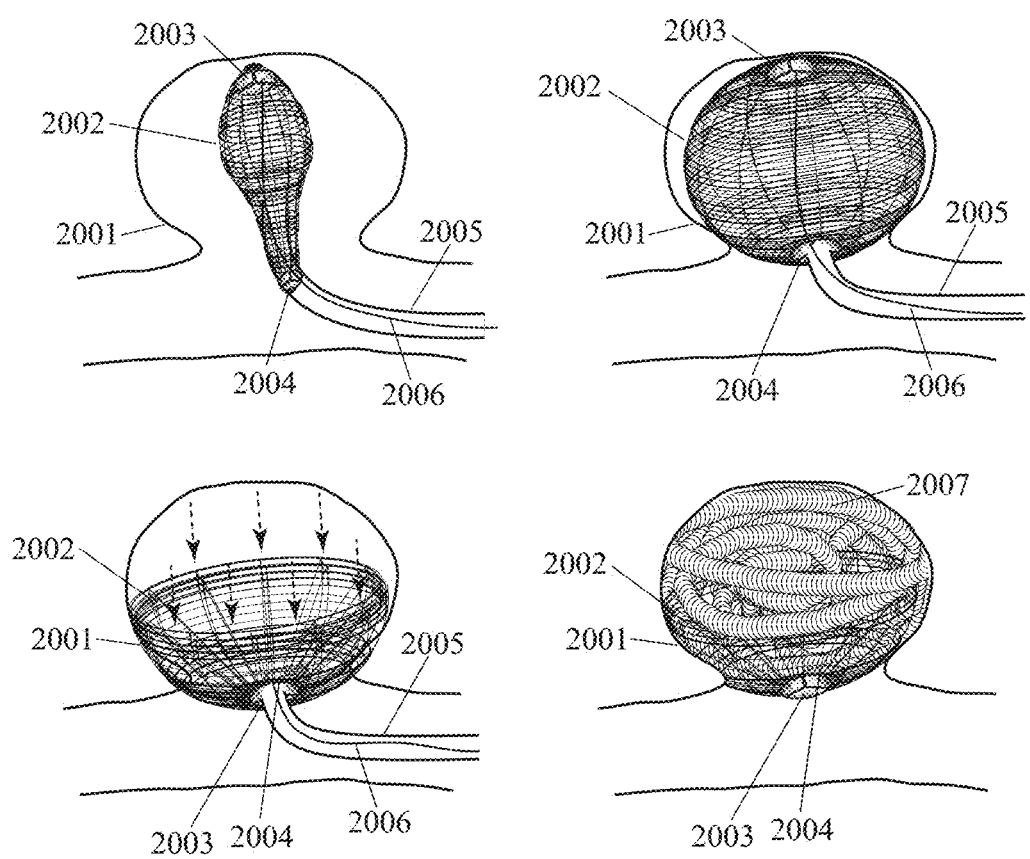
FIG. 20 shows an intrasacular aneurysm occlusion device wherein a mesh is radially-expanded and then longitudinally-collapsed in an aneurysm.

FIG. 20 shows four sequential views of an example of an intrasacular device for occluding a cerebral aneurysm comprising: a mesh (or framework) 2002 which is configured to be inserted, radially-expanded, and then longitudinally-collapsed within an aneurysm 2001 in order to bridge the aneurysm neck, wherein the mesh (or framework) has a longitudinal first configuration in which it is delivered through a catheter and inserted into an aneurysm, wherein the mesh (or framework) has a single-layer globular second configuration after it has been radially-expanded within the aneurysm, and wherein the mesh (or framework) has a double-layer bowl-shaped third configuration which bridges the aneurysm neck after distal and proximal portions of the mesh (or framework) have been longitudinally collapsed toward each other; one or more central openings (2003 and 2004) in the mesh (or framework); and embolic coils (or other embolic members) 2006 which are delivered via a catheter 2005 and inserted through the one or more openings into the aneurysm.

The upper left quadrant of FIG. 20 shows this device at a first point in time wherein the mesh (or framework) has a longitudinal first configuration and is being delivered from a catheter into an aneurysm. The upper right quadrant of FIG. 20 shows this device at a second point in time wherein the mesh (or framework) has a single-layer globular second configuration after it has been radially-expanded within the aneurysm. The lower left quadrant of FIG. 20 shows this device at a third point in time wherein the mesh (or framework) has a double-layer bowl-shaped third configuration which bridges the aneurysm neck after distal and proximal areas of the mesh (or framework) have been longitudinally collapsed toward each other. The lower right quadrant of FIG. 20 shows this device at a fourth point in time wherein embolic coils have been inserted into the aneurysm sac through one or more openings in the mesh (or framework) in its bowl-shaped configuration.

In an example, a mesh (or framework) in its bowl-shaped configuration can be a section of a sphere or ellipsoid. In an example, a mesh in its bowl-shaped configuration can be hemispherical. In an example, an opening can be between 5% to 15% of the maximum cross-sectional area of a mesh in its bowl-shaped configuration. In an example, an opening can be between 10% to 30% of the maximum cross-sectional area of a mesh in its bowl-shaped configuration. In an example, a mesh in its bowl-shaped configuration can be represented geometrically by rotating an arc of a circle or ellipse around a vertical axis (in space) which is to the right or left of the circle or ellipse. In an example, a mesh in its bowl-shaped configuration can radially expand within the aneurysm sac to a width which is greater than the width of the aneurysm neck. In an example, a mesh can have a single layer when it is in its first and second configurations, but have a double layer when it is in its third configuration. In an example, a mesh can have more layers in its third configuration than in its first and second configurations. In an example, a string-of-pearls embolic member or a plurality of separate embolic members (e.g. microsponges or hydrogels) can be inserted into the aneurysm instead of embolic coils.

In an example, a mesh (or framework) in its bowl-shaped configuration can have uniform porosity. In an example, a mesh in its bowl-shaped configuration can have a uniform durometer level. In an example, a mesh in its bowl-shaped configuration can have uniform elasticity. In an example, the outer perimeter of a mesh in its bowl-shaped configuration can have greater porosity than the central portion of the mesh in its bowl-shaped configuration. In an example, the outer perimeter of a mesh in its bowl-shaped configuration can have a greater durometer level than the central portion of the mesh in its bowl-shaped configuration. In an example, the outer perimeter of a mesh in its bowl-shaped configuration can be more elastic than the central portion of the mesh in its bowl-shaped configuration. In an example, the outer perimeter of a mesh in its bowl-shaped configuration can have lower porosity than the central portion of the mesh in its bowl-shaped configuration. In an example, the outer perimeter of a mesh in its bowl-shaped configuration can have a lower durometer level than the central portion of the mesh in its bowl-shaped configuration. In an example, the outer perimeter of a mesh in its bowl-shaped configuration can be less elastic than the central portion of the mesh in its bowl-shaped configuration.

In an example, a mesh (or framework) can self-expand into its globular second configuration. In an example, a mesh can be longitudinally-compressed into its bowl-shaped third configuration by movement of a wire, thread, and/or filament. In an example, a mesh can be longitudinally-compressed into its bowl-shaped third configuration when a device operator pulls on a wire, thread, and/or filament. In an example, a mesh can be longitudinally-compressed into its bowl-shaped third configuration by the application of electromagnetic energy. In an example, a mesh can be longitudinally-compressed into its bowl-shaped third configuration when a device operator delivers electromagnetic energy to the mesh. In an example, a mesh can be longitudinally-compressed into its bowl-shaped third configuration by movement of a catheter. In an example, a mesh can be longitudinally-compressed into its bowl-shaped third configuration by a hydraulic or pneumatic actuator. In an example, a mesh can be longitudinally-compressed into its bowl-shaped third configuration by one or more microscale actuators (e.g. MEMS).

FIG. 21 shows an intrasacular device for occluding a cerebral aneurysm comprising: a half-torus mesh 2101 which is configured to be radially-expanded within an aneurysm to bridge the aneurysm neck; a valve 2102 in the half-torus mesh; and a catheter 2103 through which embolic members (e.g. coils, hydrogels, microsponges, beads, or string-of-pearls strands) are inserted through the valve into the aneurysm. After the embolic members have been inserted, the valve is closed and the catheter is removed.

In an example, a half-torus mesh can have the shape of the lower surface of the lower half of a torus. This is analogous to the lower surface of a half of a bagel lying flat on a surface. In an example, the cross-sectional area of the valve can be between 5% to 15% of the maximum cross-sectional area of the half-torus mesh. In an example, the cross-sectional area of the valve can be between 10% to 30% of the maximum cross-sectional area of the half-torus mesh. In an example, a half-torus mesh can be created geometrically by rotating an upward-opening arc (e.g. a section of a circle, ellipsoid, or parabola) around a vertical axis (in space) which is to the right or left of the arc. In an example, a central portion of a half-torus mesh can comprise an upward-rising cone, analogous to the cone of a volcano, with the valve being where the crater of a volcano would be. In an example, the half-torus mesh can radially-expand within the aneurysm sac to a width which is greater than the width of the aneurysm neck.

In an example, a half-torus mesh can have uniform porosity. In an example, a half-torus mesh can have a uniform durometer level. In an example, a half-torus mesh can have uniform elasticity. In an example, the outer perimeter of a half-torus mesh can have greater porosity than the central portion of a half-torus mesh. In an example, the outer perimeter of a half-torus mesh can have a greater durometer level than the central portion of a half-torus mesh. In an example, the outer perimeter of a half-torus mesh can be more elastic than the central portion of a half-torus mesh. In an example, the outer perimeter of a half-torus mesh can have lower porosity than the central portion of a half-torus mesh. In an example, the outer perimeter of a half-torus mesh can have a lower durometer level than the central portion of a half-torus mesh. In an example, the outer perimeter of a half-torus mesh can be less elastic than the central portion of a half-torus mesh.

In an example, a half-torus mesh can be a wire mesh and/or frame. In an example, a half-torus mesh can have a single layer. In an example, a half-torus mesh can have two or more layers. In an example, a half-torus mesh can be a woven or braided wire mesh and/or frame. In an example, a half-torus mesh can be cut from metal. In an example, a half-torus mesh can be made from metal and polymer components. In an example, a half-torus mesh can comprise a wire frame and a polymer mesh. In an example, a half-torus mesh can comprise a wire frame and a polymer layer. In an example, a half-torus mesh can be made from nitinol.

In an example, a valve can be in the cross-sectional center of the half-torus mesh. In an example, a valve can be a leaflet valve. In an example, a valve can be a bi-leaflet valve or tri-leaflet valve, analogous to a heart valve. In an example, a valve can passively open when an embolic member is pushed through it and can passively close after the member passes through or when a portion of the member is detached. In an example, such a valve allows an embolic member to be inserted into an aneurysm after the half-torus mesh has been expanded in the aneurysm, but the valve closes to reduce blood flow into the aneurysm after the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

FIG. 22 shows an intrasacular device for occluding a cerebral aneurysm comprising: a toroidal mesh 2201 which is configured to be radially-expanded within an aneurysm to bridge the aneurysm neck; a valve 2202 in the toroidal mesh; and a catheter 2203 through which embolic members (e.g. coils, hydrogels, microsponges, beads, or string-of-pearls strands) are inserted through the valve into the aneurysm.

After the embolic members have been inserted, the valve is closed and the catheter is removed.

In an example, a toroidal mesh can have the shape of the outer surface of a torus. This is analogous to the outer surface of a bagel. In an example, the cross-sectional area of the valve can be between 5% to 15% of the maximum cross-sectional area of the toroidal mesh. In an example, the cross-sectional area of the valve can be between 10% to 30% of the maximum cross-sectional area of the toroidal mesh. In an example, a toroidal mesh can be created geometrically by rotating a circle or ellipsoid around a vertical axis (in space) which is to the right or left of the circle or ellipsoid. In an example, a central portion of a toroidal mesh can have a hyperbolic shape. In an example, the toroidal mesh can radially-expand within the aneurysm sac to a width which is greater than the width of the aneurysm neck.

In an example, a toroidal mesh can have uniform porosity. In an example, a toroidal mesh can have a uniform durometer level. In an example, a toroidal mesh can have uniform elasticity. In an example, the outer perimeter of a toroidal mesh can have greater porosity than the central portion of a toroidal mesh. In an example, the outer perimeter of a toroidal mesh can have a greater durometer level than the central portion of a toroidal mesh. In an example, the outer perimeter of a toroidal mesh can be more elastic than the central portion of a toroidal mesh. In an example, the outer perimeter of a toroidal mesh can have lower porosity than the central portion of a toroidal mesh. In an example, the outer perimeter of a toroidal mesh can have a lower durometer level than the central portion of a toroidal mesh. In an example, the outer perimeter of a toroidal mesh can be less elastic than the central portion of a toroidal mesh.

In an example, a toroidal mesh can be a wire mesh and/or frame. In an example, a toroidal mesh can have a single layer. In an example, a toroidal mesh can have two or more layers. In an example, a toroidal mesh can be a woven or braided wire mesh and/or frame. In an example, a toroidal mesh can be cut from metal. In an example, a toroidal mesh can be made from metal and polymer components. In an example, a toroidal mesh can comprise a wire frame and a polymer mesh. In an example, a toroidal mesh can comprise a wire frame and a polymer layer. In an example, a toroidal mesh can be made from nitinol.

In an example, a valve can be in the cross-sectional center of the toroidal mesh. In an example, a valve can be in a hyperbolic opening through the toroidal mesh. In an example, a valve can be a leaflet valve. In an example, a valve can be a bi-leaflet valve or tri-leaflet valve, analogous to a heart valve. In an example, a valve can passively open when an embolic member is pushed through it and can passively close after the member passes through or when a portion of the member is detached. In an example, such a valve allows an embolic member to be inserted into an aneurysm after the toroidal mesh has been expanded in the aneurysm, but the valve closes to reduce blood flow into the aneurysm after the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

FIG. 23 shows an intrasacular device for occluding a cerebral aneurysm comprising: a bowl-shaped mesh 2301 which is configured to be radially-expanded within an aneurysm to bridge the aneurysm neck; a valve 2302 in the bowl-shaped mesh; and a catheter 2303 through which embolic members (e.g. coils, hydrogels, microsponges, beads, or string-of-pearls strands) are inserted through the valve into the aneurysm. After the embolic members have been inserted, the valve is closed and the catheter is removed.

In an example, a bowl-shaped mesh can be shaped like a lower section of a sphere or ellipsoid. In an example, a bowl-shaped mesh can have a hemi-spherical or hemi-ellipsoidal shape. In an example, a bowl-shaped mesh can be a wire mesh and/or frame. In an example, a bowl-shaped mesh can have a single layer. In an example, a bowl-shaped mesh can have two or more layers. In an example, a bowl-shaped mesh can be a woven or braided wire mesh and/or frame. In an example, a bowl-shaped mesh can be cut from metal. In an example, a bowl-shaped mesh can be made from metal and polymer components. In an example, a bowl-shaped mesh can comprise a wire frame and a polymer mesh. In an example, a bowl-shaped mesh can comprise a wire frame and a polymer layer. In an example, a bowl-shaped mesh can be made from nitinol. In an example, the bowl-shaped mesh can radially-expand within the aneurysm sac to a width which is greater than the width of the aneurysm neck.

In an example, a bowl-shaped mesh can have uniform porosity. In an example, a bowl-shaped mesh can have a uniform durometer level. In an example, a bowl-shaped mesh can have uniform elasticity. In an example, the outer perimeter of a bowl-shaped mesh can have greater porosity than the central portion of a bowl-shaped mesh. In an example, the outer perimeter of a bowl-shaped mesh can have a greater durometer level than the central portion of a bowl-shaped mesh. In an example, the outer perimeter of a bowl-shaped mesh can be more elastic than the central portion of a bowl-shaped mesh. In an example, the outer perimeter of a bowl-shaped mesh can have lower porosity than the central portion of a bowl-shaped mesh. In an example, the outer perimeter of a bowl-shaped mesh can have a lower durometer level than the central portion of a bowl-shaped mesh. In an example, the outer perimeter of a bowl-shaped mesh can be less elastic than the central portion of a bowl-shaped mesh.

In an example, a valve can be in the cross-sectional center of a bowl-shaped mesh. In an example, a valve can be in a hyperbolic-shaped opening through a bowl-shaped mesh. In an example, the cross-sectional area of a valve can be between 5% to 15% of the maximum cross-sectional area of the bowl-shaped mesh. In an example, the cross-sectional area of a valve can be between 10% to 30% of the maximum cross-sectional area of the bowl-shaped mesh. In an example, a valve can be a leaflet valve. In an example, a valve can be a bi-leaflet valve or tri-leaflet valve, analogous to a heart valve.

In an example, a valve can passively open when an embolic member is pushed through it and can passively close after the member passes through or when a portion of the member is detached. In an example, such a valve allows an embolic member to be inserted into an aneurysm after the bowl-shaped mesh has been expanded in the aneurysm, but the valve closes to reduce blood flow into the aneurysm after the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

FIG. 24 shows an intrasacular device for occluding a cerebral aneurysm comprising: a hyperbolic (or dumbbell or hour-glass) shaped mesh 2401 which is configured to be radially-expanded within an aneurysm to bridge the aneurysm neck; a valve 2402 in the hyperbolic shaped mesh; and a catheter 2403 through which embolic members (e.g. coils, hydrogels, microsponges, beads, or string-of-pearls strands) are inserted through the valve into the aneurysm. After the embolic members have been inserted, the valve is closed and the catheter is removed.

In an example, a hyperbolic (or dumbbell or hour-glass) shaped mesh can be a wire mesh and/or frame. In an example, a hyperbolic shaped mesh can have a single layer. In an example, a hyperbolic shaped mesh can have two or more layers. In an example, a hyperbolic shaped mesh can be a woven or braided wire mesh and/or frame. In an example, a hyperbolic shaped mesh can be cut from metal. In an example, a hyperbolic shaped mesh can be made from metal and polymer components. In an example, a hyperbolic shaped mesh can comprise a wire frame and a polymer mesh. In an example, a hyperbolic shaped mesh can comprise a wire frame and a polymer layer. In an example, a hyperbolic shaped mesh can be made from nitinol. In an example, the hyperbolic shaped mesh can radially-expand within the aneurysm sac to a width which is greater than the width of the aneurysm neck.

In an example, a hyperbolic (or dumbbell or hour-glass) shaped mesh can have uniform porosity. In an example, a hyperbolic (or dumbbell or hour-glass) shaped mesh can have a uniform durometer level. In an example, a hyperbolic shaped mesh can have uniform elasticity. In an example, the outer perimeter of a hyperbolic shaped mesh can have greater porosity than the central portion of a hyperbolic shaped mesh. In an example, the outer perimeter of a hyperbolic shaped mesh can have a greater durometer level than the central portion of a hyperbolic shaped mesh. In an example, the outer perimeter of a hyperbolic shaped mesh can be more elastic than the central portion of a hyperbolic shaped mesh. In an example, the outer perimeter of a hyperbolic shaped mesh can have lower porosity than the central portion of a hyperbolic shaped mesh. In an example, the outer perimeter of a hyperbolic shaped mesh can have a lower durometer level than the central portion of a hyperbolic shaped mesh. In an example, the outer perimeter of a hyperbolic shaped mesh can be less elastic than the central portion of a hyperbolic shaped mesh.

In an example, a valve in a hyperbolic (or dumbbell or hour-glass) shaped mesh can be off-center. In an example, a valve in a hyperbolic shaped mesh can be offset from the central longitudinal axis of the mesh. In an example, there can be two or more off-center valves through a hyperbolic mesh. In an example, the cross-sectional area of a valve can be between 5% to 15% of the maximum cross-sectional area of the hyperbolic shaped mesh. In an example, the cross-sectional area of a valve can be between 10% to 30% of the maximum cross-sectional area of the hyperbolic shaped mesh. In an example, a valve can be a leaflet valve. In an example, a valve can be a bi-leaflet valve or tri-leaflet valve, analogous to a heart valve.

In an example, a valve can passively open when an embolic member is pushed through it and can passively close after the member passes through or when a portion of the member is detached. In an example, such a valve allows an embolic member to be inserted into an aneurysm after the hyperbolic (or dumbbell or hour-glass) shaped mesh has been expanded in the aneurysm, but the valve closes to reduce blood flow into the aneurysm after the embolic member has passed through the valve. In an alternative example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

FIG. 25 shows an intrasacular device for occluding a cerebral aneurysm comprising: an inner convex mesh 2501 which is configured to be radially-expanded within an aneurysm; an outer convex mesh (or net) 2502 which is configured to be radially-expanded within the aneurysm, wherein the inner convex mesh is inside the outer convex mesh; a valve 2503 in the outer convex mesh (or net); and a catheter 2504 through which embolic members (e.g. coils, hydrogels, microsponges, beads, or string-of-pearls strands) are inserted into the space between the inner convex mesh and the outer convex mesh. After the embolic members have been inserted, the valve is closed and the catheter is removed.

In an example, an inner convex mesh can be spherical. In an example, an inner convex mesh can be ellipsoidal. In an example, an inner convex mesh can be apple, barrel, or pear shaped. In an example, an inner convex mesh can be toroidal. In an example, an inner convex mesh can be hyperbolic, dumbbell, peanut, or hour-glass shaped. In an example, an inner convex mesh can be disk shaped. In an example, an inner convex mesh can be shaped like a paper lantern. In an example, an inner convex mesh can be a wire mesh and/or frame. In an example, an inner convex mesh can be a woven or braided wire mesh and/or frame. In an example, an inner convex mesh can be made from metal and polymer components. In an example, an outer convex mesh (or net) can be spherical. In an example, an outer convex mesh can be ellipsoidal. In an example, an outer convex mesh can be apple, barrel, or pear shaped. In an example, an outer convex mesh can be shaped like a paper lantern. In an example, an outer convex mesh can be a wire mesh and/or frame. In an example, an outer convex mesh can be a woven or braided wire mesh and/or frame.

In an example, an outer convex mesh (or net) can be made from metal and polymer components. In an example, an inner convex mesh can be made from a metal and an outer convex mesh can be made from a polymer. In an example, inner and outer convex meshes can be nested. In an example, inner and outer convex meshes can be concentric. In an example, inner and outer convex meshes can be attached to each other. In an example, the proximal ends of inner and outer convex meshes can be attached to each other. In an example, the distal ends of inner and outer convex meshes can be attached to each other. In an example: the proximal ends of inner and outer convex meshes can be attached to each other; and the distal ends of inner and outer convex meshes can be attached to each other.

In an example, inner and outer convex meshes can both have the same durometer level. In an example, inner and outer convex meshes can both have the same elasticity. In an example, inner and outer convex meshes can both have the same porosity. In an example, an outer convex mesh (or net) can be less elastic than an inner convex mesh. In an example, an outer convex mesh can have a greater durometer level than an inner convex mesh. In an example, an outer convex mesh can have greater porosity than an inner convex mesh. In an example, an outer convex mesh can be more elastic than an inner convex mesh. In an example, an outer convex mesh can have a lower durometer level an inner convex mesh. In an example, an outer convex mesh can have lower porosity than an inner convex mesh.

In an example, a valve in an outer convex mesh (or net) can be off-center. In an example, a valve in an outer convex mesh (or net) can be offset from the central longitudinal axis of the mesh. In an example, there can be two or more off-center valves through a outer convex mesh. Alternatively, a valve in an outer convex mesh can be central to the cross-section of an outer convex mesh. In an example, a valve in an outer convex mesh can on the central longitudinal axis of the mesh. In an example, the cross-sectional area of a valve can be between 5% to 15% of the maximum cross-sectional area of an outer convex mesh. In an example, the cross-sectional area of a valve can be between 10% to 30% of the maximum cross-sectional area of an outer convex mesh. In an example, a valve can be a leaflet valve. In an example, a valve can be a bi-leaflet valve or tri-leaflet valve, analogous to a heart valve.

In an example, a valve can passively open when an embolic member is pushed through it and can passively close after the member passes through or when a portion of the member is detached. In an example, such a valve allows an embolic member to be inserted into an aneurysm, but the valve closes to reduce blood flow into the aneurysm after the embolic member has passed through the valve. In an example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

FIG. 26 shows an intrasacular device for occluding a cerebral aneurysm comprising: a metal mesh (or frame) 2601 which is configured to be radially-expanded within an aneurysm; a polymer net (or liner) 2602 which is configured to be radially-expanded within the aneurysm, wherein the metal mesh is inside the polymer net; a valve 2603 in the polymer net; and a catheter 2604 through which embolic members (e.g. coils, hydrogels, microsponges, beads, or string-of-pearls strands) are inserted into the space between the metal mesh and the polymer net. After the embolic members have been inserted, the valve is closed and the catheter is removed.

In an example, a metal mesh (or frame) can be spherical. In an example, a metal mesh can be ellipsoidal. In an example, a metal mesh can be apple, barrel, or pear shaped. In an example, a metal mesh can be toroidal. In an example, a metal mesh can be hyperbolic, dumbbell, peanut, or hour-glass shaped. In an example, a metal mesh can be disk shaped. In an example, a metal mesh can be shaped like a paper lantern. In an example, a metal mesh can be a wire mesh and/or frame. In an example, a metal mesh can be a woven or braided wire mesh and/or frame. In an example, a metal mesh can be a ball stent. In an example, a metal mesh can be made from metal and polymer components. In an example, a polymer net can be spherical. In an example, a polymer net can be ellipsoidal. In an example, a polymer net can be apple, barrel, or pear shaped. In an example, a polymer net can be shaped like a paper lantern. In an example, a polymer net can be a wire mesh and/or frame. In an example, a polymer net can be a woven or braided wire mesh and/or frame.

In an example, a polymer net can be made from metal and polymer components. In an example, a metal mesh can be made from a metal and a polymer net can be made from a polymer. In an example, a metal mesh and a polymer net can be nested. In an example, metal mesh and polymer net can be concentric. In an example, a metal mesh and a polymer net can be attached to each other. In an example, the proximal end of a metal mesh and the proximal end of a polymer net can be attached to each other. In an example, the distal end of a metal mesh and the distal end of a polymer net can be attached to each other. In an example: the proximal end of a metal mesh and the proximal end of a polymer net can be attached to each other; and the proximal end of a metal mesh and the proximal end of a polymer net can be attached to each other.

In an example, a metal mesh and a polymer net can both have the same durometer level. In an example, a metal mesh and a polymer net can both have the same elasticity. In an example, a metal mesh and a polymer net can both have the same porosity. In an example, a polymer net can be less elastic than a metal mesh. In an example, a polymer net can have a greater durometer level than a metal mesh. In an example, a polymer net can have greater porosity than a metal mesh. In an example, a polymer net can be more elastic than a metal mesh. In an example, a polymer net can have a lower durometer level a metal mesh. In an example, a polymer net can have lower porosity than a metal mesh.

In an example, a valve in a polymer net can be off-center. In an example, a valve in a polymer net can be offset from the central longitudinal axis of the net. In an example, there can be two or more off-center valves through a polymer net. Alternatively, a valve in a polymer net can be central to the cross-section of the polymer net. In an example, a valve in a polymer net can on the central longitudinal axis of the net. In an example, the cross-sectional area of a valve can be between 5% to 15% of the maximum cross-sectional area of a polymer net. In an example, the cross-sectional area of a valve can be between 10% to 30% of the maximum cross-sectional area of a polymer net. In an example, a valve can be a leaflet valve. In an example, a valve can be a bi-leaflet valve or tri-leaflet valve, analogous to a heart valve.

In an example, a valve can passively open when an embolic member is pushed through it and can passively close after the member passes through or when a portion of the member is detached. In an example, such a valve allows an embolic member to be inserted into an aneurysm, but the valve closes to reduce blood flow into the aneurysm after the embolic member has passed through the valve. In an example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 27:
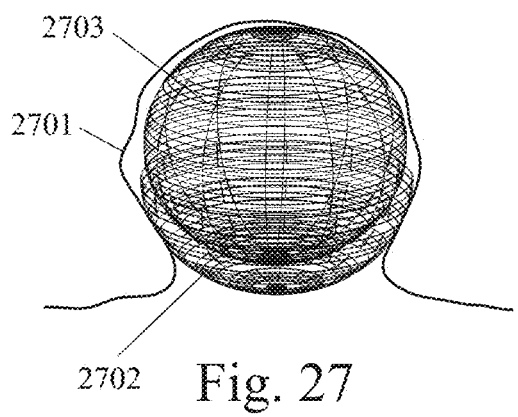
FIG. 27 shows an intrasacular aneurysm occlusion device with a proximal bowl-shaped mesh and a distal globular mesh.

FIG. 27 shows an intrasacular device for occluding a cerebral aneurysm comprising: a distal mesh 2703 which is configured to be radially-expanded within the dome of an aneurysm 2701; and a proximal mesh 2702 which is configured to be radially-expanded to bridge the neck of the aneurysm; wherein a proximal portion of the distal mesh is nested within a concavity of the proximal mesh, wherein proximal means closer to the aneurysm neck, and wherein distal means farther from the aneurysm neck.

In an example, a proximal portion of a distal mesh can fit inside a distal concavity of a proximal mesh. In an example, a proximal portion of a distal mesh can be nested within a distal concavity of a proximal mesh. In an example, a proximal mesh can overlap a proximal portion of a distal mesh. In an example, between 20% and 40% of the surface of a distal mesh can be nested within a concavity of a proximal mesh. In an example, between 30% and 66% of the surface of a distal mesh can be nested within a concavity of a proximal mesh. In an example, distal and proximal meshes can be coaxial. In an example, the distal mesh and the proximal mesh can share a common longitudinal axis. In an example, a proximal portion of a distal mesh can be attached to a proximal mesh. In an example, a proximal portion of a distal mesh can be fused to a portion of the proximal mesh by the application of electromagnetic energy. In an example, a proximal portion of a distal mesh can be attached to a portion of a proximal mesh by a wire, string, suture, or other filament.

In an example, a distal mesh can be globular. In an example, a distal mesh can be spherical. In an example, a distal mesh can be ellipsoidal. In an example, a distal mesh can be disk shaped. In an example, a distal mesh can be toroidal. In an example, a distal mesh can be apple, barrel, or pear shaped. In an example, a distal mesh can be hyperbolic, hour-glass, dumbbell, or peanut shaped. In an example, a distal mesh can be shaped like a paper lantern. In an example, a proximal mesh can be a portion of a sphere or ellipsoid. In an example, a proximal mesh can be bowl shaped. In an example, a proximal mesh can be hemispherical. In an example, a proximal mesh can be parabolic. In an example, a proximal mesh can be a conic section.

In an example, a proximal mesh can be expanded to a diameter which is greater than the diameter of an aneurysm neck. In an example, a proximal mesh can be expanded to a diameter which is at least 90% of the maximum diameter of an aneurysm sac. In an example, a proximal mesh can be expanded to a circumference which is greater than the circumference of an aneurysm neck. In an example, a proximal mesh can be expanded to a circumference which is at least 90% of the maximum circumference of an aneurysm sac. In an example, a distal mesh can be expanded to a diameter which is between 90% and 100% of the diameter of a proximal mesh. In an example, a proximal mesh can be expanded to a circumference which is between 90% and 100% of the circumference of a proximal mesh.

In an example, a distal mesh can be a wire mesh. In an example, a distal mesh can be a wire frame. In an example, a distal mesh can be a stent. In an example, a distal mesh can be woven or braided. In an example, a distal mesh can be made from metal. In an example, a distal mesh can be made from a polymer. In an example, a distal mesh can be made from both metal and polymer components. In an example, a proximal mesh can be a wire mesh. In an example, a proximal mesh can be a wire frame. In an example, a proximal mesh can be a stent. In an example, a proximal mesh can be woven or braided. In an example, a proximal mesh can be made from metal. In an example, a proximal mesh can be made from a polymer. In an example, a proximal mesh can be made from both metal and polymer components.

In an example, proximal and distal meshes can both have the same durometer level. In an example, proximal and distal meshes can both have the same elasticity. In an example, proximal and distal meshes can both have the same porosity. In an example, a distal mesh can be less elastic than a proximal mesh. In an example, a distal mesh can have a greater durometer level than a proximal mesh. In an example, a distal mesh can have greater porosity than a proximal mesh. In an example, a distal mesh can be more elastic than a proximal mesh. In an example, a distal mesh can have a lower durometer level a proximal mesh. In an example, a distal mesh can have lower porosity than a proximal mesh.

Figure 28:
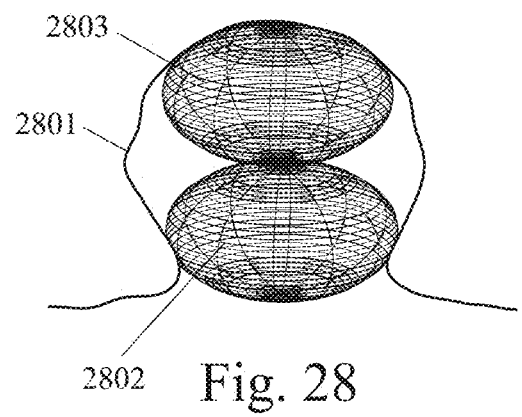
FIG. 28 shows an intrasacular aneurysm occlusion device with a proximal convex mesh and a distal convex mesh.

FIG. 28 shows an intrasacular device for occluding a cerebral aneurysm comprising: a distal mesh 2803 which is configured to be radially-expanded within the dome of an aneurysm 2801; and a proximal mesh 2802 which is configured to be radially-expanded to bridge the neck of the aneurysm; wherein the proximal end of the distal mesh is attached to the distal end of the proximal mesh, wherein proximal means closer to the aneurysm neck, and wherein distal means farther from the aneurysm neck. In an example, distal and proximal meshes can be coaxial. In an example, the distal mesh and the proximal mesh can share a common longitudinal axis. In an example, the proximal end of a distal mesh can be fused to the distal end of the proximal mesh by the application of electromagnetic energy. In an example, the proximal end of a distal mesh can be attached to the distal end of the proximal mesh by a wire, string, suture, or other filament.

In an example, both proximal and distal meshes can be ellipsoidal. In an example, both proximal and distal meshes can be spherical. In an example, a distal mesh can be spherical. In an example, a proximal mesh can be spherical. In an example, a distal mesh can be apple, barrel, or pear shaped. In an example, a proximal mesh can be apple, barrel, or pear shaped. In an example, both proximal and distal meshes can be apple, barrel, or pear shaped. In an example, a distal mesh can be disk shaped. In an example, a proximal mesh can be disk shaped. In an example, both proximal and distal meshes can be disk shaped. In an example, a distal mesh can be ellipsoidal. In an example, a proximal mesh can be ellipsoidal.

In an example, both proximal and distal meshes can be globular. In an example, a distal mesh can be globular. In an example, a proximal mesh can be globular. In an example, a distal mesh can be hyperbolic, hour-glass, dumbbell, or peanut shaped. In an example, a proximal mesh can be hyperbolic, hour-glass, dumbbell, or peanut shaped. In an example, both proximal and distal meshes can be hyperbolic, hour-glass, dumbbell, or peanut shaped. In an example, a distal mesh can be shaped like a paper lantern. In an example, a proximal mesh can be shaped like a paper lantern. In an example, both proximal and distal meshes can be shaped like a paper lantern. In an example, a distal mesh can be toroidal. In an example, a proximal mesh can be toroidal. In an example, both proximal and distal meshes can be toroidal.

In an example, both proximal and distal meshes can be the same size. In an example, a proximal mesh can be larger than a distal mesh. In an example, a proximal mesh can be between 10% and 30% larger than a distal mesh. In an example, a proximal mesh can be between 25% and 75% larger than a distal mesh. In an example, a distal mesh can be a wire mesh. In an example, a distal mesh can be a wire frame. In an example, a distal mesh can be a stent. In an example, a distal mesh can be woven or braided. In an example, a distal mesh can be made from metal. In an example, a distal mesh can be made from a polymer.

In an example, a distal mesh can be made from both metal and polymer components. In an example, a proximal mesh can be a wire mesh. In an example, a proximal mesh can be a wire frame. In an example, a proximal mesh can be a stent. In an example, a proximal mesh can be woven or braided. In an example, a proximal mesh can be made from metal. In an example, a proximal mesh can be made from a polymer. In an example, a proximal mesh can be made from both metal and polymer components. In an example, a distal mesh can be larger than a proximal mesh. In an example, a distal mesh can be between 10% and 30% larger than a proximal mesh. In an example, a distal mesh can be between 25% and 75% larger than a proximal mesh.

In an example, proximal and distal meshes can both have the same durometer level. In an example, proximal and distal meshes can both have the same elasticity. In an example, proximal and distal meshes can both have the same porosity. In an example, a distal mesh can be less elastic than a proximal mesh. In an example, a distal mesh can have a greater durometer level than a proximal mesh. In an example, a distal mesh can have greater porosity than a proximal mesh. In an example, a distal mesh can be more elastic than a proximal mesh. In an example, a distal mesh can have a lower durometer level a proximal mesh. In an example, a distal mesh can have lower porosity than a proximal mesh.

Figure 29:
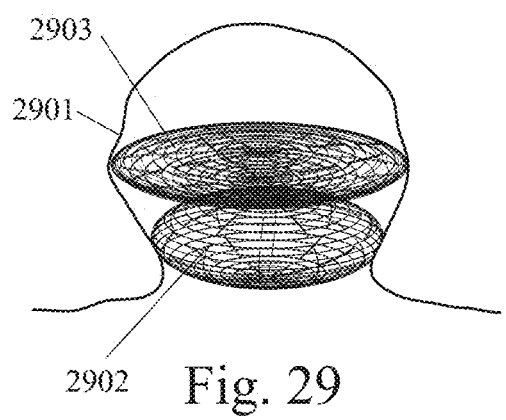
FIG. 29 shows an intrasacular aneurysm occlusion device with a proximal disk mesh and a distal disk mesh.

FIG. 29 shows an intrasacular device for occluding a cerebral aneurysm comprising: a distal mesh 2903 which is configured to be radially-expanded within the sac of an aneurysm 2901; and a proximal mesh 2902 which is configured to be radially-expanded to bridge the neck of the aneurysm; wherein the proximal end of the distal mesh is attached to the distal end of the proximal mesh, wherein proximal means closer to the aneurysm neck, and wherein distal means farther from the aneurysm neck. In an example, distal and proximal meshes can be coaxial. In an example, the distal mesh and the proximal mesh can share a common longitudinal axis. In an example, the proximal end of a distal mesh can be fused to the distal end of the proximal mesh by the application of electromagnetic energy. In an example, the proximal end of a distal mesh can be attached to the distal end of the proximal mesh by a wire, string, suture, or other filament.

In an example, both proximal and distal meshes can be ellipsoidal. In an example, a distal mesh can be disk shaped. In an example, a proximal mesh can be disk shaped. In an example, both proximal and distal meshes can be disk shaped. In an example, a distal mesh can be ellipsoidal. In an example, a proximal mesh can be ellipsoidal. In an example, a distal mesh can be shaped like a paper lantern. In an example, a proximal mesh can be shaped like a paper lantern. In an example, both proximal and distal meshes can be shaped like a paper lantern. In an example, a distal mesh can be toroidal. In an example, a proximal mesh can be toroidal. In an example, both proximal and distal meshes can be toroidal.

In an example, both proximal and distal meshes can be the same size. In an example, a proximal mesh can be larger than a distal mesh. In an example, a proximal mesh can be between 10% and 30% larger than a distal mesh. In an example, a proximal mesh can be between 25% and 75% larger than a distal mesh. In an example, a distal mesh can be a wire mesh. In an example, a distal mesh can be a wire frame. In an example, a distal mesh can be a stent. In an example, a distal mesh can be woven or braided. In an example, a distal mesh can be made from metal. In an example, a distal mesh can be made from a polymer.

In an example, a distal mesh can be made from both metal and polymer components. In an example, a proximal mesh can be a wire mesh. In an example, a proximal mesh can be a wire frame. In an example, a proximal mesh can be a stent. In an example, a proximal mesh can be woven or braided. In an example, a proximal mesh can be made from metal. In an example, a proximal mesh can be made from a polymer. In an example, a proximal mesh can be made from both metal and polymer components. In an example, a distal mesh can be larger than a proximal mesh. In an example, a distal mesh can be between 10% and 30% larger than a proximal mesh. In an example, a distal mesh can be between 25% and 75% larger than a proximal mesh.

In an example, proximal and distal meshes can both have the same durometer level. In an example, proximal and distal meshes can both have the same elasticity. In an example, proximal and distal meshes can both have the same porosity. In an example, a distal mesh can be less elastic than a proximal mesh. In an example, a distal mesh can have a greater durometer level than a proximal mesh. In an example, a distal mesh can have greater porosity than a proximal mesh. In an example, a distal mesh can be more elastic than a proximal mesh. In an example, a distal mesh can have a lower durometer level a proximal mesh. In an example, a distal mesh can have lower porosity than a proximal mesh.

Figure 30:
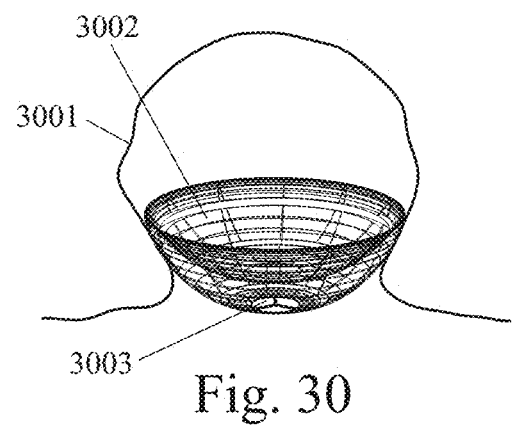
FIG. 30 shows an intrasacular aneurysm occlusion device comprising a double-layer bowl-shaped mesh with a valve through which embolic members are inserted.

FIG. 30 shows an intrasacular device for occluding a cerebral aneurysm comprising: a double-layer bowl-shaped mesh 3002 which is configured to be radially-expanded to bridge the neck of an aneurysm 3001; and a valve 3003 in the double-layer bowl-shaped mesh through which embolic members (e.g. embolic coils, hydrogels, microsponges, beads, or string-of-pearls embolic strands) or liquid embolic material (which solidifies in the aneurysm) can be inserted into the aneurysm.

In an example, a bowl-shaped mesh can have uniform elasticity. In an example, a bowl-shaped mesh can have uniform porosity. In an example, a bowl-shaped mesh can have a uniform durometer level. In an example, a central portion of a bowl-shaped mesh can have a greater durometer level than a peripheral portion of a bowl-shaped mesh. In an example, the outer perimeter of a bowl-shaped mesh can have a greater durometer level than the central portion of a bowl-shaped mesh. In an example, a central portion of a bowl-shaped mesh can have a lower durometer level a peripheral portion of a bowl-shaped mesh. In an example, the outer perimeter of a bowl-shaped mesh can have a lower durometer level than the central portion of a bowl-shaped mesh. In an example, layers of a bowl-shaped mesh can be closer together near the center of the bowl-shaped mesh and farther apart around the periphery of the bowl-shaped mesh.

In an example, a central portion of a bowl-shaped mesh can have greater porosity than a peripheral portion of a bowl-shaped mesh. In an example, the outer perimeter of a bowl-shaped mesh can have greater porosity than the central portion of a bowl-shaped mesh. In an example, a central portion of a bowl-shaped mesh can have lower porosity than a peripheral portion of a bowl-shaped mesh. In an example, the outer perimeter of a bowl-shaped mesh can have lower porosity than the central portion of a bowl-shaped mesh. In an example, a central portion of a bowl-shaped mesh can be more elastic than a peripheral portion of a bowl-shaped mesh. In an example, the outer perimeter of a bowl-shaped mesh can be more elastic than the central portion of a bowl-shaped mesh. In an example, the outer perimeter of a bowl-shaped mesh can be less elastic than the central portion of a bowl-shaped mesh. In an example, layers of a bowl-shaped mesh can be farther apart near the center of the bowl-shaped mesh and closer together in the periphery of the bowl-shaped mesh.

In an example, a valve in a bowl-shaped mesh can be central to the cross-section of the bowl-shaped mesh. In an example, the cross-sectional area of a valve can be between 5% to 15% of the maximum cross-sectional area of a bowl-shaped mesh. In an example, the cross-sectional area of a valve can be between 10% to 30% of the maximum cross-sectional area of a bowl-shaped mesh. In an example, a valve can be a leaflet valve. In an example, a valve can be a bi-leaflet valve or tri-leaflet valve, analogous to a heart valve.

In an example, a valve can passively open when an embolic member is pushed through it and can passively close after the member passes through or when a portion of the member is detached. In an example, such a valve allows an embolic member to be inserted into an aneurysm, but the valve closes to reduce blood flow into the aneurysm after the embolic member has passed through the valve. In an example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 31:
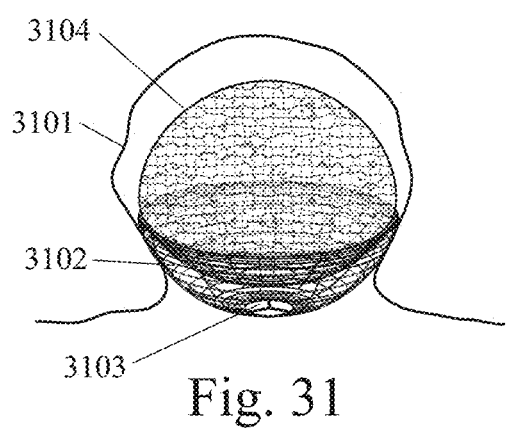
FIG. 31 shows an intrasacular aneurysm occlusion device comprising a proximal bowl-shaped mesh, a distal flexible net inside the concavity of the bowl, and a valve through which embolic members are inserted.

FIG. 31 shows an intrasacular device for occluding a cerebral aneurysm comprising: a proximal bowl-shaped mesh 3102 which is configured to be radially-expanded to bridge the neck of an aneurysm 3101; a distal flexible net (or mesh) 3104 which is nested within a concavity of the bowl-shaped mesh, wherein the distal flexible net expands to fill the dome of the aneurysm; and a valve 3103 in the proximal bowl-shaped mesh through which embolic members (e.g. embolic coils, hydrogels, microsponges, beads, or string-of-pearls embolic strands) pass into the distal flexible net. In an example, the distal flexible net and the proximal bowl-shaped mesh can be connected. In an example, the distal flexible net and the proximal bowl-shaped mesh can be centrally connected. In an example, the distal flexible net and the proximal bowl-shaped mesh can both be connected to the valve.

In an example, a valve in a bowl-shaped mesh can be central to the cross-section of the bowl-shaped mesh. In an example, a valve in a bowl-shaped mesh can on the central longitudinal axis of the distal flexible net. In an example, the cross-sectional area of a valve can be between 5% to 15% of the maximum cross-sectional area of a bowl-shaped mesh. In an example, the cross-sectional area of a valve can be between 10% to 30% of the maximum cross-sectional area of a bowl-shaped mesh. In an example, a valve can be a leaflet valve. In an example, a valve can be a bi-leaflet valve or tri-leaflet valve, analogous to a heart valve.

In an example, a valve can passively open when an embolic member is pushed through it and can passively close after the member passes through or when a portion of the member is detached. In an example, such a valve allows an embolic member to be inserted into the distal flexible net, but the valve closes to reduce blood flow after the embolic member has passed through the valve. In an example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 32:
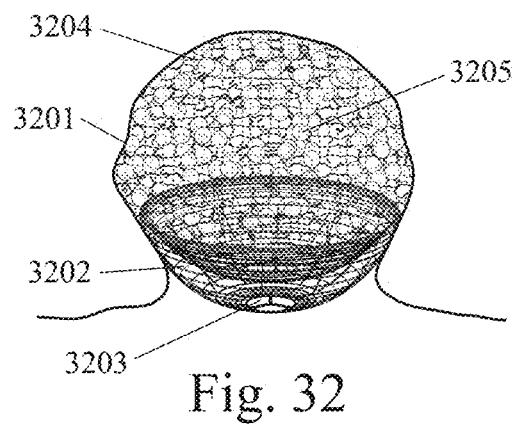
FIG. 32 shows an intrasacular aneurysm occlusion device comprising a proximal bowl-shaped mesh, a distal flexible net around the concavity of the bowl, and a valve through which embolic members are inserted.

FIG. 32 shows an intrasacular device for occluding a cerebral aneurysm comprising: a proximal bowl-shaped mesh 3202 which is configured to be radially-expanded to bridge the neck of an aneurysm 3201; a flexible net (or mesh) 3204 which expands to fill the dome of the aneurysm, wherein the proximal bowl-shaped mesh is inside the flexible net; and a valve 3203 in the flexible net through which embolic members (e.g. embolic coils, hydrogels, microsponges, beads, or string-of-pearls embolic strands) pass into the flexible net.

In an example, the flexible net and the proximal bowl-shaped mesh can be connected. In an example, the flexible net and the proximal bowl-shaped mesh can be centrally connected. In an example, the flexible net and the proximal bowl-shaped mesh can both be connected to the valve. In an example, the proximal bowl-shaped mesh can be made from metal and the flexible net (or mesh) can be made from a polymer. In an example, the composition of the proximal bowl-shaped mesh can have higher percentage of metal than the composition of the flexible net (or mesh). In an example the proximal bowl-shaped mesh can be less porous than the flexible net (or mesh). In an example the proximal bowl-shaped mesh can be less elastic than the flexible net (or mesh). In an example the proximal bowl-shaped mesh can have a lower durometer level than the flexible net (or mesh).

In an example, a valve can be a leaflet valve. In an example, a valve can be a bi-leaflet valve or tri-leaflet valve, analogous to a heart valve. In an example, a valve can passively open when an embolic member is pushed through it and can passively close after the member passes through or when a portion of the member is detached. In an example, such a valve allows an embolic member to be inserted into the flexible net, but the valve closes to reduce blood flow after the embolic member has passed through the valve. In an example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire. In an example, an active valve can be remotely opened and/or closed by an operator by cutting, pulling, or pushing a flap or plug.

Figure 33:
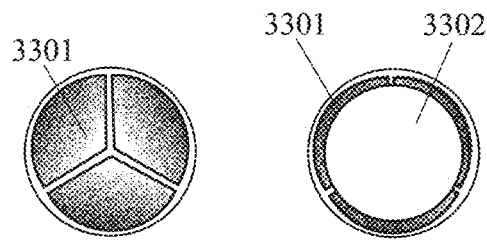
FIG. 33 shows a tri-leaflet valve through which embolic members are inserted into an aneurysm sac.

FIG. 33 shows two sequential views of an example of a leaflet valve which can be used in an intrasacular device for occluding a cerebral aneurysm. The left half of FIG. 33 shows this leaflet valve at a first point in time when the valve is in its closed configuration. The right half of FIG. 33 shows this leaflet valve at a second point in time when the valve is in its open configuration. Specifically, FIG. 33 shows a leaflet valve 3301 and a central opening 3302 in the valve (when it is in its open configuration).

This is just one type of valve which can be used in any of in the intrasacular devices shown elsewhere in this disclosure or priority-linked disclosures. In an example, this leaflet valve can be positioned in an opening (or lumen) through a mesh (or net) which bridges an aneurysm neck. When this leaflet valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this leaflet valve is in its closed configuration, it reduces blood flood through the opening in the mesh into the aneurysm. In other words, this leaflet valve can serve as a "closure mechanism" for an intrasacular aneurysm occlusion device.

In an example, a leaflet valve can be a bi-leaflet valve or tri-leaflet valve, analogous to a heart valve. In an example, a leaflet valve can have a single leaflet or flap. In an example, a leaflet valve can have four or more leaflets or flaps. In an example, a leaflet valve can passively open when an embolic member (such as an embolic coil, hydrogel, microsponge, bead, or a string-of-pearls embolic strand) pushes through it. In an example, a leaflet valve can passively close when after the embolic member has passed through. In an example, a leaflet valve can be made from an elastomeric material. In an example, a leaflet valve can be made from a silicone-based polymer. In an example, a leaflet valve can be made from rigid material such as metal. In an example, a leaflet valve can be made from titanium and carbon. In an example, a leaflet valve can be remotely opened and/or closed by the operator of the device. In an example, a leaflet valve can be remotely opened and/or closed by an operator by the application of electromagnetic energy.

Figure 34:
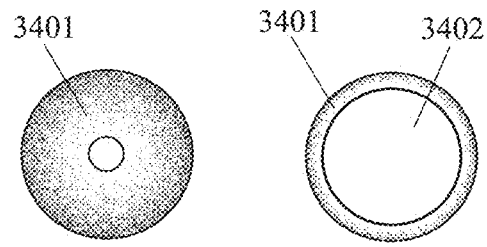
FIG. 34 shows an elastic annular valve through which embolic members are inserted into an aneurysm sac.

FIG. 34 shows two sequential views of an example of an elastic annular valve which can be used in an intrasacular device for occluding a cerebral aneurysm. The left half of FIG. 34 shows this elastic annular valve at a first point in time when the valve is in its closed configuration. The right half of FIG. 34 shows this elastic annular valve at a second point in time when the valve is in its open configuration. Specifically, FIG. 34 shows a leaflet elastic annular valve 3401 and a central opening 3402 in the valve (when it is in its open configuration).

This is just one type of valve which can be used in any of in the intrasacular devices shown elsewhere in this disclosure or priority-linked disclosures. In an example, this elastic annular valve can be positioned in an opening (or lumen) through a mesh (or net) which bridges an aneurysm neck. When this elastic annular valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this elastic annular valve is in its closed configuration, it reduces blood flood through the opening in the mesh into the aneurysm. In other words, this elastic annular valve can serve as a "closure mechanism" for an intrasacular aneurysm occlusion device. We all have times when we need closure.

In an example, a valve can be an elastic annular valve. In an example, an elastic annular valve can passively open when an embolic member (such as an embolic coil, hydrogel, microsponge, bead, or a string-of-pearls embolic strand) pushes through it. In an example, an elastic annular valve can passively close when after the embolic member has passed through. In an example, an elastic annular valve can be made from an elastomeric material. In an example, an elastic annular valve can be made from a silicone-based polymer.

Figure 35:
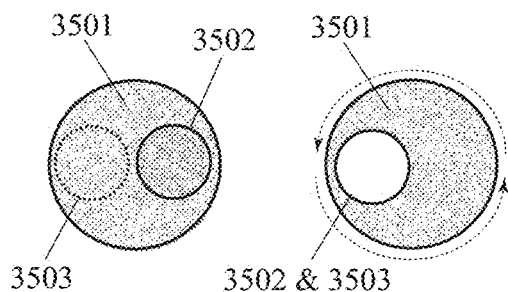
FIG. 35 shows a rotational valve through which embolic members are inserted into an aneurysm sac.

FIG. 35 shows two sequential views of an example of a rotational valve which can be used in an intrasacular device for occluding a cerebral aneurysm. The left half of FIG. 35 shows this rotational valve at a first point in time wherein the valve is in its closed configuration. The right half of FIG. 35 shows this rotational valve at a second point in time wherein the valve is in its open configuration. Specifically, the rotational valve shown in FIG. 35 comprises an (outer) first layer 3501 with a first opening (or hole) 3502 and an (inner) second layer with a second opening (or hole) 3503.

When the first and second openings (holes) are not aligned, then the valve is in its closed configuration. When the first and second openings (holes) are aligned, then the valve is in its open configuration. In this example, the valve is changed from its closed configuration to its open configuration, or vice versa, by rotating (or revolving, pivoting, turning, or twisting) the first layer relative to the second layer, or vice versa. In an example, a rotational valve can comprise two or more overlapping (e.g. parallel) layers with openings (holes). When the openings (holes) of different layers are not aligned, then the valve is closed. When the opening (holes) of different layers are aligned, then the valve is open. In an example, the valve can be opened or closed by rotating one layer relative to the other layer. In an example, one or both layers can be rotated remotely by the operator of the device, enabling the operator to open or close the valve remotely.

This is just one type of valve which can be used in any of in the intrasacular devices shown elsewhere in this disclosure or priority-linked disclosures. In an example, this rotational valve can be positioned in an opening (or lumen) through a mesh (or net) which bridges an aneurysm neck. When this rotational valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this rotational valve is in its closed configuration, it reduces blood flood through the opening in the mesh into the aneurysm. In other words, this rotational valve can serve as a "closure mechanism" for an intrasacular aneurysm occlusion device.

Figure 36:
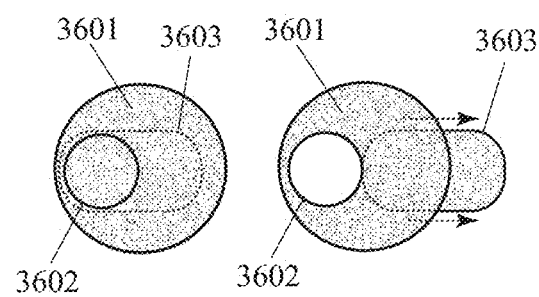
FIG. 36 shows a sliding valve through which embolic members are inserted into an aneurysm sac.

FIG. 36 shows two sequential views of an example of a sliding valve which can be used in an intrasacular device for occluding a cerebral aneurysm. The left half of FIG. 36 shows this sliding valve at a first point in time wherein the valve is in its closed configuration. The right half of FIG. 36 shows this sliding valve at a second point in time wherein the valve is in its open configuration. Specifically, the sliding valve shown in FIG. 36 comprises a layer 3601 with an opening (or hole) 3602 and a sliding flap (or lid) 3603. When the sliding flap (lid) covers the opening (hole), then the valve is in its closed configuration. When the sliding flap (lid) does not cover the opening (hole), then the valve is in its open configuration. In this example, the valve is changed from its closed configuration to its open configuration, or vice versa, by moving the sliding flap. In an example, the sliding flap can be moved remotely by the operator of the device, enabling the operator to open or close the valve remotely.

This is just one type of valve which can be used in any of in the intrasacular devices shown elsewhere in this disclosure or priority-linked disclosures. In an example, this sliding valve can be positioned in an opening (or lumen)

through a mesh (or net) which bridges an aneurysm neck. When this sliding valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this sliding valve is in its closed configuration, it reduces blood flood through the opening in the mesh into the aneurysm. In other words, this sliding valve can serve as a "closure mechanism" for an intrasacular aneurysm occlusion device.

Figure 37:
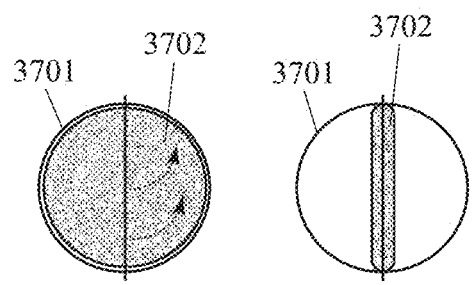
FIG. 37 shows a pivoting valve through which embolic members are inserted into an aneurysm sac.

FIG. 37 shows two sequential views of an example of a pivoting valve which can be used in an intrasacular device for occluding a cerebral aneurysm. The left half of FIG. 37 shows this pivoting valve at a first point in time wherein the valve is in its closed configuration. The right half of FIG. 37 shows this pivoting valve at a second point in time wherein the valve is in its open configuration. Specifically, the valve shown in FIG. 37 comprises a lumen (opening) 3701 with a pivoting flap (or plug) 3702. When the pivoting flap (plug) blocks the lumen (opening), then the valve is in its closed configuration. When the pivoting flap (lid) does not block the lumen (opening), then the valve is in its open configuration. In this example, the valve is changed from its closed configuration to its open configuration, or vice versa, by pivoting (rotating) the flap around a central axis. In the example of a square opening, a valve could changed from its closed configuration to its open configuration, or vice versa, by pivoting (rotating) a flap around one side. In an example, the pivoting flap can be moved remotely by the operator of the device, enabling the operator to open or close the valve remotely. This type of pivoting valve is analogous to the valves which are used in circular air ducts for HVAC (heating, ventilation, and air conditioning) systems in buildings.

This is just one type of valve which can be used in any of in the intrasacular devices shown elsewhere in this disclosure or priority-linked disclosures. In an example, this pivoting valve can be positioned in an opening (or lumen) through a mesh (or net) which bridges an aneurysm neck. When this pivoting valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. This type of pivoting valve is more appropriate for liquid embolic material than for coils, beads, or string-of-pearls strands which might get snagged on it. When this pivoting valve is in its closed configuration, it reduces blood flood through the opening in the mesh into the aneurysm. In other words, this pivoting valve can serve as a "closure mechanism" for an intrasacular aneurysm occlusion device. We all have times when we need closure.

Figure 38:
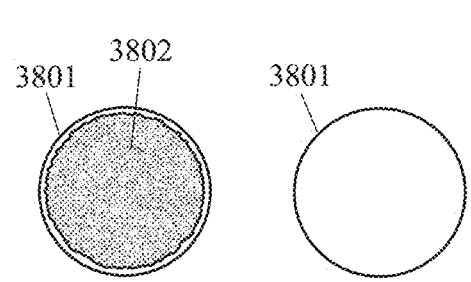
FIG. 38 shows a plug-mechanism valve through which embolic members are inserted into an aneurysm sac.

FIG. 38 shows two sequential views of a plug mechanism which can be used in an intrasacular device for occluding a cerebral aneurysm. The left half of FIG. 38 shows this plug mechanism at a first point in time, in its closed configuration. The right half of FIG. 38 shows this plug mechanism at a second point in time, in its open configuration. Specifically, the plug mechanism shown in FIG. 38 comprises a lumen (opening) 3801 and a plug 3802 which is inserted into the lumen. When a plug blocks the lumen (opening), then the plug mechanism is in its closed configuration. When a plug does not block the lumen (opening), then the plug mechanism is in its open configuration. In this example, the plug mechanism is changed from its open configuration to its closed configuration by inserting a plug into the lumen (opening). In an example, a plug can be inserted remotely by the operator of the device, enabling the operator to close the plug mechanism remotely. In an example, a plug can be inserted into a lumen by using a guidewire or hydraulic pressure. In an example, a plug can be made from hydrogel.

This plug mechanism is just one type of closure mechanism which can be used in any of in the intrasacular devices shown elsewhere in this disclosure or priority-linked disclosures. In an example, this plug mechanism can be positioned in an opening (or lumen) through a mesh (or net) which bridges an aneurysm neck. When this plug mechanism is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this plug mechanism is in its closed configuration, it reduces blood flood through the opening in the mesh into the aneurysm.

In an example, a "string-of-pearls" embolic member can be a component of an intrasacular aneurysm occlusion device. In an example, a "string-of-pearls" embolic member can be inserted into a flexible net or mesh within an aneurysm sac. Alternatively, a "string-of-pearls" embolic member alone can be directly inserted into an aneurysm sac. A "string-of-pearls" embolic member can be defined as a longitudinal series of bead-like embolic "pearls" (e.g. not actual pearls, but rather bead-like embolic masses) which are connected by a flexible longitudinal "string" (e.g. a flexible strand, thread, filament, suture, tube, or wire).

In an example, pearls in a string-of-pearls embolic member can be convex. In an example, pearls can be globular, spherical, and/or ellipsoidal. In an example, pearls can be polyhedral. In an example, pearls in a string-of-pearls embolic member can be concave. In an example, pearls can be beads. In an example, pearls can be hard. In an example, pearls can have a durometer level greater than 50. In an example, pearls can be soft. In an example, pearls can have a durometer level less than 20. In an example, pearls can have a durometer level less than 10. In an example, pearls can be compressed while traveling through a catheter and can expand after insertion into an aneurysm. In an example, pearls can expand between 100% and 400% upon their insertion into an aneurysm. In an example, pearls can have a first average size while they travel through a catheter and a second average size after expansion in an aneurysm sac, wherein the second average size is between 2-5 times the first average size. In an example, pearls can be microsponges or gels. In an example, pearls can be hydrogels.

In an example, a string in a string-of-pearls embolic member can be a flexible polymer strand, thread, suture, or filament. In an example, a string can be a flexible metal wire, tube, or filament. In an example, a string can be an organic thread or yarn. In an example, a longitudinal series of pearls can be centrally connected by a string. In an example, a longitudinal series of pearls can be connected by two or more strings. In an example, a string in a string-of-pearls embolic member can be undulating and/or sinusoidal. In an example, a string in a string-of-pearls embolic member can be helical. In an example, a string in a string-of-pearls embolic member can be a helical wire and/or coil.

In an example, pearls in a string-of-pearls embolic member can be (pair-wise) equidistant from each other. In an example, a string-of-pearls embolic member can comprise an equidistant longitudinal series of pearls connected by a string. In an example, pearls in a distal portion of a string-of-pearls can be closer together than pearls in a proximal portion of the string-of-pearls, wherein the distal portion is first inserted into the aneurysm sac. In an example, pearls in a distal portion of a string-of-pearls can be a first average distance apart and pearls in a proximal portion of the string-of-pearls can be second distance apart, wherein the second distance is greater than the first distance. In an example, pearls in a distal portion of a string-of-pearls can be farther apart than pearls in a proximal portion of the string-of-pearls, wherein the distal portion is first inserted into the aneurysm sac. In an example, pearls in a distal portion of a string-of-pearls can be a first average distance apart and pearls in a proximal portion of the string-of-pearls can be second distance apart, wherein the second distance is less than the first distance. In an example, the average length of string segments connecting pairs of pearls in a string-of-pearls embolic member can be between 1 and 10 times the average size (e.g. diameter) of the pearls.

In an example, pearls in a string-of-pearls embolic member can all be the same size (e.g. diameter). In an example, pearls in a distal portion of a string-of-pearls can be larger than pearls in a proximal portion of a string-of-pearls, wherein the distal portion is first inserted into the aneurysm sac. In an example, pearls in a distal portion of a string-of-pearls can be have a first average size (e.g. diameter) and pearls in a proximal portion of the string-of-pearls can have a second average size (e.g. diameter), wherein the second average size is less than the first average size. In an example, pearls in a distal portion of a string-of-pearls can be smaller than pearls in a proximal portion of a string-of-pearls, wherein the distal portion is first inserted into the aneurysm sac. In an example, pearls in a distal portion of a string-of-pearls can be have a first average size (e.g. diameter) and pearls in a proximal portion of the string-of-pearls can have a second average size (e.g. diameter), wherein the second average size is greater than the first average size.

In an example, pearls in a string-of-pearls embolic member can all have the same durometer level. In an example, pearls in a distal portion of a string-of-pearls can have a higher durometer level than pearls in a proximal portion of a string-of-pearls, wherein the distal portion is first inserted into the aneurysm sac. In an example, pearls in a distal portion of a string-of-pearls can be have a first durometer level and pearls in a proximal portion of the string-of-pearls can have a second durometer level, wherein the second durometer level is less than the first durometer level. In an example, pearls in a distal portion of a string-of-pearls can have a lower durometer level than pearls in a proximal portion of a string-of-pearls, wherein the distal portion is first inserted into the aneurysm sac. In an example, pearls in a distal portion of a string-of-pearls can be have a first durometer level and pearls in a proximal portion of the string-of-pearls can have a second durometer level, wherein the second durometer level is greater than the first durometer level.

In an example, pearls in a string-of-pearls embolic member can have an average size which is greater than the average size of openings in a flexible net or mesh into which the pearls are inserted. In an example, pearls in a string-of-pearls embolic member can have an average size which is between 1 and 5 times the average size of openings in a flexible net or mesh. In an example, the average length of string segments connecting pearls in a string-of-pearls embolic member can be between 1 and 10 times the average size of pearls in a string-of-pearls embolic member. In an example, the average length of string segments connecting pearls in a string-of-pearls embolic member can be between 1 and 10 times the average size of openings in a flexible net or mesh. In an example, a string in a string-of-pearls embolic member can be made from twine and the pearls can be flow into the sac before the string. However, it is probably not a good idea to flow pearls before twine.

In an example, a string-of-pearls embolic member can be delivered through a catheter by means of a liquid flow and/or fluid pressure. In an example, a string-of-pearls embolic member can be delivered through a catheter by means of a guide wire and/or pusher wire. In an example, a string-of-pearls embolic member can be delivered through a catheter by means of a conveyor belt mechanism which engages and moves the "pearl" components. In an example, a series of pre-formed separate string-of-pearls embolic members can be sequentially inserted into an aneurysm. In an example, the length of a string-of-pearls embolic member can be selected by a device operator during deployment by a cutting and/or detaching mechanism which the operator uses to cut and/or detach he string-of-pearls embolic member at a selected location during deployment into an aneurysm.

In an example, a volume-measuring mechanism can track the cumulative volume of a string-of-pearls embolic member as it is progressively inserted into an aneurysm sac. In an example, this cumulative volume can be compared to an estimated volume of the aneurysm sac based on prior medical imaging. In an example, the three-dimensional volume of an aneurysm sac can be estimated based on three-dimensional medical imaging and the cumulative volume of a string-of-pearls embolic member which is inserted in the aneurysm sac can be based on this three-dimensional volume of the aneurysm sac. In an example, a string-of-pearls embolic member can be progressively inserted into an aneurysm sac until the cumulative volume of the string-of-pearls embolic member which has been inserted into the sac is at least 60% of the estimated volume of the aneurysm sac. In an example, a string-of-pearls embolic member can be progressively inserted into an aneurysm sac until the cumulative volume of the string-of-pearls embolic member which has been inserted into the sac is at least 80% of the estimated volume of the aneurysm sac. In an example, a string-of-pearls embolic member can be progressively inserted into an aneurysm sac until the cumulative volume of the string-of-pearls embolic member which has been inserted into the sac is between 60% and 95% of the estimated volume of the aneurysm sac.

Figure 39:
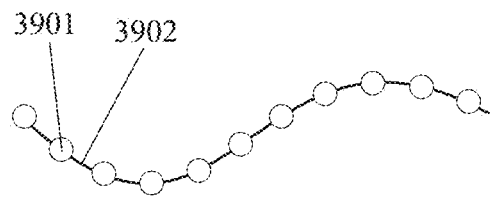
FIG. 39 shows a "string-of-pearls" embolic member comprising embolic pearls (e.g. bead-like polymer, hydrogel, or metal masses) connected by a flexible longitudinal string (e.g. a flexible strand, thread, filament, tube, or wire).

FIG. 39 shows an example of a "string-of-pearls" embolic member. This "string-of-pearls" embolic member can be used in one of the aneurysm occlusion devices which is discussed elsewhere in this disclosure or priority-linked disclosures. Specifically, FIG. 39 shows a string-of-pearls embolic member comprising: a longitudinal series of embolic pearls (e.g. bead-like polymer, hydrogel, or metal masses) including 3901, wherein the embolic pearls are connected to each other in a series by a flexible longitudinal string (e.g. a flexible strand, thread, filament, tube, or wire) 3902, and wherein pearls in the longitudinal series are pair-wise equidistant from each other.

Figure 40:
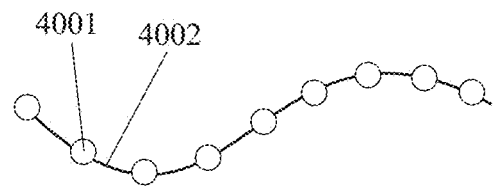
FIG. 40 shows a "string-of-pearls" embolic member wherein pearls in a distal portion of a longitudinal series are father apart than pearls in a proximal portion of the longitudinal series.

FIG. 40 shows an example of a "string-of-pearls" embolic member. This "string-of-pearls" embolic member can be used in one of the aneurysm occlusion devices which is discussed elsewhere in this disclosure or priority-linked disclosures. Specifically, FIG. 40 shows a string-of-pearls embolic member comprising: a longitudinal series of embolic pearls (e.g. bead-like polymer, hydrogel, or metal masses) including 4001, wherein the embolic pearls are connected to each other in a series by a flexible longitudinal string (e.g. a flexible strand, thread, filament, tube, or wire) 4002, wherein pearls in a distal portion of the longitudinal series are a first average distance from each other, wherein pearls in a proximal portion of the longitudinal series are a second average distance from each other, and wherein the second average distance is less than the first average distance.

Figure 41:
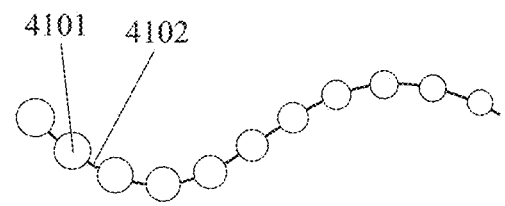
FIG. 41 shows a "string-of-pearls" embolic member wherein pearls in a distal portion of the longitudinal series are larger than pearls in a proximal portion of the longitudinal series.

FIG. 41 shows an example of a "string-of-pearls" embolic member. This "string-of-pearls" embolic member can be used in one of the aneurysm occlusion devices which is discussed elsewhere in this disclosure or priority-linked disclosures. Specifically, FIG. 41 shows a string-of-pearls embolic member comprising: a longitudinal series of embolic pearls (e.g. bead-like polymer, hydrogel, or metal masses) including 4101, wherein the embolic pearls are connected to each other in a series by a flexible longitudinal string (e.g. a flexible strand, thread, filament, tube, or wire) 4102, wherein pearls in a distal portion of the longitudinal series are a first average size, wherein pearls in a proximal portion of the longitudinal series are a second average size, and wherein the second average size is less than the first average size.

Figure 42:
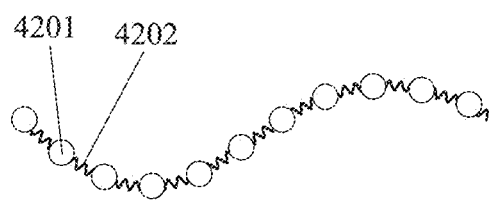
FIG. 42 shows a "string-of-pearls" embolic member with an undulating, sinusoidal, or helical string.

FIG. 42 shows an example of a "string-of-pearls" embolic member. This "string-of-pearls" embolic member can be used in one of the aneurysm occlusion devices which is discussed elsewhere in this disclosure or priority-linked disclosures. Specifically, FIG. 42 shows a string-of-pearls embolic member comprising: a longitudinal series of embolic pearls (e.g. bead-like polymer, hydrogel, or metal masses) including 4201, wherein the embolic pearls are connected to each other in a series by a flexible longitudinal string (e.g. a flexible strand, thread, filament, tube, or wire) 4202, wherein the flexible longitudinal string is undulating, sinusoidal, or helical.

Figure 43:
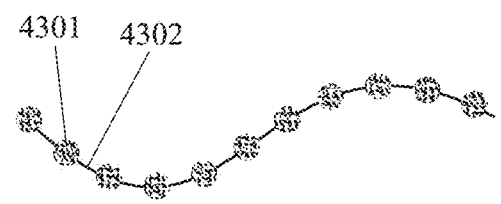
FIG. 43 shows a "string-of-pearls" embolic member with soft, compressible embolic pearls.

FIG. 43 shows an example of a "string-of-pearls" embolic member. This "string-of-pearls" embolic member can be used in one of the aneurysm occlusion devices which is discussed elsewhere in this disclosure or priority-linked disclosures. Specifically, FIG. 43 shows a string-of-pearls embolic member comprising: a longitudinal series of soft, compressible embolic pearls including 4301, wherein the embolic pearls are connected to each other in a series by a flexible longitudinal string (e.g. a flexible strand, thread, filament, tube, or wire) 4302.

Figure 44:
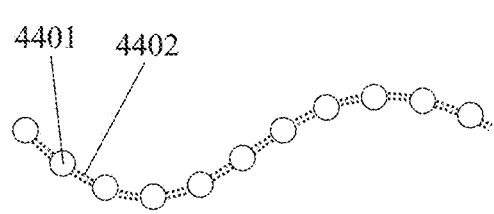
FIG. 44 shows a "string-of-pearls" embolic member wherein embolic pearls are connected by two flexible longitudinal strings.

FIG. 44 shows an example of a "string-of-pearls" embolic member. This "string-of-pearls" embolic member can be used in one of the aneurysm occlusion devices which is discussed elsewhere in this disclosure or priority-linked disclosures. Specifically, FIG. 44 shows a string-of-pearls embolic member comprising: a longitudinal series of embolic pearls (e.g. bead-like polymer, hydrogel, or metal masses) including 4401, wherein the embolic pearls are connected to each other in a series by two flexible longitudinal strings (e.g. a flexible strands, threads, filaments, tubes, or wires) including 4402.

Figure 45:
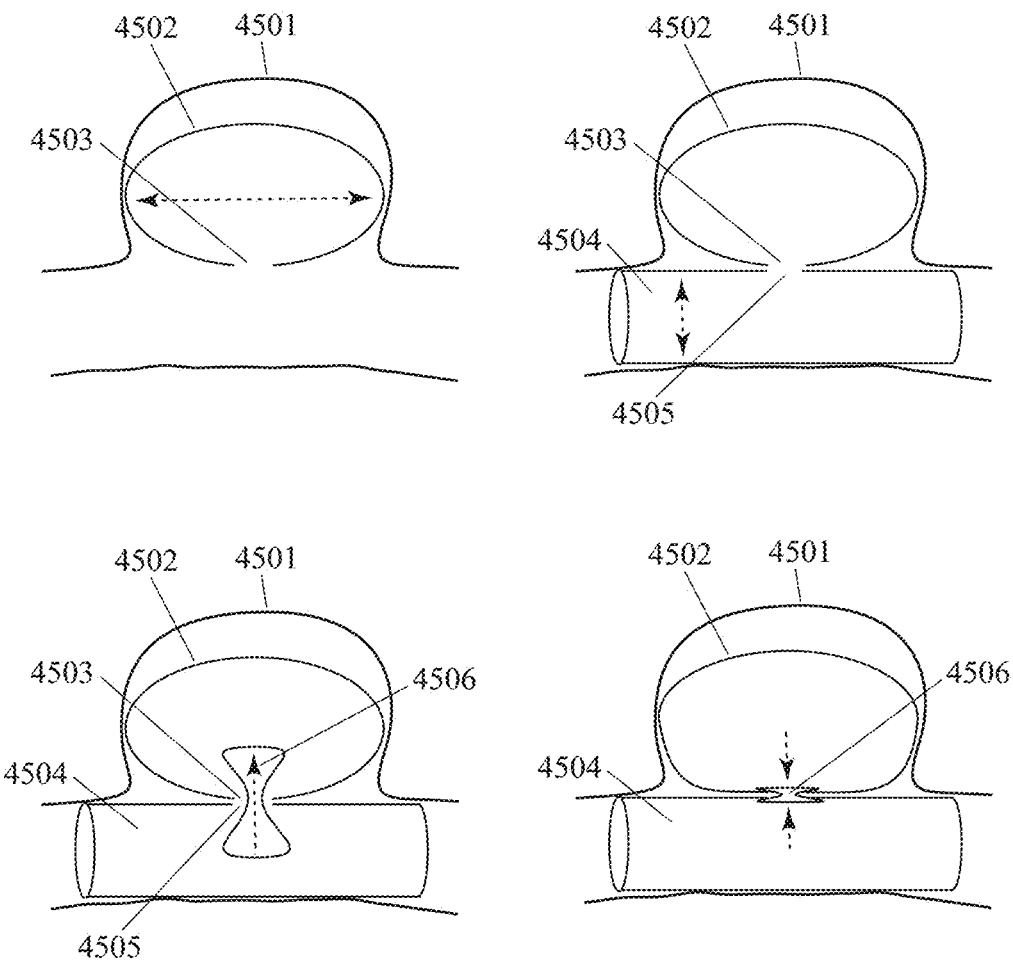
FIG. 45 shows an aneurysm occlusion device comprising a globular mesh in an aneurysm sac and a stent in the parent vessel, wherein the mesh and the stent are connected.

FIG. 45 shows four sequential views of a device for occluding a cerebral aneurysm comprising: a globular (e.g. spherical or ellipsoidal) mesh 4502 which is configured to be radially expanded in an aneurysm 4501, wherein there is a mesh wall opening 4503 in a proximal portion of the wall of the globular mesh; a stent 4504 which is configured to be radially expanded in a parent vessel of the aneurysm, wherein there is a stent wall opening 4505 in the wall of the stent, and wherein the stent wall opening is aligned with the mesh wall opening; and an hourglass shaped (or hyperbolic, dumbbell, or peanut shaped) mesh 4506 which is inserted into the mesh wall and stent wall openings and then longitudinally-compressed (e.g. like a rivet) in order to attach the globular mesh and the stent to each other.

The upper left quadrant of FIG. 45 shows this device at a first point in time wherein the globular mesh is being radially expanded within an aneurysm. The upper right quadrant of FIG. 45 shows this device at a second point in time wherein the stent is being radially expanded within the parent vessel of the aneurysm. The lower left quadrant of FIG. 45 shows this device at a third point in time wherein the hourglass shaped mesh is being inserted into the mesh wall and stent wall openings. The lower right quadrant of FIG. 45 shows this device at a fourth point in time wherein the hourglass shaped mesh is being longitudinally compressed in order to attach the globular mesh and the stent to each other. In an variation on this example, the globular mesh and the stent can be fused to each other by the application of electromagnetic energy instead of by the compression of an hourglass mesh.

Figure 46:
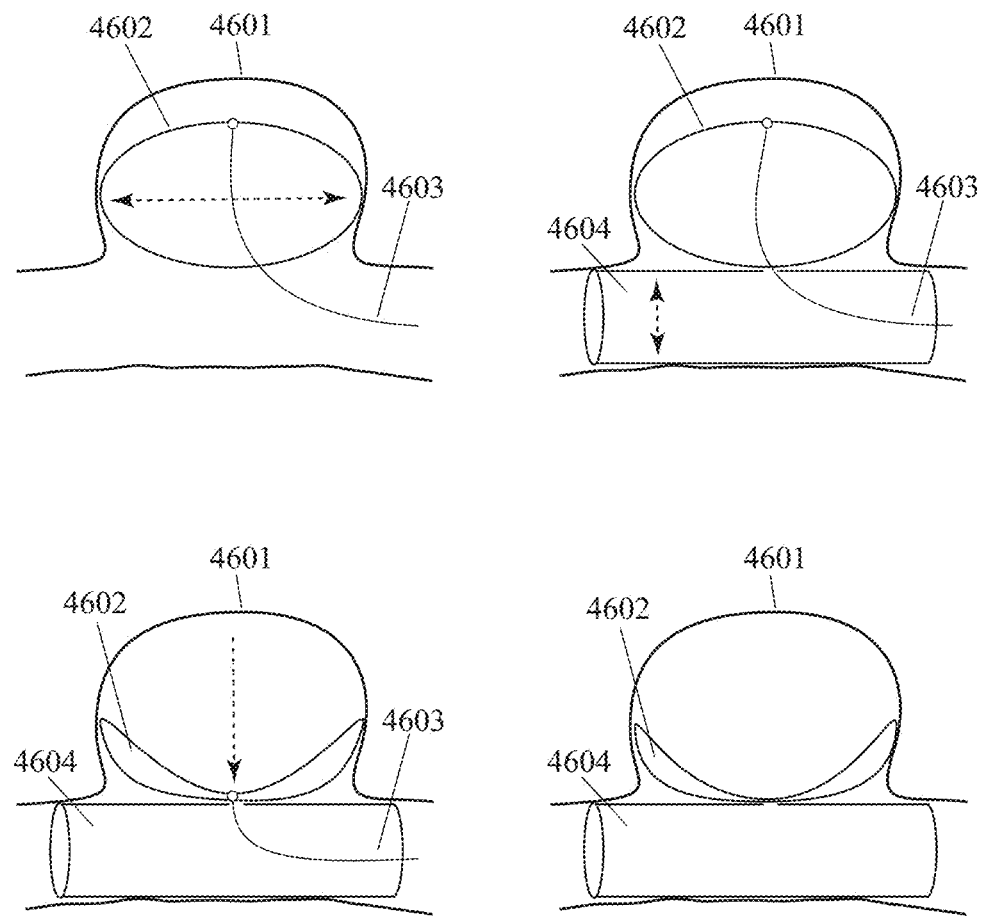
FIG. 46 shows an aneurysm occlusion device comprising a collapsed globular mesh in an aneurysm sac and a stent in the parent vessel.

FIG. 46 shows four sequential views of a device for occluding a cerebral aneurysm comprising: a globular (e.g. spherical or ellipsoidal) mesh 4602 which is configured to be radially expanded in an aneurysm 4601; a wire (or filament, string, or thread) 4603 which is attached to a distal portion of the globular mesh; and a stent 4604 which is configured to be radially expanded in a parent vessel of the aneurysm, wherein the distal portion of the globular mesh is collapsed toward the proximal portion of the globular mesh when the wire is pulled. In a variation on this wording, FIG. 46 also shows a device for occluding a cerebral aneurysm comprising: a globular (e.g. spherical or ellipsoidal) mesh which is configured to be radially expanded in an aneurysm; a wire (or filament, string, or thread) which is attached to a distal portion of the globular mesh; and a stent which is configured to be radially expanded in a parent vessel of the aneurysm, wherein the distal portion of the globular mesh is collapsed toward the stent when the wire is pulled.

The upper left quadrant of FIG. 46 shows this device at a first point in time wherein the globular mesh is being radially expanded within an aneurysm. The upper right quadrant of FIG. 46 shows this device at a second point in time wherein the stent is being radially expanded within the parent vessel of the aneurysm. The lower left quadrant of FIG. 46 shows this device at a third point in time wherein the wire is pulling the distal portion of the globular mesh toward the proximal portion of the globular mesh (and also toward the stent). In an example, the globular mesh can have a first (pre-collapse) configuration which is generally spherical or ellipsoidal and a second (post-collapse) configuration which is generally hemispherical and/or bowl-shaped. The lower right quadrant of FIG. 45 shows this device at a fourth point in time after the wire has been detached and removed.

Figure 47:
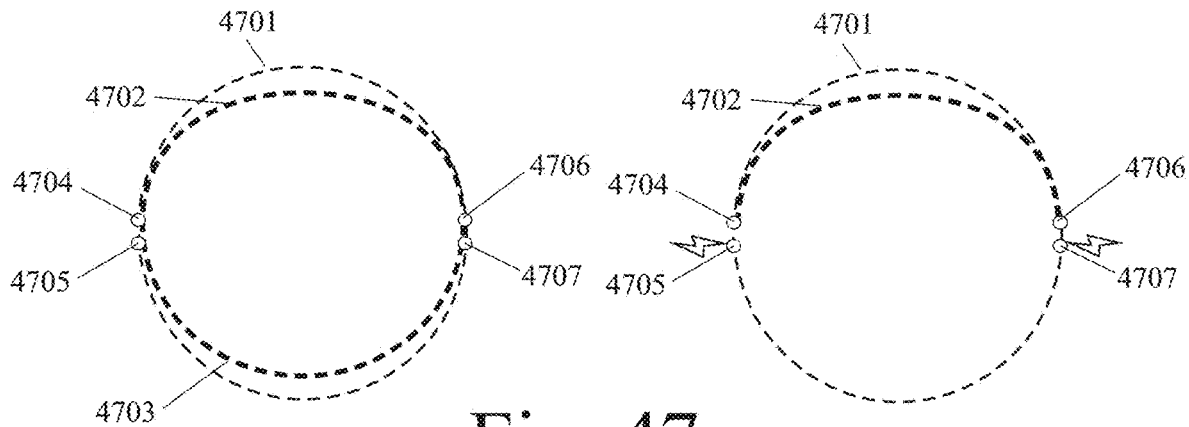
FIG. 47 shows a parent-vessel aneurysm occlusion device with removable partially-circumferential meshes inside a tubular mesh.

FIG. 47 shows two sequential cross-sectional views of a device for occluding a cerebral aneurysm comprising: a longitudinal tubular mesh (e.g. a stent) 4701 which is configured to be inserted into the parent vessel of an aneurysm; a first inner mesh 4702 which is inside the central cavity of the longitudinal tubular mesh, which overlaps a first portion (e.g. a first side) of the circumference of the longitudinal tubular mesh, and which is attached to the longitudinal tubular mesh by one or more connections 4704 and 4706; and a second inner mesh 4703 which is inside the central cavity of the longitudinal tubular mesh, which overlaps a second portion (e.g. a second side) of the circumference of the longitudinal tubular mesh, and which is attached to the longitudinal tubular mesh by one or more connections 4705 and 4707.

In an example, the one or more connections between an inner mesh (e.g. either the first inner mesh or the second inner mesh) which is farther from the aneurysm neck are detached and that inner mesh is removed after the device has been deployed in the parent vessel of an aneurysm. This causes the side of the longitudinal tubular mesh which is closer to the aneurysm neck to have a lower porosity than the side of the longitudinal tubular mesh which is farther from the aneurysm neck. The left side of FIG. 47 shows this device at a first point in time wherein both of the inner meshes are attached to the longitudinal tubular mesh. The right side of FIG. 47 shows this device at a second point in time wherein one of the inner meshes (e.g. the one farther from the aneurysm neck) has been detached and removed. In this example, connections have been melted (e.g. detached) by the application of electromagnetic energy.

Figure 48:
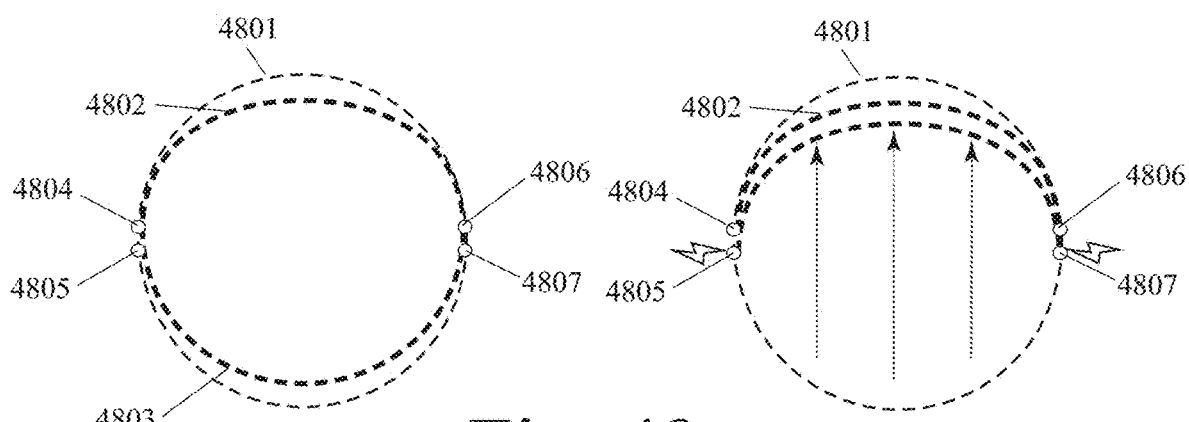
FIG. 48 shows a first example of a parent-vessel aneurysm occlusion device with movable partially-circumferential meshes inside a tubular mesh.

FIG. 48 shows two sequential cross-sectional views of a device for occluding a cerebral aneurysm comprising: a longitudinal tubular mesh (e.g. a stent) 4801 which is configured to be inserted into the parent vessel of an aneurysm; a first inner mesh 4802 which is inside the central cavity of the longitudinal tubular mesh, wherein the first inner mesh has a first configuration which overlaps a first portion (e.g. a first side) of the circumference of the longitudinal tubular mesh, wherein the first inner mesh can have a second configuration which overlaps a second portion (e.g. a second side) of the circumference of the longitudinal tubular mesh, wherein the first inner mesh is in electromagnetic communication with one or more electrodes 4804 and 4806, and wherein application electromagnetic energy to first inner mesh causes it to change from the first configuration to the second configuration; and a second inner mesh 4803 which is inside the central cavity of the longitudinal tubular mesh, wherein the second inner mesh has a third configuration which overlaps the second portion (e.g. the second side) of the circumference of the longitudinal tubular mesh, wherein the second inner mesh can have a fourth configuration which overlaps the first portion (e.g. the first side) of the circumference of the longitudinal tubular mesh, wherein the second inner mesh is in electromagnetic communication with one or more electrodes 4805 and 4807, wherein application electromagnetic energy to the second inner mesh causes it to change from the third configuration to the fourth configuration.

In an example, the configuration of an inner mesh (e.g. either the first inner mesh or the second inner mesh) which is farther from the aneurysm neck is changed after the device has been deployed in the parent vessel of an aneurysm. This causes the side of the longitudinal tubular mesh which is closer to the aneurysm neck to have a lower porosity than the side of the longitudinal tubular mesh which is farther from the aneurysm neck. The left side of FIG. 48 shows this device at a first point in time before the configuration of one of the inner meshes has been changed. The right side of FIG. 48 shows this device at a second point in time after the configuration of one of the inner meshes has been changed by application of electromagnetic energy to electrodes. In this example, application of electromagnetic energy causes the curvature of an inner mesh to change direction (e.g. from convex to concave), thereby changing which side of the longitudinal tubular mesh it overlaps. In an example, a first inner mesh and/or a second inner mesh can be made from shape memory material whose curvature changes when exposed to electromagnetic energy.

Figure 49:
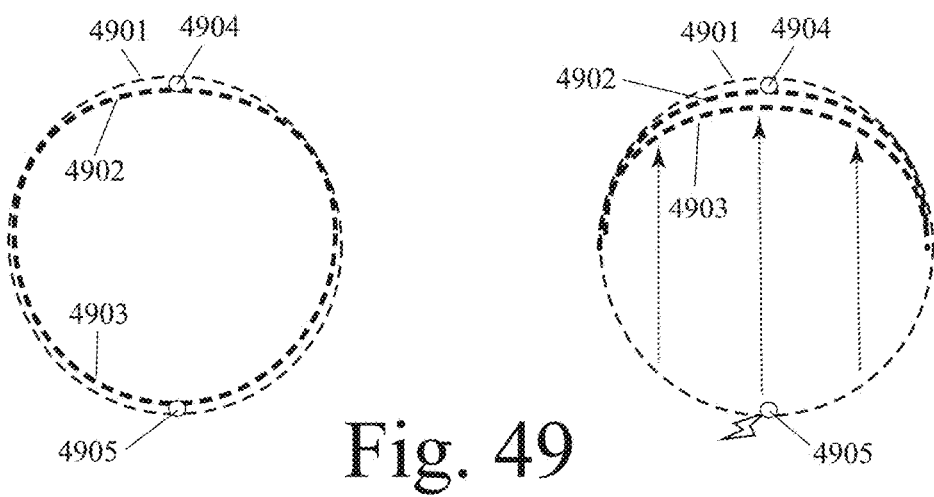
FIG. 49 shows a second example of a parent-vessel aneurysm occlusion device with movable partially-circumferential meshes inside a tubular mesh.

FIG. 49 shows two sequential cross-sectional views of a device for occluding a cerebral aneurysm comprising: a longitudinal tubular mesh (e.g. a stent) 4901 which is configured to be inserted into the parent vessel of an aneurysm; a first inner mesh 4902 which is inside the central cavity of the longitudinal tubular mesh, wherein the first inner mesh has a first configuration which overlaps a first portion (e.g. a first side) of the circumference of the longitudinal tubular mesh, wherein the first inner mesh has a second configuration which overlaps a second portion (e.g. a second side) of the circumference of the longitudinal tubular mesh, wherein the first inner mesh in its first configuration is attached to the longitudinal tubular mesh by connection 4904, wherein the first inner mesh is predisposed (e.g. biased) toward the second configuration but is held in the first configuration by connection 4904, wherein detachment of connection 4904 releases the first inner mesh from the first configuration to the second configuration; and a second inner mesh 4903 which is inside the central cavity of the longitudinal tubular mesh, wherein the second inner mesh has a third configuration which overlaps the second portion (e.g. the second side) of the circumference of the longitudinal tubular mesh, wherein the second inner mesh has a fourth configuration which overlaps the first portion (e.g. the first side) of the circumference of the longitudinal tubular mesh, wherein the second inner mesh in its third configuration is attached to the longitudinal tubular mesh by connection 4905, wherein the second inner mesh is predisposed (e.g. biased) toward the fourth configuration but is held in the third configuration by connection 4905, wherein detachment of connection 4905 releases the second inner mesh from the third configuration to the fourth configuration.

In an example, the configuration of an inner mesh (e.g. either the first inner mesh or the second inner mesh) which is farther from the aneurysm neck is changed after the device has been deployed in the parent vessel of an aneurysm. This causes the side of the longitudinal tubular mesh which is closer to the aneurysm neck to have a lower porosity than the side of the longitudinal tubular mesh which is farther from the aneurysm neck. The left side of FIG. 49 shows this device at a first point in time before the configuration of one of the inner meshes has been changed. The right side of FIG. 49 shows this device at a second point in time after the configuration of one of the inner meshes has been changed by detachment of a connection. In this example, detachment is done by applying electromagnetic energy to a connection.

Figure 50:
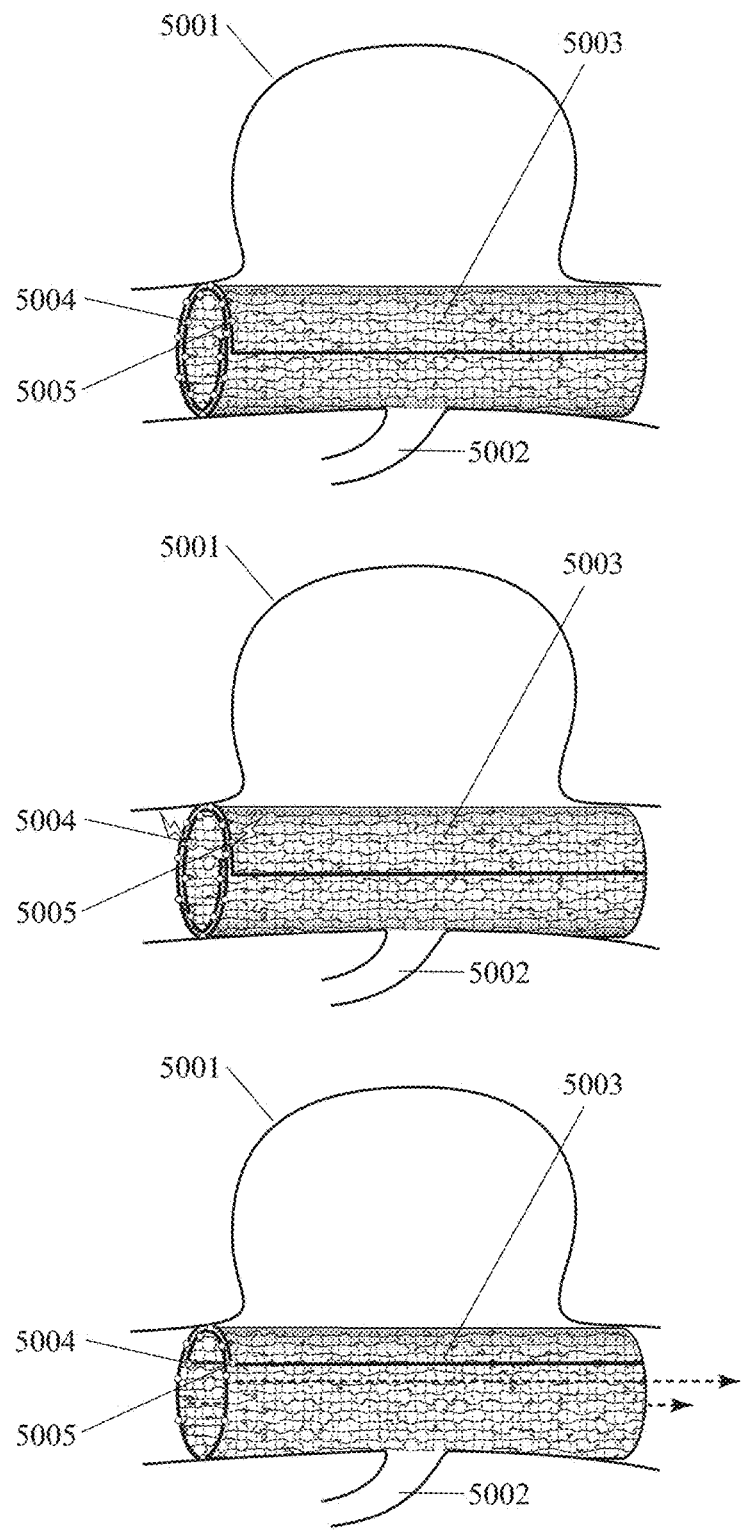
FIG. 50 shows a parent-vessel aneurysm occlusion device comprising a longitudinal tubular mesh with an adjustable spiral cross-sectional perimeter.

FIG. 50 shows three sequential longitudinal views of a device for occluding a cerebral aneurysm comprising: a longitudinal tubular mesh (e.g. a stent) 5003 with a spiral cross-sectional perimeter, wherein the longitudinal tubular mesh is configured to be inserted into a blood vessel that includes an aneurysm sac 5001 and an entrance to a branching blood vessel 5002, wherein a first portion of the circumference of the longitudinal tubular mesh is configured to face the aneurysm sac, and wherein a second portion of the circumference of the longitudinal tubular mesh is configured to face the entrance to the branching blood vessel; and a plurality of detachable connections, including connections 5004 and 5005, which hold longitudinal segments of the longitudinal tubular mesh together, wherein a selected subset of the detachable connections are detached after the device has been deployed in the blood vessel, wherein this detachment separates a subset of the longitudinal segments which are along the second portion of the circumference of the longitudinal tubular mesh from the rest of the longitudinal tubular mesh, wherein the subset of longitudinal segments are removed from rest of the longitudinal tubular mesh, and wherein this removal of longitudinal segments causes the longitudinal tubular mesh to have greater porosity along the second portion of its circumference than along the first portion of its circumference.

The upper third of FIG. 50 shows this device at a first point in time after the longitudinal tubular mesh has been inserted into the blood vessel, but before a selected subset of connections has been detached. The middle third of FIG. 50 shows this device at a second point in time after the selected subset of connections have been detached, but before a selected subset of longitudinal segments (along the entrance to the branching blood vessel) has been removed. The lower third of FIG. 50 shows this device at a third point in time after the selected subset of longitudinal segments (along the entrance to the branching blood vessel) has been removed, resulting in a stent with greater porosity along the entrance to the branching blood vessel and lower porosity along the aneurysm neck. In an example, detachment of a subset of connections can be done by applying electromagnetic energy to them (e.g. melting them).

FIG. 51 shows three sequential views of a device for occluding a cerebral aneurysm comprising: a distal tubular mesh 5102, wherein the distal end of the distal tubular mesh is pinched and inverted, and wherein the distal tubular mesh is configured to be inserted into and expanded within an aneurysm 5101 at a first distance from the aneurysm neck; a proximal tubular mesh 5103, wherein the distal end of the proximal tubular mesh is pinched and inverted, and wherein the proximal tubular mesh is configured to be inserted into and expanded within the aneurysm at a second distance from the aneurysm neck, wherein the second distance is less than the first distance, wherein the distal tubular mesh and the proximal tubular mesh have a first configuration during their delivery to the aneurysm in which they are not nested, and wherein the distal tubular mesh and the proximal tubular mesh have a second configuration after expansion within the aneurysm in which they are nested; and a longitudinal member (e.g. wire, string, or filament) which connects the distal tubular mesh and the proximal tubular mesh while the meshes are being delivered to the aneurysm.

The upper third of FIG. 51 shows this device at a first point in time before the distal tubular mesh and the proximal tubular mesh have been inserted into and expanded within an aneurysm sac. At this first point in time, the distal tubular mesh and the proximal tubular mesh are not in a nested configuration. The middle third of FIG. 51 shows this device at a second point in time after the distal tubular mesh has been partially expanded within the aneurysm sac and before the proximal tubular mesh has been expanded within the aneurysm sac. The lower third of FIG. 51 shows this device at a third point in time after both the distal tubular mesh and the proximal tubular mesh have been inserted into and expanded within the aneurysm sac. At this third point in time, the distal tubular mesh and the proximal tubular mesh are in a nested configuration.

In an example, a proximal tubular mesh can have a smaller diameter than a distal tubular mesh. In an example, a proximal tubular mesh can be nested within the concavity of a distal tubular mesh in their second configuration. In an example, a distal tubular mesh can have a smaller diameter than a proximal tubular mesh. In an example, a distal tubular mesh can be nested within the concavity of a tubular mesh in their second configuration. In an example, the proximal diameter of a distal tubular mesh can be larger than the diameter of an aneurysm neck. In an example, the proximal diameter of a proximal tubular mesh can be larger than the diameter of an aneurysm neck.

In an example, distal and proximal tubular meshes can be coaxial in their second configuration. In an example, the longitudinal axes of distal and proximal tubular meshes can be coaxial in their second configuration. In an example, distal and proximal tubular meshes can have a first degree of overlap in their first configuration and a second degree of overlap in their second configuration, wherein the second degree is greater than the first degree. In an example, distal and proximal tubular meshes do not overlap in their first configuration, but do overlap in their second configuration. In an example, the distal ends of the distal and proximal tubular meshes can be pinched and inverted. In an example, the distal ends of the distal and proximal tubular meshes can be pinched and partially inverted. Alternatively, the distal ends of the distal and proximal tubular meshes can be pinched, but not inverted.

In an example, distal and proximal tubular meshes can be changed from their first configuration to their second configuration by pulling (or pushing) a longitudinal member (e.g. wire, string, or filament) which connects the meshes. In an example, a device operator can change distal and proximal tubular meshes from their first configuration to their second configuration by pulling (or pushing) a longitudinal member (e.g. wire, string, or filament) which connects the meshes. In an example, this device can be deployed in the following sequence: first, the distal tubular mesh is inserted into and expanded within an aneurysm sac; and second, the proximal tubular mesh is inserted into and expanded within the distal tubular mesh. In an example, a longitudinal member which connects the distal and proximal tubular meshes can then be detached and removed.

In an example, a device for occluding a cerebral aneurysm comprising: a distal hemispherical mesh, wherein the distal hemispherical mesh is configured to be inserted into and expanded within an aneurysm at a first distance from the aneurysm neck; a proximal hemispherical mesh, wherein the proximal hemispherical mesh is configured to be inserted into and expanded within the aneurysm at a second distance from the aneurysm neck, wherein the second distance is less than the first distance, wherein the distal hemispherical mesh and the proximal hemispherical mesh have a first configuration during their delivery to the aneurysm in which they are not nested, and wherein the distal hemispherical mesh and the proximal hemispherical mesh have a second configuration after expansion within the aneurysm in which they are nested; and a longitudinal member (e.g. wire, string, or filament) which connects the distal hemispherical mesh and the proximal hemispherical mesh while the meshes are being delivered to the aneurysm.

In an example, a device for occluding a cerebral aneurysm comprising: a distal convex mesh, wherein the distal convex mesh is configured to be inserted into and expanded within an aneurysm at a first distance from the aneurysm neck; a proximal convex mesh, wherein the proximal convex mesh is configured to be inserted into and expanded within the aneurysm at a second distance from the aneurysm neck, wherein the second distance is less than the first distance, wherein the distal convex mesh and the proximal convex mesh have a first configuration during their delivery to the aneurysm in which they are not nested, and wherein the distal convex mesh and the proximal convex mesh have a second configuration after expansion within the aneurysm in which they are nested; and a longitudinal member (e.g. wire, string, or filament) which connects the distal convex mesh and the proximal convex mesh while the meshes are being delivered to the aneurysm.

FIG. 52 shows three sequential views of a device for occluding a cerebral aneurysm comprising: a distal tubular mesh 5202, wherein the distal end of the distal tubular mesh is pinched and inverted, and wherein the distal tubular mesh is configured to be inserted into and expanded within an aneurysm 5201 at a first distance from the aneurysm neck; a proximal tubular mesh 5203, wherein the proximal end of the proximal tubular mesh is pinched and inverted, and wherein the proximal tubular mesh is configured to be inserted into and expanded within the aneurysm at a second distance from the aneurysm neck, wherein the second distance is less than the first distance, wherein the distal tubular mesh and the proximal tubular mesh have a first configuration during their delivery to the aneurysm in which they do not overlap, and wherein the distal tubular mesh and the proximal tubular mesh have a second configuration after expansion within the aneurysm in which they overlap; and a longitudinal member (e.g. wire, string, or filament) which connects the distal tubular mesh and the proximal tubular mesh while the meshes are being delivered to the aneurysm.

The upper third of FIG. 52 shows this device at a first point in time before the distal tubular mesh and the proximal tubular mesh have been inserted into and expanded within an aneurysm sac. At this first point in time, the distal tubular mesh and the proximal tubular mesh do not overlap. The middle third of FIG. 52 shows this device at a second point in time after the distal tubular mesh has been partially expanded within the aneurysm sac and before the proximal tubular mesh has been expanded within the aneurysm sac. The lower third of FIG. 52 shows this device at a third point in time after both the distal tubular mesh and the proximal tubular mesh have been inserted into and expanded within the aneurysm. At this third point in time, the distal tubular mesh and the proximal tubular mesh overlap.

In an example, a proximal tubular mesh can have a smaller diameter than a distal tubular mesh. In an example, a proximal tubular mesh can fit into the concavity of a distal tubular mesh in their second configuration. In an example, a distal tubular mesh can have a smaller diameter than a proximal tubular mesh. In an example, a distal tubular mesh can fit into the concavity of a tubular mesh in their second configuration. In an example, the proximal diameter of a distal tubular mesh can be larger than the diameter of an aneurysm neck. In an example, the distal diameter of a proximal tubular mesh can be larger than the diameter of an aneurysm neck.

In an example, distal and proximal tubular meshes can have a first degree of overlap in their first configuration and a second degree of overlap in their second configuration, wherein the second degree is greater than the first degree. In an example, distal and proximal tubular meshes do not overlap in their first configuration, but do overlap in their second configuration. In an example, the distal end of the distal tubular mesh and the proximal end of the proximal tubular mesh can be pinched and inverted. In an example, the distal end of the distal tubular mesh and the proximal end of the proximal tubular mesh can be pinched and partially inverted. Alternatively, ends of the distal and proximal tubular meshes can be pinched, but not inverted.

In an example, distal and proximal tubular meshes can be changed from their first configuration to their second configuration by pulling (or pushing) the longitudinal member (e.g. wire, string, or filament) which connects the meshes. In an example, a device operator can change the distal and proximal tubular meshes from their first configuration to their second configuration by pulling (or pushing) a longitudinal member (e.g. wire, string, or filament) which connects the meshes. In an example, this device can be deployed in the following sequence: first, the distal tubular mesh is inserted into and expanded within an aneurysm sac; and second, the proximal tubular mesh is inserted into and expanded within the distal tubular mesh. In an example, a longitudinal member which connects the distal and proximal tubular meshes can then be detached and removed.

In an example, a device for occluding a cerebral aneurysm comprising: a distal hemispherical mesh which opens in a proximal direction, wherein the distal hemispherical mesh is configured to be inserted into and expanded within an aneurysm at a first distance from the aneurysm neck; a proximal hemispherical mesh which opens in a distal direction, wherein the proximal hemispherical mesh is configured to be inserted into and expanded within the aneurysm at a second distance from the aneurysm neck, wherein the second distance is less than the first distance, wherein the distal hemispherical mesh and the proximal hemispherical mesh have a first configuration during their delivery to the aneurysm in which they do not overlap, and wherein the distal hemispherical mesh and the proximal hemispherical mesh have a second configuration after expansion within the aneurysm in which they overlap; and a longitudinal member (e.g. wire, string, or filament) which connects the distal hemispherical mesh and the proximal hemispherical mesh while the meshes are being delivered to the aneurysm. In an example, the distal and proximal hemispherical meshes can combine to form a spherical or toroidal mesh in their second configuration.

In an example, a device for occluding a cerebral aneurysm comprising: a distal convex mesh which opens in a proximal direction, wherein the distal convex mesh is configured to be inserted into and expanded within an aneurysm at a first distance from the aneurysm neck; a proximal convex mesh which opens in a distal direction, wherein the proximal convex mesh is configured to be inserted into and expanded within the aneurysm at a second distance from the aneurysm neck, wherein the second distance is less than the first distance, wherein the distal convex mesh and the proximal convex mesh have a first configuration during their delivery to the aneurysm in which they do not overlap, and wherein the distal convex mesh and the proximal convex mesh have a second configuration after expansion within the aneurysm in which they overlap; and a longitudinal member (e.g. wire, string, or filament) which connects the distal convex mesh and the proximal convex mesh while the meshes are being delivered to the aneurysm. In an example, the distal and proximal hemispherical meshes can combine to form an ellipsoidal or toroidal mesh in their second configuration.

FIG. 54 shows three sequential views of a device for occluding a cerebral aneurysm comprising: a helical wire 5402 which is configured to be inserted into an aneurysm sac 5401, wherein the maximum diameter of the helical structure of the wire is larger than the diameter of the aneurysm neck; and a longitudinal plurality of sliding embolic masses 5403 (e.g. compressible balls, soft polyhedrons, microsponges, hydrogels, longitudinal meshes, longitudinal ribbons, or soft coils) which can slide along the length of the helical wire, wherein the sliding embolic masses are slid (e.g. pushed) along the length of the helical wire into the aneurysm sac after the helical wire has been inserted into the aneurysm sac, and wherein accumulation of the sliding embolic masses within the aneurysm sac reduces and/or prevents blood flow into the aneurysm sac.

The upper third of FIG. 54 shows this device at a first point in time after a helical wire has been inserted into an aneurysm sac, but before the plurality of sliding embolic masses have been slid along the helical wire into the aneurysm sac. The middle third of FIG. 54 shows this device at a second point in time as a plurality of sliding embolic masses are being slid (e.g. pushed) along the length of the helical wire into the aneurysm sac. The lower third of FIG.

54 shows this device at a third point in time after the plurality of sliding embolic masses have accumulated within the aneurysm sac and a proximal section of the helical wire has been detached and removed.

In an example, sliding embolic members can be compressible balls. In an example, sliding embolic members can be soft polyhedrons. In an example, the sliding embolic members can be microsponges. In an example, the sliding embolic members can be hydrogels. In an example, the sliding embolic members can be longitudinal mesh segments. In an example, the sliding embolic members can be longitudinal ribbon segments. In an example, the sliding embolic members can be soft coils. In an example, the sliding embolic members can be beads. In an example, the slide embolic members have openings and/or holes through which the helical wire goes. In an example, the slide embolic members have central openings and/or holes through which the helical wire goes. In an example, the slide embolic members can be remotely slid and/or pushed along the length of the helical wire by the device operator. In an example, the helical structure of the helical wire can form a generally globular (e.g. spherical or ellipsoidal) shape.

FIG. 55 shows a cross-sectional view of a device for occluding a cerebral aneurysm comprising: a bowl-shaped mesh 5502 which is configured to be inserted into and expanded within an aneurysm sac 5501 so as to span the neck of the aneurysm from inside the aneurysm sac, wherein the bowl-shaped mesh is formed by pinching each of the distal and proximal ends of a tubular mesh and then moving these ends toward each other; a distal lumen (e.g. cylinder, ring, band, tube, or torus) 5503 within which the distal end of the tubular mesh is pinched and/or bound; a proximal lumen (e.g. cylinder, ring, band, tube, or torus) 5504 within which the proximal end of the tubular mesh is pinched and/or bound; and one or more embolic members (e.g. coils, string-of-pearls embolic strands, hydrogels, microsponges, or beads) 5505 which are inserted through the proximal lumen and through the distal lumen into the aneurysm sac, wherein accumulation of the one or more embolic members in the aneurysm sac helps to occlude the aneurysm and to hold the bowl-shaped mesh against the neck of the aneurysm.

In this example, the distal lumen protrudes from the bowl-shaped mesh in a distal direction and the proximal lumen protrudes from the bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved toward each other and the bowl-shaped mesh can be formed before the device is deployed. In an example, the distal and proximal ends of the tubular mesh can be moved toward each other to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted.

In an example, this device can further comprise a closure mechanism within the proximal lumen, wherein this mechanism is closed after embolic members have been inserted into the aneurysm sac. In an example, the device can further comprise a catheter through which embolic members are transported into the aneurysm sac. In an example, this catheter can extend through the proximal and distal lumens. In an example, this device can further comprise a flexible net, mesh, bag, or liner which is inserted into the aneurysm sac (before the bowl-shaped mesh) in order to contain the embolic members. In an example, such a flexible net, mesh, bad, or liner can expand to fill between 80% and 100% of the aneurysm sac as it is filled with embolic members.

FIG. 56 shows a cross-sectional view of a device for occluding a cerebral aneurysm comprising: a bowl-shaped mesh 5602 which is configured to be inserted into and expanded within an aneurysm sac 5601 so as to span the neck of the aneurysm from inside the aneurysm sac, wherein the bowl-shaped mesh is formed by pinching each of the distal and proximal ends of a tubular mesh and then moving these ends toward each other; a distal lumen (e.g. cylinder, ring, band, tube, or torus) 5603 within which the distal end of the tubular mesh is pinched and/or bound; a proximal lumen (e.g. cylinder, ring, band, tube, or torus) 5604 within which the proximal end of the tubular mesh is pinched and/or bound; and one or more embolic members (e.g. coils, string-of-pearls embolic strands, hydrogels, microsponges, or beads) 5605 which are inserted through the proximal lumen and through the distal lumen into the aneurysm sac, wherein accumulation of the one or more embolic members in the aneurysm sac helps to occlude the aneurysm and to hold the bowl-shaped mesh against the neck of the aneurysm.

In this example, the distal lumen extends inward from surface of the bowl-shaped mesh in a proximal direction and the proximal lumen extends outward from the bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved toward each other and the bowl-shaped mesh can be formed before the device is deployed. In an example, the distal and proximal ends of the tubular mesh can be moved toward each other to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted.

In an example, this device can further comprise a closure mechanism within the proximal lumen, wherein this mechanism is closed after embolic members have been inserted into the aneurysm sac. In an example, the device can further comprise a catheter through which embolic members are transported into the aneurysm sac. In an example, this catheter can extend through the proximal and distal lumens. In an example, this device can further comprise a flexible net, mesh, bag, or liner which is inserted into the aneurysm sac (before the bowl-shaped mesh) in order to contain the embolic members. In an example, such a flexible net, mesh, bad, or liner can expand to fill between 80% and 100% of the aneurysm sac as it is filled with embolic members.

FIG. 57 shows a cross-sectional view of a device for occluding a cerebral aneurysm comprising: a bowl-shaped mesh 5702 which is configured to be inserted into and expanded within an aneurysm sac 5701 so as to span the neck of the aneurysm from inside the aneurysm sac, wherein the bowl-shaped mesh is formed by pinching each of the distal and proximal ends of a tubular mesh and then moving these ends toward each other; a distal lumen (e.g. cylinder, ring, band, tube, or torus) 5703 within which the distal end of the tubular mesh is pinched and/or bound; a proximal lumen (e.g. cylinder, ring, band, tube, or torus) 5704 within which the proximal end of the tubular mesh is pinched and/or bound; and one or more embolic members (e.g. coils, string-of-pearls embolic strands, hydrogels, microsponges, or beads) 5705 which are inserted through the proximal lumen and through the distal lumen into the aneurysm sac, wherein accumulation of the one or more embolic members in the aneurysm sac helps to occlude the aneurysm and to hold the bowl-shaped mesh against the neck of the aneurysm.

In this example, the distal lumen extends inward from surface of the bowl-shaped mesh in a proximal direction and the proximal lumen extends inward from the surface of the bowl-shaped mesh in a distal direction. In this example, the bowl-shaped mesh is double-layered. In this example, the concavity of the bowl-shaped mesh opens in a distal direction. In an example, the distal and proximal ends of the tubular mesh can be moved toward each other and the bowl-shaped mesh can be formed before the device is deployed. In an example, the distal and proximal ends of the tubular mesh can be moved toward each other to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted.

In an example, this device can further comprise a closure mechanism within the proximal lumen, wherein this mechanism is closed after embolic members have been inserted into the aneurysm sac. In an example, the device can further comprise a catheter through which embolic members are transported into the aneurysm sac. In an example, this catheter can extend through the proximal and distal lumens. In an example, this device can further comprise a flexible net, mesh, bag, or liner which is inserted into the aneurysm sac (before the bowl-shaped mesh) in order to contain the embolic members. In an example, such a flexible net, mesh, bad, or liner can expand to fill between 80% and 100% of the aneurysm sac as it is filled with embolic members.

FIG. 58 shows a cross-sectional view of a device for occluding a cerebral aneurysm comprising: a bowl-shaped mesh 5802 which is configured to be inserted into and expanded within an aneurysm sac 5801 so as to span the neck of the aneurysm from inside the aneurysm sac, wherein the bowl-shaped mesh is formed by pinching each of the distal and proximal ends of a tubular mesh and then moving these ends toward each other; a distal lumen (e.g. cylinder, ring, band, tube, or torus) 5803 within which the distal end of the tubular mesh is pinched and/or bound; a proximal lumen (e.g. cylinder, ring, band, tube, or torus) 5804 within which the proximal end of the tubular mesh is pinched and/or bound; and one or more embolic members (e.g. coils, string-of-pearls embolic strands, hydrogels, microsponges, or beads) 5805 which are inserted through the proximal lumen and through the distal lumen into the aneurysm sac, wherein accumulation of the one or more embolic members in the aneurysm sac helps to occlude the aneurysm and to hold the bowl-shaped mesh against the neck of the aneurysm.

In this example, the distal lumen extends outward from surface of the bowl-shaped mesh in a distal direction and the proximal lumen extends inward from the surface of the bowl-shaped mesh in a distal direction. In this example, the bowl-shaped mesh is double-layered. In this example, the concavity of the bowl-shaped mesh opens in a distal direction. In an example, the distal and proximal ends of the tubular mesh can be moved toward each other and the bowl-shaped mesh can be formed before the device is deployed. In an example, the distal and proximal ends of the tubular mesh can be moved toward each other to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted.

In an example, this device can further comprise a closure mechanism within the proximal lumen, wherein this mechanism is closed after embolic members have been inserted into the aneurysm sac. In an example, the device can further comprise a catheter through which embolic members are transported into the aneurysm sac. In an example, this catheter can extend through the proximal and distal lumens. In an example, this device can further comprise a flexible net, mesh, bag, or liner which is inserted into the aneurysm sac (before the bowl-shaped mesh) in order to contain the embolic members. In an example, such a flexible net, mesh, bad, or liner can expand to fill between 80% and 100% of the aneurysm sac as it is filled with embolic members.

FIG. 59 shows a cross-sectional view of a device for occluding a cerebral aneurysm comprising: a bowl-shaped mesh 5902 which is configured to be inserted into and expanded within an aneurysm sac 5901 so as to span the neck of the aneurysm from inside the aneurysm sac, wherein the bowl-shaped mesh is formed by pinching and/or binding together the distal and proximal ends of a tubular mesh; a lumen (e.g. cylinder, ring, band, tube, or torus) 5903 within which the distal and proximal ends of the tubular mesh are pinched and/or bound; and one or more embolic members (e.g. coils, string-of-pearls embolic strands, hydrogels, microsponges, or beads) 5904 which are inserted through the lumen into the aneurysm sac, wherein accumulation of the one or more embolic members in the aneurysm sac helps to occlude the aneurysm and to hold the bowl-shaped mesh against the neck of the aneurysm.

In this example, the lumen extends outward from surface of the bowl-shaped mesh in a distal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted.

In an example, this device can further comprise a closure mechanism within the lumen, wherein this mechanism is closed after embolic members have been inserted into the aneurysm sac. In an example, the device can further comprise a catheter through which embolic members are transported into the aneurysm sac. In an example, this catheter can extend through the lumen. In an example, this device can further comprise a flexible net, mesh, bag, or liner which is inserted into the aneurysm sac (before the bowl-shaped mesh) in order to contain the embolic members. In an example, such a flexible net, mesh, bad, or liner can expand to fill between 80% and 100% of the aneurysm sac as it is filled with embolic members.

FIG. 60 shows a cross-sectional view of a device for occluding a cerebral aneurysm comprising: a bowl-shaped mesh 6002 which is configured to be inserted into and expanded within an aneurysm sac 6001 so as to span the neck of the aneurysm from inside the aneurysm sac, wherein the bowl-shaped mesh is formed by pinching and/or binding together the distal and proximal ends of a tubular mesh; a lumen (e.g. cylinder, ring, band, tube, or torus) 6003 within which the distal and proximal ends of the tubular mesh are pinched and/or bound; and one or more embolic members (e.g. coils, string-of-pearls embolic strands, hydrogels, microsponges, or beads) 6004 which are inserted through the lumen into the aneurysm sac, wherein accumulation of the one or more embolic members in the aneurysm sac helps to occlude the aneurysm and to hold the bowl-shaped mesh against the neck of the aneurysm.

In this example, the lumen extends outward from surface of the bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted.

In an example, this device can further comprise a closure mechanism within the lumen, wherein this mechanism is closed after embolic members have been inserted into the aneurysm sac. In an example, the device can further comprise a catheter through which embolic members are transported into the aneurysm sac. In an example, this catheter can extend through the lumen. In an example, this device can further comprise a flexible net, mesh, bag, or liner which is inserted into the aneurysm sac (before the bowl-shaped mesh) in order to contain the embolic members. In an example, such a flexible net, mesh, bad, or liner can expand to fill between 80% and 100% of the aneurysm sac as it is filled with embolic members.

FIGS. 61 through 66 show six examples of an intrasacular aneurysm occlusion device comprising: a neck bridge with a proximal portion which has a distal-facing concavity, wherein the neck bridge is inserted and then radially-expanded within an aneurysm sac, and wherein the neck bridge is wider than the aneurysm neck and covers the interior of the aneurysm neck after the neck bridge has been expanded within the aneurysm sac; a proximal-to-distal opening and/or lumen through the neck bridge, wherein embolic material (such as embolic coils, ribbons, microsponges, hydrogels, balls, beads, polygons, foam, gel, liquid, or string-of-pearls embolic strands) is inserted through the opening and/or lumen into the aneurysm sac; and a closure mechanism which closes the proximal-to-distal opening and/or lumen after the embolic material has been inserted into the aneurysm sac. The following variations can be applied to the examples shown in FIGS. 61 through 66.

In an example, a neck bridge can have a convex shape after expansion within an aneurysm sac. In an example, the proximal portion (e.g. proximal side) of a convex neck bridge can have a distal-facing concavity and the distal portion (e.g. distal side) of the convex neck bridge can have a proximal-facing concavity. In an example, a neck bridge can have an ellipsoidal, football, or disk shape after expansion within the aneurysm sac. In an example, a neck bridge can have a globular and/or spherical shape after expansion within the aneurysm sac. In example, a neck bridge can have a toroidal (e.g. bagel or doughnut) shape after expansion within an aneurysm sac. In example, a neck bridge can have an apple, barrel, pear, or pumpkin shape after expansion within an aneurysm sac.

In an example, a neck bridge can have a bowl (e.g. hemispherical or paraboloidal) shape after expansion within an aneurysm sac. In an example, a bowl-shaped neck bridge can be pre-formed (e.g. using shape memory material) before deployment. In example, a double-layer bowl-shaped neck bridge can be formed by longitudinally-collapsing the distal portion of an ellipsoidal or spherical mesh after expansion of the ellipsoidal or spherical mesh within an aneurysm sac. In example, a double-layer bowl-shaped neck bridge can be formed by inverting the distal half of an ellipsoidal or spherical mesh after expansion of the ellipsoidal or spherical mesh within an aneurysm sac.

In an example, a neck bridge can expand to a diameter which is greater than the diameter of an aneurysm neck. In an example, a neck bridge can expand to diameter which is at least 25% greater than the diameter of an aneurysm neck. In an example, a neck bridge can expand to a diameter which greater than 95% of the largest diameter of the aneurysm sac. In an example, the distal perimeter of a neck bridge can expand where the aneurysm sac is widest. In an example, a neck bridge can be expanded within the proximal half of an aneurysm sac. In an example, a neck bridge can cover the proximal half of the perimeter of an aneurysm sac, including a cross-section of the aneurysm neck.

In an example, a neck bridge can comprise a wire mesh. In an example, a neck bridge can comprise a braided or woven wire mesh. In an example, wires in neck bridge can have a hub-and-spoke configuration, wherein the hubs are at central proximal and distal locations and the spokes extend radially outward from the hubs. In an example, wires in a neck bridge can have a ring-and-spoke configuration, wherein a subset of wires extend radially outward from a central location and a subset of wires encircle the central location in rings. In an example, rings may be closer together toward the center of the neck bridge than the periphery of the neck bridge. In an example, wires in a neck bridge may form a hexagonal mesh (e.g. honeycomb mesh). In an example, wires in neck bridge may be undulating (e.g. sinusoidal). In an example, a neck bridge can comprise a wire mesh with helical wires.

In an example, proximal and distal ends of wires in a mesh neck bridge can connect to proximal and distal hubs (e.g. rings) in the neck bridge. In an example, a neck bridge can further comprise a proximal ring wherein proximal ends of wires in a mesh connect to the proximal ring. In an example, the proximal ring can be part of outer perimeter of a proximal-to-distal opening through which embolic material is inserted through the neck bridge into the aneurysm sac. In an example, a neck bridge can further comprise a distal ring wherein distal ends of wires in a mesh connect to the distal ring. In an example, the distal ring can be part of the outer perimeter of a proximal-to-distal opening through which embolic material is inserted through the neck bridge into the aneurysm sac. In an example, a wire mesh neck bridge can comprise wires, wherein both ends of each wire are connected to a distal hub (e.g. ring) of the neck bridge. In an example, a wire mesh neck bridge can comprise wires, wherein both ends of each wire are connected to a proximal hub (e.g. ring) of the neck bridge.

In an example, a neck bridge can comprise a two-layer bowl-shaped wire mesh wherein one end of each wire is connected to a proximal ring, wherein one end of each wire is connected to a distal ring, and wherein there is an opening or lumen between the proximal and distal rings through which embolic material is inserted into the aneurysm sac. In an example, a neck bridge can comprise a two-layer bowl-shaped wire mesh wherein one end of each wire is connected to a proximal ring, wherein one end of each wire is connected to a distal ring, and wherein there is a cylindrical lumen between the proximal and distal rings through which embolic material is inserted into the aneurysm sac. In an example, a neck bridge can comprise a two-layer bowl-shaped wire mesh wherein one end of each wire is connected to a proximal ring, wherein one end of each wire is connected to a distal ring, wherein there is an opening or lumen between the proximal and distal rings through which embolic material is inserted into the aneurysm sac, and wherein there is closure mechanism located on the proximal ring, the distal ring, or in the lumen between the rings. In an example, a neck bridge can comprise a proximal-to-distal opening or lumen through which embolic material is inserted into the aneurysm sac, wherein there is closure mechanism in the opening or lumen which prevents embolic material from escaping from the sac after the closure mechanism has been activated.

In an example, a neck bridge can comprise a wire mesh and a low-porosity membrane which are attached to each other. In an example, a neck bridge can comprise a low-porosity membrane which is adhered to a wire mesh. In an example, a neck bridge can comprise a wire mesh inside a low-porosity membrane. In an example, a neck bridge can comprise a wire mesh covered with a low-porosity membrane, wherein the wire mesh causes the neck bridge to self-expand when released from a catheter in an aneurysm sac and the low-porosity membrane makes the neck bridge less porous than it would be with only the wire mesh.

In an example, a neck bridge can comprise a wire mesh and a low-porosity polymer mesh which are attached to each other. In an example, a neck bridge can comprise a low-porosity polymer mesh which is adhered to a wire mesh. In an example, a neck bridge can comprise a wire mesh inside a low-porosity polymer mesh. In an example, a neck bridge can comprise a wire mesh covered with a low-porosity polymer mesh, wherein the wire mesh causes the neck bridge to self-expand when released from a catheter in an aneurysm sac and the low-porosity polymer mesh makes the neck bridge less porous than it would be with only the wire mesh. In an example, a neck bridge can comprise an elastomeric low-porosity polymer membrane attached to a wire mesh. In an example, a neck bridge can comprise metal wires and polymer strands which are braided or woven together. In an example, a neck bridge can comprise a polymer mesh. In an example, a neck bridge can comprise a 3D-printed polymer mesh.

In an example, a proximal portion of a neck bridge can be less porous than a distal portion of a neck bridge. In an example, a proximal portion of a wire mesh neck bridge can be less porous than a distal portion of a wire mesh neck bridge. In an example, wires in a proximal portion of a wire mesh neck bridge can be closer together than wires in a distal portion of a wire mesh neck bridge. In an example, wires in a proximal portion of a wire mesh neck bridge can be thicker than wires in a distal portion of a wire mesh neck bridge. In an example, a central portion of a neck bridge can be less porous than a peripheral portion of a neck bridge. In an example, a central portion of a wire mesh neck bridge can be less porous than a peripheral portion of a wire mesh neck bridge. In an example, wires in a central portion of a wire mesh neck bridge can be closer together than wires in a peripheral portion of a wire mesh neck bridge. In an example, wires in a central portion of a wire mesh neck bridge can be thicker than wires in a peripheral portion of a wire mesh neck bridge.

In an example, a neck bridge can comprise a single layer of material. In an example, a wire mesh neck bridge can comprise a single layer of wire mesh. In an example, a wire mesh neck bridge can comprise two or more layers of wire mesh. In an example, a proximal portion of a wire mesh neck bridge can have more layers of mesh than a distal portion of the neck bridge. In an example, a central portion of a wire mesh neck bridge can have more layers of mesh than a peripheral portion of the neck bridge. In an example, a neck bridge can comprise an inverted tubular mesh. In an example, a proximal portion of a wire mesh neck bridge can comprise an inverted tubular mesh. In an example, a distal portion of a wire mesh neck bridge can comprise an inverted tubular mesh.

In an example, a proximal-to-distal opening and/or lumen through a neck bridge can be at the center of the neck bridge. In an example, a proximal-to-distal opening and/or lumen can be in the middle of a neck bridge. In an example, a proximal-to-distal opening can be an opening (or hole) in the center of a neck bridge. In an example, a proximal-to-distal lumen can be a lumen (or opening) through the center of a neck bridge. In an example, a proximal-to-distal opening can be an opening (or hole) along the longitudinal axis of a neck bridge. In an example, a proximal-to-distal lumen can be a lumen (or opening) along the longitudinal axis of a neck bridge. In an example, the ends of wires in a wire mesh neck bridge can converge to a ring and/or cylinder around a proximal-to-distal opening and/or lumen through the neck bridge. In an example, proximal ends of wires in a wire mesh neck bridge can converge to a proximal ring around a proximal-to-distal opening and/or lumen through the neck bridge and distal ends of wires in a wire mesh neck bridge can converge to a distal ring around the proximal-to-distal opening and/or lumen.

In an example, there can be a single opening or lumen through a neck bridge through which embolic material is inserted into the aneurysm sac. In an example, there can be a single, centrally-located opening or lumen through a neck bridge through which embolic material is inserted into the aneurysm sac. In an example, there can be a single, off-center opening or lumen through a neck bridge through which embolic material is inserted into the aneurysm sac. In an example, there can be a plurality of opening or lumens through a neck bridge through which embolic material can be selectively inserted into the aneurysm sac. In an example, there can be a plurality of off-center opening or lumens through a neck bridge through which embolic material can be selectively inserted into the aneurysm sac.

In an example, there can be a single opening or lumen through a neck bridge through which embolic material is inserted into the aneurysm sac which can be remotely opened or closed by the device operator via one or more closure mechanisms. In an example, there can be a single, centrally-located opening or lumen through a neck bridge through which embolic material is inserted into the aneurysm sac which can be remotely opened or closed by the device operator via one or more closure mechanisms. In an example, there can be a single, off-center opening or lumen through a neck bridge through which embolic material is inserted into the aneurysm sac which can be selectively and remotely opened or closed by the device operator via one or more closure mechanisms. In an example, there can be a plurality of opening or lumens through a neck bridge through which embolic material is inserted into the aneurysm sac which can be selectively and remotely opened or closed by the device operator via one or more closure mechanisms. In an example, there can be a plurality of off-center opening or lumens through a neck bridge through which embolic material is inserted into the aneurysm sac which can be remotely opened or closed by the device operator via one or more closure mechanisms.

In an example, a closure mechanism for any of the examples shown FIGS. 61 through 66 can be selected from any of the closure mechanisms shown in FIGS. 33 through 38. In an example a closure mechanism can be located at the proximal entrance to a proximal-to-distal opening and/or lumen through a neck bridge. In an example a closure mechanism can be located at the distal end of a proximal-to-distal opening and/or lumen through a neck bridge. In an example a closure mechanism can be located inside a proximal-to-distal opening and/or lumen through a neck bridge. In an example, a closure mechanism can be an elastic annular valve through which embolic material is inserted into an aneurysm sac. In an example, a valve can be an elastic annular valve. In an example, an elastic annular valve can passively open when embolic material (such as an embolic coil, hydrogel, microsponge, bead, or a string-of-pearls embolic strand) pushes through it. In an example, an elastic annular valve can passively close when after the embolic material has passed through. In an example, an elastic annular valve can be made from an elastomeric material. In an example, an elastic annular valve can be made from a silicone-based polymer.

In an example, a closure mechanism can be a leaflet valve. In an example, a leaflet valve can be a bi-leaflet valve or tri-leaflet valve, analogous to a heart valve. In an example, a leaflet valve can have a single leaflet or flap. In an example, a leaflet valve can have four or more leaflets or flaps. In an example, a leaflet valve can passively open when embolic material (such as an embolic coil, hydrogel, microsponge, bead, or a string-of-pearls embolic strand) pushes through it. In an example, a leaflet valve can passively close when after the embolic material has passed through. In an example, a leaflet valve can be made from an elastomeric material. In an example, a leaflet valve can be made from a silicone-based polymer. In an example, a leaflet valve can be made from rigid material such as metal. In an example, a leaflet valve can be made from titanium and carbon. In an example, a leaflet valve can be remotely opened and/or closed by the operator of the device. In an example, a leaflet valve can be remotely opened and/or closed by an operator (by the application of electromagnetic energy).

In an example, a closure mechanism can be a rotational valve through which embolic material is inserted into an aneurysm sac. In an example, when first and second openings (holes) in a rotational valve are not aligned, then the valve is in its closed configuration. When the first and second openings (holes) are aligned, then the valve is in its open configuration. In an example, a rotational valve can be changed from its closed configuration to its open configuration, or vice versa, by rotating (or revolving, pivoting, turning, or twisting) a first layer relative to a second layer, or vice versa. In an example, a rotational valve can comprise two or more overlapping (e.g. parallel) layers with openings (holes). When the openings (holes) of different layers are not aligned, then the valve is closed. When the opening (holes) of different layers are aligned, then the valve is open. In an example, the valve can be opened or closed by rotating one layer relative to the other layer. In an example, one or both layers can be rotated remotely by the operator of the device, enabling the operator to open or close the valve remotely.

In an example, a closure mechanism can be a sliding valve through which embolic material is inserted into an aneurysm sac. In an example, when a sliding flap (lid) covers an opening or lumen, then a valve is in its closed configuration. When the sliding flap (lid) does not cover the opening or lumen, then the valve is in its open configuration. In this example, the valve is changed from its closed configuration to its open configuration, or vice versa, by moving the sliding flap. In an example, the sliding flap can be moved remotely by the operator of the device, enabling the operator to open or close the valve remotely.

In an example, a closure mechanism can be a pivoting valve through which embolic material is inserted into an aneurysm sac. In an example, when a pivoting flap (lid) does not block an opening or lumen, then a valve is in its open configuration. In an example, a valve can be changed from its closed configuration to its open configuration, or vice versa, by pivoting (rotating) the flap around a central axis. In the example of a square opening, a valve could changed from its closed configuration to its open configuration, or vice versa, by pivoting (rotating) a flap around one side. In an example, the pivoting flap can be moved remotely by the operator of the device, enabling the operator to open or close the valve remotely. This type of pivoting valve is analogous to the valves which are used in circular air ducts for HVAC (heating, ventilation, and air conditioning) systems in buildings.

In an example, a closure mechanism can be a plug-mechanism valve through which embolic material is inserted into an aneurysm sac. In an example, when a plug blocks an opening or lumen, then the plug mechanism is in its closed configuration. When a plug does not block the opening or lumen, then the plug mechanism is in its open configuration. In this example, the plug mechanism is changed from its open configuration to its closed configuration by inserting a plug into the opening or lumen. In an example, a plug can be inserted remotely by the operator of the device, enabling the operator to close the plug mechanism remotely. In an example, a plug can be inserted into a lumen by using a guidewire or hydraulic pressure. In an example, a plug can be made from hydrogel.

In an example, a closure mechanism can be created by movement of two overlapping layers of a neck bridge. In an example, when proximal and distal layers of a neck bridge are aligned, then embolic material can be inserted through the neck bridge, but when the proximal and distal layers are misaligned, then embolic material cannot go through the neck bridge (e.g. cannot escape from the aneurysm sac). In an example, the proximal and distal layers of a neck bridge can be misaligned by sliding and/or rotating one layer relative to the other layer. In an example, the proximal and distal layers of a neck bridge can be misaligned remotely by the operator of the device. In an example, layers of a neck bridge can be aligned when the device is first deployed so that embolic material can be inserted through the neck bridge into the aneurysm sac, but the layers can subsequently be misaligned so that the embolic material does not escape from the aneurysm sac.

In an example, a closure mechanism can be opened or closed by application of electromagnetic energy to a neck bridge. In an example, application of electromagnetic energy to a wire mesh neck bridge can cause the wires to become more or less flexible. When the wires are more flexible, a catheter can be inserted through the neck bridge in order to insert embolic material into the aneurysm sac, but when the wires are less flexible, the embolic material cannot escape out from the aneurysm sac through the next bridge. In an example, application of electromagnetic energy can cause one or more wires to bend, creating a (temporary) opening through the neck bridge. In example, when the electromagnetic energy is stopped, then the one or more wires return to a configuration which closes the opening through the neck bridge.

In an example, a closure mechanism can comprise filling the interior of a neck bridge with embolic material after filling the interior of an aneurysm sac with embolic material. For example, first a catheter be inserted through an opening or lumen in the neck bridge into the aneurysm sac and embolic material can be inserted into the aneurysm sac until the aneurysm sac is "full" (e.g. reaches desired packing density). Then, the catheter can be withdrawn so that its end is within the interior of a (convex) neck bridge and embolic material can be inserted into the interior of the neck bridge. Then, the catheter can be withdrawn from the neck bridge and body, leaving the opening or lumen through the neck bridge closed by occlusion with embolic material. In an example, a first type of embolic material can be inserted into the aneurysm sac and a second type of embolic material can be inserted into the interior of the neck bridge. In an example, the first material can be more flexible, compressible, and/or elastomeric than the second material. In an example, embolic material can be packed more tightly inside the neck bridge than in the aneurysm sac.

In an example, embolic material can be inserted into an aneurysm sac through an opening or lumen in a neck bridge when a closure mechanism is open and prevented from escaping out from the aneurysm sac when the closure mechanism is closed. In an example, the closure mechanism can be remotely controlled by the operating of the device. In an example, embolic material can be selected from the group consisting of: embolic coils, embolic ribbons, microsponges, hydrogels, microspheres, embolic polygons, foam, gel, congealing liquid, and string-of-pearls embolic strands. In an example, embolic coils can be inserted into an aneurysm sac through an opening or lumen in a neck bridge when a closure mechanism is open. In an example, embolic ribbons can be inserted into an aneurysm sac through an opening or lumen in a neck bridge when a closure mechanism is open. In an example, microsponges can be inserted into an aneurysm sac through an opening or lumen in a neck bridge when a closure mechanism is open.

In an example, hydrogels can be inserted into an aneurysm sac through an opening or lumen in a neck bridge when a closure mechanism is open. In an example, microspheres can be inserted into an aneurysm sac through an opening or lumen in a neck bridge when a closure mechanism is open. In an example, embolic polygons can be inserted into an aneurysm sac through an opening or lumen in a neck bridge when a closure mechanism is open. In an example, foam can be inserted into an aneurysm sac through an opening or lumen in a neck bridge when a closure mechanism is open. In an example, gel can be inserted into an aneurysm sac through an opening or lumen in a neck bridge when a closure mechanism is open. In an example, congealing liquid can be inserted into an aneurysm sac through an opening or lumen in a neck bridge when a closure mechanism is open. In an example, string-of-pearls embolic strands can be inserted into an aneurysm sac through an opening or lumen in a neck bridge when a closure mechanism is open.

In an example, an aneurysm occlusion device comprising a neck bridge with a closeable opening or lumen through it can further comprise a guidewire through the opening or lumen. In an example, this guidewire can help navigate a catheter through the opening or lumen in order to insert embolic material through the opening or lumen into the aneurysm sac. In an example, the guidewire can extend through the opening or lumen even before the neck bridge is inserted and expanded within the aneurysm sac. In an example, the guidewire can be extended through the opening or lumen after the neck bridge has been inserted and expanded within the aneurysm sac. In an example, the guidewire can be used to guide an embolic-delivering catheter through the opening or lumen in the neck bridge and then withdraw from the opening or lumen after the catheter has been inserted into the aneurysm sac to deliver embolic material.

FIG. 61 shows an example of an intrasacular aneurysm occlusion device comprising: a convex (e.g. ellipsoidal or disk shaped) neck bridge 6102 with a proximal portion which has a distal-facing concavity, wherein the neck bridge is inserted and then radially-expanded within an aneurysm sac 6101, and wherein the neck bridge is wider than the aneurysm neck and covers the aneurysm neck after the neck bridge has been expanded within the aneurysm sac; a central (e.g. central axial) proximal-to-distal opening and/or lumen 6103 through the neck bridge, wherein embolic material (such as embolic coils, ribbons, balls, beads, polygons, foam, gel, liquid, or string-of-pearls embolic strands) is inserted through the opening and/or lumen into the aneurysm sac; and a closure mechanism 6104 which closes the proximal-to-distal opening and/or lumen after the embolic material has been inserted into the aneurysm sac. Example variations discussed above and in priority-linked disclosures can be applied to this example where relevant.

FIG. 62 shows an example of an intrasacular aneurysm occlusion device comprising: a bowl-shaped (e.g. hemispherical or paraboloidal) neck bridge 6202 with a proximal portion which has a distal-facing concavity, wherein the neck bridge is inserted and then radially-expanded within an aneurysm sac 6201, and wherein the neck bridge is wider than the aneurysm neck and covers the aneurysm neck after the neck bridge has been expanded within the aneurysm sac; a central (e.g. central axial) proximal-to-distal opening and/or lumen 6203 through the neck bridge, wherein embolic material (such as embolic coils, ribbons, balls, beads, polygons, foam, gel, liquid, or string-of-pearls embolic strands) is inserted through the opening and/or lumen into the aneurysm sac; and a closure mechanism 6204 which closes the proximal-to-distal opening and/or lumen after the embolic material has been inserted into the aneurysm sac. Example variations discussed above and in priority-linked disclosures can be applied to this example where relevant.

FIG. 63 shows an example of an intrasacular aneurysm occlusion device comprising: a toroidal (e.g. bagel or doughnut shaped) neck bridge 6302 with a proximal portion which has a distal-facing concavity, wherein the neck bridge is inserted and then radially-expanded within an aneurysm sac 6301, and wherein the neck bridge is wider than the aneurysm neck and covers the aneurysm neck after the neck bridge has been expanded within the aneurysm sac; a central (e.g. central axial) proximal-to-distal opening and/or lumen 6303 through the neck bridge, wherein embolic material (such as embolic coils, ribbons, balls, beads, polygons, foam, gel, liquid, or string-of-pearls embolic strands) is inserted through the opening and/or lumen into the aneurysm sac; and a closure mechanism 6304 which closes the proximal-to-distal opening and/or lumen after the embolic material has been inserted into the aneurysm sac. Example variations discussed above and in priority-linked disclosures can be applied to this example where relevant.

FIG. 64 shows an example of an intrasacular aneurysm occlusion device comprising: a convex (e.g. ellipsoidal or disk shaped) neck bridge 6402 with a proximal portion which has a distal-facing concavity, wherein the neck bridge is inserted and then radially-expanded within an aneurysm sac 6401, and wherein the neck bridge is wider than the aneurysm neck and covers the aneurysm neck after the neck bridge has been expanded within the aneurysm sac; an off-center (e.g. non-axial) proximal-to-distal opening and/or lumen 6403 through the neck bridge, wherein embolic material (such as embolic coils, ribbons, balls, beads, polygons, foam, gel, liquid, or string-of-pearls embolic strands) is inserted through the opening and/or lumen into the aneurysm sac; and a closure mechanism 6404 which closes the proximal-to-distal opening and/or lumen after the embolic material has been inserted into the aneurysm sac. Example variations discussed above and in priority-linked disclosures can be applied to this example where relevant.

FIG. 65 shows an example of an intrasacular aneurysm occlusion device comprising: a bowl-shaped (e.g. hemispherical or paraboloidal) neck bridge 6502 with a proximal portion which has a distal-facing concavity, wherein the neck bridge is inserted and then radially-expanded within an aneurysm sac 6501, and wherein the neck bridge is wider than the aneurysm neck and covers the aneurysm neck after the neck bridge has been expanded within the aneurysm sac; an off-center (e.g. non-axial) proximal-to-distal opening and/or lumen 6503 through the neck bridge, wherein embolic material (such as embolic coils, ribbons, balls, beads, polygons, foam, gel, liquid, or string-of-pearls embolic strands) is inserted through the opening and/or lumen into the aneurysm sac; and a closure mechanism 6504 which closes the proximal-to-distal opening and/or lumen after the embolic material has been inserted into the aneurysm sac. Example variations discussed above and in priority-linked disclosures can be applied to this example where relevant.

FIG. 66 shows an example of an intrasacular aneurysm occlusion device comprising: a toroidal (e.g. bagel or doughnut shaped) neck bridge 6602 with a proximal portion which has a distal-facing concavity, wherein the neck bridge is inserted and then radially-expanded within an aneurysm sac 6601, and wherein the neck bridge is wider than the aneurysm neck and covers the aneurysm neck after the neck bridge has been expanded within the aneurysm sac; an off-center (e.g. non-axial) proximal-to-distal opening and/or lumen 6603 through the neck bridge, wherein embolic material (such as embolic coils, ribbons, balls, beads, polygons, foam, gel, liquid, or string-of-pearls embolic strands) is inserted through the opening and/or lumen into the aneurysm sac; and a closure mechanism 6604 which closes the proximal-to-distal opening and/or lumen after the embolic material has been inserted into the aneurysm sac. Example variations discussed above and in priority-linked disclosures can be applied to this example where relevant.

I claim:

1. An intrasacular aneurysm occlusion device comprising:
a neck bridge with a distal-facing concavity, wherein the neck bridge is configured to be inserted and then radially-expanded within an aneurysm sac, wherein the neck bridge is configured to be wider than the aneurysm neck and cover the interior of the aneurysm neck after the neck bridge has been expanded within the aneurysm sac wherein the neck bridge comprises a wire mesh, wherein the neck bridge further comprises a proximal ring, wherein wires in the wire mesh connect to the proximal ring, where the proximal ring forms the perimeter of a proximal-to-distal opening and/or lumen through the neck bridge, and wherein embolic material is inserted through the opening and/or lumen into the aneurysm sac;
a flap or plug which closes the proximal-to-distal opening and/or lumen after the embolic material has been inserted into the aneurysm sac; and
a wire connected to the flap or plug, wherein the flap or plug is remotely opened or closed by an operator by the operator pushing, pulling, or rotating the wire.

2. An intrasacular aneurysm occlusion device comprising:
a neck bridge with a distal-facing concavity, wherein the neck bridge is configured to be inserted and then radially-expanded within an aneurysm sac, wherein the neck bridge is configured to be wider than the aneurysm neck and cover the interior of the aneurysm neck after the neck bridge has been expanded within the aneurysm sac wherein the neck bridge comprises a wire mesh, wherein the neck bridge further comprises a proximal ring, wherein wires in the wire mesh connect to the proximal ring, where the proximal ring forms the perimeter of a proximal-to-distal opening and/or lumen through the neck bridge, and wherein embolic material is inserted through the opening and/or lumen into the aneurysm sac; and
a leaflet valve which closes the proximal-to-distal opening and/or lumen after the embolic material has been inserted into the aneurysm sac.

3. An intrasacular aneurysm occlusion device comprising:
a neck bridge with a distal-facing concavity, wherein the neck bridge is configured to be inserted and then radially-expanded within an aneurysm sac, wherein the neck bridge is configured to be wider than the aneurysm neck and cover the interior of the aneurysm neck after the neck bridge has been expanded within the aneurysm sac wherein the neck bridge comprises a wire mesh, wherein the neck bridge further comprises a proximal ring, wherein wires in the wire mesh connect to the proximal ring, where the proximal ring forms the perimeter of a proximal-to-distal opening and/or lumen through the neck bridge, and wherein embolic material is inserted through the opening and/or lumen into the aneurysm sac; and
a leaflet valve which closes the proximal-to-distal opening and/or lumen after the embolic material has been inserted into the aneurysm sac, wherein the leaflet valve is remotely opened or closed by an operator by the application of electromagnetic energy.

* * * * *